United States Patent [19]

Schatz

[11] Patent Number: 5,851,796
[45] Date of Patent: Dec. 22, 1998

[54] AUTOREGULATORY TETRACYCLINE-REGULATED SYSTEM FOR INDUCIBLE GENE EXPRESSION IN EUCARYOTES

[75] Inventor: David G. Schatz, New Haven, Conn.

[73] Assignee: Yale University, New Haven, Conn.

[21] Appl. No.: 474,169

[22] Filed: Jun. 7, 1995

[51] Int. Cl.[6] .......................... C12N 15/63; C12N 15/79; C12N 5/10; C07H 21/04
[52] U.S. Cl. .................... 435/69.1; 435/320.1; 435/325; 435/410; 536/23.4
[58] Field of Search ............................... 435/69.1, 240.1, 435/320.1, 325, 410; 536/23.4

[56] References Cited

U.S. PATENT DOCUMENTS 5,464,758  11/1995  Gossen et al. ........................... 435/69.1

FOREIGN PATENT DOCUMENTS

| 0 494 724 | 7/1992 | European Pat. Off. . |
| 0 519 336 | 12/1992 | European Pat. Off. . |
| 39 34 454 | 4/1991 | Germany . |
| WO 91/19784 | 12/1991 | WIPO . |
| WO 92/11358 | 7/1992 | WIPO . |
| WO 92/20808 | 11/1992 | WIPO . |
| WO 96/01313 | 1/1996 | WIPO . |

OTHER PUBLICATIONS

Hofmann, A. et al., "Rapid retroviral delivery of tetracycline–inducible genes in a single autoregulatory cassette," *Proc. Natl. Acad. Sci. USA* 93:5185–5190 (May 1996).

Shockett, P. et al., "A modified tetracycline–regulated system provides autoregulatory, inducible gene expression in cultured cells and transgenic mice," *Proc. Natl. Acad. Sci. USA* 92:6522–6526 (Jul. 1995).

Furth, P.A., et al., "Temporal control of gene expression in transgenic mice by a tetracycline–responsive promoter," *Proc. Natl. Acad. Sci. USA* 91:9302–9306 Sep. (1994).

Gill, G. & Ptashne, M., "Negative effect of the Transcriptional activation GAL4," *Nature* 334(25):721–724 Aug. (1988).

Goodnow, et al., "Induction of self–tolerance in mature peripheral B lymphocytes," *Nature* 342:385–391 Nov. (1989).

Gossen, M. & Bujard, H., "Tight control of gene expression in mammalian cells by tetracycline–responsive promoters," *Proc. Natl. Acad. Sci. USA* 89:5547–5551 Jun. (1992).

Hesse, et al., "Extrachromosomal DNA Substrates in Pre–B Cells Undergo Inversion or Deletion at Immunoglobulin V–(D)–J Joining Signals," *Cell* 49:775–783 Jun. (1987).

Hillen, W. & Wissmann, A., in: *Protein–Nucleic Acid Interaction, Topics in Molecular and Structural Biology*, Saenger, W. & Heinemann, U., eds., Macmillan, London (1989) pp. 143–162.

(List continued on next page.)

*Primary Examiner*—Mindy Fleisher
*Assistant Examiner*—Robert Schwartzman
*Attorney, Agent, or Firm*—Sterne, Kessler, Goldstein & Fox, P.L.L.C.

[57] ABSTRACT

A tetracycline-regulated system which provides autoregulatory, inducible gene expression in cultured cells and transgenic animals is described. In the autoregulatory plasmid pTet-tTAk, a modified tTA gene called tTAk was placed under the control of Tetp. Tetracycline prevents tTA from binding to Tetp, preventing expression of both tTA and luciferase. This negative feedback cycle ensures that little or no tTA is produced in the presence of tetracycline, thereby reducing or eliminating possible toxic effects. When tetracycline is removed, however, this strategy predicts that tiny amounts of tTA protein (which may result from the leakiness of the minimal promoter), will bind to Tet-op and stimulate expression of the tTAk gene. A positive feedforward loop is initiated which in turn leads to higher levels of expression of tTA and thus, luciferase. Polynucleotide molecules encoding the autoregulatory system, as well as methods of enhancing or decreasing the expression of desired genes, and kits for carrying out these methods are described.

28 Claims, 35 Drawing Sheets

OTHER PUBLICATIONS

Hinrichs, W., et al., "Structure of the Tet Repressor–Tetracycline Complex and Regulation of Antibiotic Resistance," *Science* 264:418–420 Apr. (1994).

Jones, S., et al., "Induction of the Cypla–1 dioxin–responsive enhancer in transgenic mice," *Nucl. Acids. Res.* 19(23):6547–6551 (1991).

Kozak, M., "Compilation and anaylsis of sequence upstream from the translational start site in eukaryotic mRNA," *Nucl. Acids. Res.* 12:857–872 (1984).

Lewis, S. M. & Hesse, J. E., "Cutting and closing without recombination in V(D)J joining," *EMBO J.* 10:3631–3639 (1991).

Lieber, M., et al., "Developmental stage specificity of the lymphoid V(D)J recombination activity," *Genes and Devel.* 1:751–761 (1987).

Oettinger, M., et al., "RAG–1 and RAG–2, Adjacent Genes That Synergistically Acitivate V(D)J Recombination," *Science* 248:1517–1523 Jun. (1990).

Oltz, E., et al., "A V(D) J Recombinase–Inducible B–Cell Line: Role of Transcriptional Enhancer Elements in Directing V(D)J Recombination," *Mol. Cell. Biol.* 13(10):6223–6230 Oct. (1993).

Schatz, D., et al., "The V(D)J Recombination Activating Gene , RAG–1," *Cell* 59:1035–1048 Dec. (1989).

Schatz, D., et al., "V(D)J Recombination: Molecular Biology and Regulation," *Annu. Rev. Immunol.* 10:359–383 (1992).

Silver, D., et al., "Dispensable sequence motifs in the RAG–1 and RAG–2 genes for plasmid V(D)J recombination," *Proc. Natl. Acad. Sci. USA* 90:6100–6104 Jul. (1993).

Yarranton, G., "Inducible vector for expression in mammalian cells," *Curr. Opin. Biotech.* 3:506–511 (1992).

Altschmied, L., et al., "A Threonine to Alanine Exchange at Position 40 of Tet Repressor Alters the Recognition of the Sixth Base Pair of tet Operator from GC to AT," *EMBO J.* 7(12):4011–4017 (1988).

Baim, S.B., et al., "A Chimeric Mammalian Transactivator Based on the lac Repressor that is Regulated by Temperature and Isopropyl β–D–Thiogalactopyranoside," *Proc. Natl. Acad. Sci. USA* 88:5072–5076 (1991).

Barkley, M.D., and Bourgeois, S., "Repressor Recognition of Operator and Effectors," in: *The Operon*, Miller, J., and Reznikoff, W., eds., Cold Spring Harbor, NY: Cold Spring Harbor Laboratory Press, pp. 177–220 (1980).

Beilmann, A., et al., "Functional Analysis of the Pathogenesis–related 1a Protein Gene Minimal Promoter Region. Comparison of Reporter Gene Expression in Transient and in Stable Transfections," *Eur. J. Biochem.* 196:415–421 (1991).

Boshart, M., et al., "A Very Strong Enhancer is Located Upstream of an Immediate Early Gene of Human Cytomegalovirus," *Cell* 41:521–530 (1985).

Bradley, A., "Modifying the Mammalian Genome by Gene Targeting," *Curr. Opin. Biotech.* 2:823–829 (1991).

Chang, Y.C., et al., "Identification of Aspergillus brlA Response Elements (BREs) by Genetic Selection in Yeast," *Genetics* 133:29–38 (Jan. 1993).

Clark, J.M., Jr., and Switzer, R.L., "Study of the Properties of β–Galactosidase," in: *Experimental Biochemistry*, New York: W.H. Freeman and Co., pp. 97–103 (1977).

Courey, A.J., and Tjian, R., "Analysis of Sp1 In Vivo Reveals Multiple Transcriptional Domains, Inlcuding a Novel Glutamine–Rich Activation Motif," *Cell* 55:887–898 (1988).

Deuschle, U., et al., "Regulated Expression of Foreign Genes in Mammalian Cells Under the Control of Coliphage T3 RNA Polymerase and lac Repressor," *Proc. Natl. Acad. Sci. USA* 86:5400–5404 (1989).

Dewet, J.R., et al., "Firefly Luciferase Gene: Structure and Expression in Mammalian Cells," *Mol. Cell. Biol.* 7(2):725–737 (1987).

Dynan, W.S., and Chervitz, S.A., "Characterization of a Minimal Simian Virus 40 Late Promoter: Enhancer Elements in the 72–Base–Pair Repeat Not Required," *J. Virol.* 63(3):1420–1427 (1989).

Epstein–Baak, R., et al., "Inducible Transformation of Cells from Transgenic Mice Expressing SV40 under lac Operon Control," *Cell Growth & Differentiation* 3:127–134 (1992).

Figge, J., et al., "Stringent Regulation of Stably Integrated Chloramphenicol Acetyl Transferase Genes by E. coli lac Repressor in Monkey Cells," *Cell* 52:713–722 (1988).

Fishman, G.I., et al., "Tetracycline–Regulated Cardiac Gene Expression In Vivo," *J. Clin. Invest.* 93:1864–1868 (Apr. 1994).

Frankel, A.D., and Kim. P.S., "Modular Structure of Transcription Factors: Implications for Gene Regulation," *Cell* 65:717–719 (1991).

Gatz, C., and Quail, P.H., "Tn10–Encoded tet Repressor Can Regulate an Operator–Containing Plant Promoter," *Proc. Natl. Acad. Sci. USA* 85:1394–1397 (1988).

Gatz, C., et al., "Regulation of a Modified CaMV 35S Promoter by the Tn10–Encoded Tet Repressor in Transgenic Tobacco," *Mol. Gen. Genet.* 227:229–237 (1991).

Giniger, E., and Ptashne, M., "Transcription in Yeast Activated by a Putative Amphipathic α Helix Linked to a DNA Binding Unit," *Nature* 330:670–672 (1987).

Gossen, M., et al., "Control of Gene Activity in Higher Eukaryotic Cells by Prokaryotic Regulatory Elements," *TIBS* 18:471–475 (Dec. 1993).

Labow, M.A., et al., "Conversion of the lac Repressor into an Allosterically Regulated Transcriptional Activator for Mammalian Cells," *Mol. Cell. Biol.* 10(7):3343–3356 (1990).

LaMantia, G., et al., "Identification of Regulatory Elements Within the Minimal Promoter Region of the Human Endogenous ERV9 Proviruses: Accurate Transcription Initiation is Controlled by an Inr–Like Element," *Nucl. Acids Res.* 20(16):4129–4136 (1992).

Luo, Z., et al., "Characterization of a Minimal Promoter Element Required for Transcription of the Mouse Type IIβ Regulatory Subunit (RIIβ) pf cAMP–dependent Protein Kinase," *J. Biol. Chem.* 267(34):24738–24747 (1992).

Ma, J., and Ptashne, M., "A New Class of Yeast Transcriptional Activators," *Cell* 51:113–119 (1987).

Mansour, S.L., et al., "Disruption of the Proto–Oncogene int–2 in Mouse Embryo–Derived Stem Cells: a General Strategy for Targeting Mutations to Non–Selectable Genes," *Nature* 336:348–352 (1988).

Mermod, N., et al., "The Proline–Rich Transcriptional Activator of CTF/NF–I is Distinct from the Replication and DNA Binding Domain," *Cell* 58:741–753 (1989).

Mitchell, P.J., and Tjian, R., "Transcriptional Regulation in Mammalian Cells by Sequence–Specific DNA Binding Proteins," *Science* 245:371–378 (1989).

Nordeen, S.K., "Luciferase Reporter Gene Vectors for Analysis of Promoters and Enhancers," *BioTechniques* 6(5):454–457 (1988).

Postle, K., et al., "Nucleotide Sequence of the Repressor Gene of the TN10 Tetracycline Resistance Determinant," *Nucl. Acids Res.* 12 (12):4849–4863 (1984).

Ptashne, M., "How Eukaryotic Transcriptional Activators Work," *Nature* 335:683–689 (1988).

Sadowski, I., et al., "GAL4–VP16 is an Unusually Potent Transcriptional Activator," *Nature* 335:563–564 (1988).

Seeburg, P.H., et al., "The $GABA_A$ Receptor Family: Molecular and Functional Diversity," *Cold Spring Harbor Symp. Quant. Biol.* 55:29–40 (1990).

Seipel, K., et al., "Different Activation Domains Stimulate Transcription From Remote ('Enhancer') and Proximal ('Promoter') Positions," *EMBO J.* 11 (13):4961–4968 (1992).

Smithies, O., et al., "Insertion of DNA Sequences into the Human Chromosomal β–Globin locus by Homologous Recombination," *Nature* 317:230–234 (1985).

Southern, P. J., and Berg, P., "Transformation of Mammalian Cells to Antibiotic Resistance with a Bacterial Gene Under Control of the SV40 Early Region Promoter," *J. Molec. Appl. Genet.* 1:327–341 (1982).

Takahashi, M., et al., "Kinetic and Equilibrium Characterization of the Tet Repressor–Tetracycline Complex by Fluorescence Measurements. Evidence for Divalent Metal Ion Requirement and Energy Transfer," *J. Mol. Biol.* 187:341–348 (1986).

Tanaka, M., and Herr, W., "Differential Transcriptional Activation by Oct.–1 and Oct.–2: Interdependent Activation Domains Induce Oct.–2 Phosphorylation," *Cell* 60:375–386 (1990).

Tovar, K., et al., "Identification and Nucleotide Sequence of the Class E tet Regulatory Elements and Operator and Inducer Binding of the Encoded Purified Tet Repressor," *Mol. Gen. Genet.* 215:76–80 (1988).

Triezenberg, S.J., et al., "Functional Dissection of VP16, the trans–Activator of Herpes Simplex Virus Immediate Early Gene Expression," *Genes & Devel.* 2:718–729 (1988).

Unger, B., et al., "Nucleotide Sequence of the Gene, Protein Purification and Characterization of the pSC101–encoded Tetracycline Resistance–Gene–Repressor," *Gene* 31:103–108 (1984).

Unger, B., et al., "Nucleotide Sequence of the Repressor Gene of the RA1 Tetracycline Resistance Determinant: Structural and Functional Comparison with Three Related Tet Repressor Genes," *Nucl. Acids Res.* 1 12 (20):7693–7703 (1984).

Waters, S.H., et al., "The Tetracycline Resistance Determinants of RP1 and Tn1721: Nucleotide Sequence Analysis," *Nucl. Acids Res.* 11 (17):6089–6105 (1983).

Weinmann, P., et al., "A Chimeric Transactivator Allows Tetracycline–responsive Gene Expression in Whole Plants," *Plant J.* 5 (4):559–569 (Apr. 1994).

Wing, D., et al., "Conserved Function in *Nicotiana tabacum* of a Single Drosophila hsp70 Promoter Heat Shock Element When Fused to a Minimal T–DNA Promoter," *Mol. Gen. Genet.* 219:9–16 (1989).

Wyborski, D.L., and Short, J.M., "Analysis of Inducers of the *E. Coli* lac Repressor System in Mammalian Cells and Whole Animals," *Nucl. Acids Res.* 19(17):4647–4653 (1991).

Xia, C.L., et al., "Glutathione Transferase II. Its Minimal Promoter and Downstream cis–Acting Element," *Biochem. Biophys. Res. Commun.* 176(1):233–240 (1991).

Zambetti, G.P., et al., "A Mutant p53 Protein is Required for Maintenance of the Transformed Phenotype in Cells Transformed with p53 Plus ras cDNAs," *Proc. Natl. Acad. Sci. USA* 89:3952–3956 (1992).

English–language abstract for European Patent Publication No. EP 0 519 336 (Ref. AM1), Derwent WPI Accession No. 92–425576/52.

HHS/PHS (NIH) Grant Application entitled "Immunoglobulin and T Cell Receptor Gene Assembly," Schatz, D.G., Principal Investigator (Notice of Grant Award issued Mar. 31, 1992).

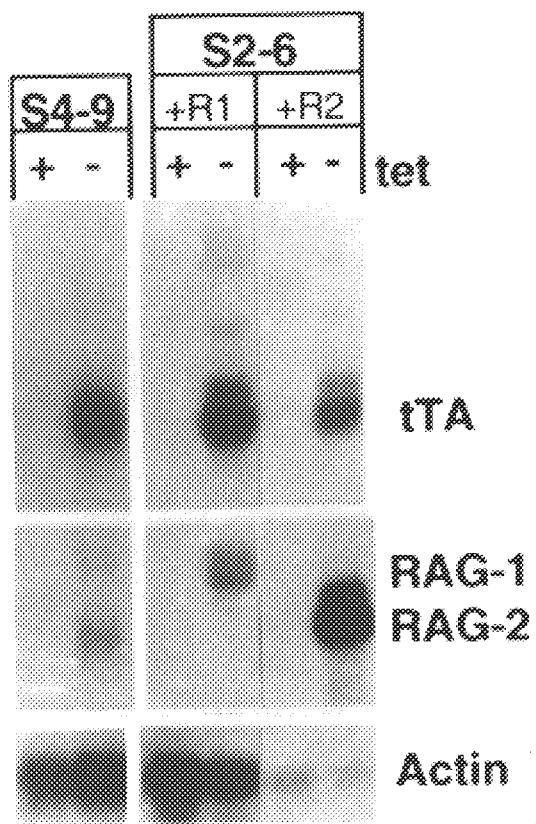
FIG. 3A
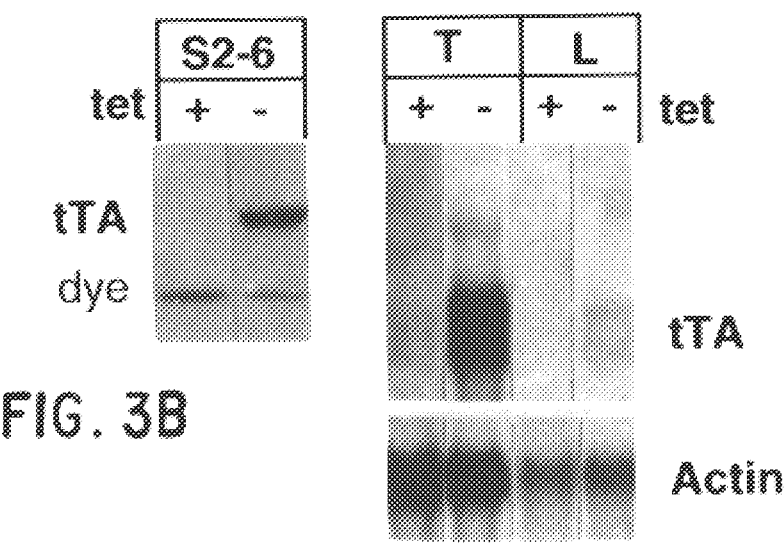
FIG. 3B
FIG. 3C

```
        SspI
  1  CTAAATTGTAAGCGTTAATATTTTGTTAAATTCGCGTTAAATTTTGTTAAATCAGCTCATTTTTAACCAATAGGCCG
 81  AAATCGGCAAAATCCCTTATAAATCAAAAGAATAGACCGAGATAGGGTTGAGTGTTGTTCCAGTTTGGAACAAGAGTCCA
161  CTATTAAAGAACGTGGACTCCAACGTCAAAGGGCGAAAAACGTCTATCAGGGCGATGGCCCACTACGTGAACCATCACC
241  CTAATCAAGTTTTTTGGGGTCGAGGTGCCGAGGTGCCGTAAAGCACTAAATCGGAACCCTAAAGGGAGCCCCGATTTAGAGCTTGAC
321  GGGGAAAGCCGGCGAACGTGGCGAGAAAGGAAGGAAGAAAGCGAAAGGAGCGGGCGCTAGGGCGCTGGCAAGTGTAGCG
401  GTCACGCTGCGCGTAACCACCACCACCCGCGCTTAATGCGCCGCGTCCATTCGCCATTCAGGCTGCG
                              PvuI                             PvuII
481  CAACTGTTGGGAAGGGCGATCGGTGCGGGCCCTCTTCGCTATTACGCCAGCTGGGCGAAAGGGGGATGCTGCAAGGCGAT
                                                                       BssHI
561  TAAGTTGGGTAACGCCCAGGGTTTTCCCAGTCACGACGTTGTAAAACGACGGCCAGTGAGCGCGTAATACGACTCACTA
           SstI BstXI      NotI    XbaI
641  TAGGGCGAATTGGAGCTCCACCGCGGTGGCGGCCGCTCTAGAGCAATTCCTTGCCTAATTAAATGAGGACTTAACCTG
                                                        ▼
721  TGGAAATATTTTGATGTGGGAAGCTGTTACTGTTAAAACTGAGGTTATTGGGTAACTGCTATGTTAAACTTGCATTCAG

801  GGACACAAAAAAACTCATGAAAAATGGTGCTGGAAAAACCCATTCAAGGGTCAAATTTTCATTTTTTGCTGTTGGTGGGGAA

PstI
881  CCTTTGGAGCTGCAGGGTGTGTTAGCAAACTACAGGACCAAATATCCTGCTCAAACTGTAACCCCAAAAAATGCTACAGT
```

FIG. 9B

```
961   TGACAGTCAGCAGATGAACACTGACCACAAGGCTGTTTTGGATAAGGATAATGCTTATCCAGTGGAGTGCTGGGTTCCTG

1041  ATCCAAGTAAAAATGAAAACACTAGATATTTTGGAACCTACACAGGTGGGGAAAATGTGCCTCCTGTTTGCACATTACT

1121  AACACAGCAACCACAGTGCTTCTTGATGAGCAGGGTGTTGGGCCCTTGTGCAAAGCTGACAGCTTGTATGTTCTGCTGT

1201  TGACATTTGTGGGCTGTTTACCAACACTTCTGGAACACAGCAGTGGAAGGACTTCCCAGATATTTTAAAATTACCCTTA

1281  GAAAGCGGTCTGTGAAAAACCCCTACCCAATTTCCTTTTTGTTAAGTGACCTAATTAACAGGAGGACACAGAGGGTGGAT

BamHI
1361  GGGCAGCCTATGATTGGAATGTCCTCTCAAGTAGAGGAGGTTAGGGTTTATGAGGACACAGAGGAGCTTCCTGGGGATCC

1441  AGACATGATAAGATACATTGATGAGTTTGGAACAAACCACAACTAGAATGCAGTGAAAAAAATGCTTTATTTGTGAAATTT

1521  GTGATGCTATTGCTTTATTTGTAACCATTATAAGCTGCAATAAACAAGTTAACAACAACAATTGCATTCATTTATGTTT
```

FIG. 9C

1601 CAGGTTCAGGGGGAGGTGTGGGAGGTTTTTTAAAGCAAGTAAAACCTCTACAAATGTGGTATGGCTGATTATGATCTTTG

1681 TGAAGGAACCTTACTTCTGTGGTGTGACATAATTGGACAAACTACCTACAGAGATTTAAAGCTCTAAGGTAAATATAAAA

1761 TTTTTAAGTGTATAATGTGTTAAACTACTGATTCTAATTGTTTGTGTATTTTAGATTCCAACCTATGGAACTGATGAATG

1841 GGAGCAGTGGTGGAATGCCTTTAATGAGGAAAACCTGTTTTGCTCAGAAGAAATGCCATCTAGTGATGATGAGGCTACTG

1921 CTGACTCTCAACATTCTACTCCTCCAAAAAAGAAGAGAAAGGTAGAAGACCCCAAGGACTTTCCTTCAGAATTGCTAAGT

2001 TTTTTGAGTCATGCTGTGTTTAGTAATAGAACTCTTGCTTGCTTTGCTATTTACACCACAAAGGAAAAAGCTGCACTGCT

2081 ATACAAGAAAATTATGGAAAAATATTCTGTAACCTTTATAAGTAGGCATAACAGTTATAATCATAACATACTGTTTTTC

2161 TTACTCCACACAGGCATAGAGTGTCTGCTATTAATAACTATGCTCAAAAATTGTGTACCTTTAGCTTTTAATTTGTAAA

FIG. 9D

```
2241  GGGGTTAATAAGGAATATTTGATGTATAGTGCCTTGACTAGAGATCCGCCTCCGGGGAATTTCTGCCATTCATCGCTTA

2321  TTATCACTTATTCAGGCGTAGCACCAGGCGTTTAAGGGCACCAATAACTGCCTTAAAAAAATTACGCCCGCCCTGCCAC

EcoRV   ClaI
                                      PstI  EcoRI  HindIII    SalI
2401  TCATCGCAGTGCTCTAGAACTAGTGGATCCCCCGGGCTGCAGGAATTCGATATCAAGCTTATCGATACCGTCGACCTCGA
          XbaI  SpeI  BamHI XbaI  BamHI         EcoRI
2481  CTCTAGAGGATCCCCGGGTACCGAGCTCGAATTCGGGGCCCGGGAGGCTGGATCGGTCCCGGTGTCTTCTATGGAGGTCA
                                      ← ← start site of trxn (?)

2561  AAACAGCGTGGATGGCGTCTCCAGGCGATCTGACGGTTCACTAAACGAGAGCTCTGCTTATATAGGCCTCCCACCGTACACG
                                                                    ← TATA BOX

2641  CCTACTCGACCCGGGTACCGAGCTCGACTTTCACTTTTCTCTATCACTGATAGGGAGTGGTAAACTGACTTTCACTTTT
      ▲

2721  CTCTATCACTGATAGGGAGTGGTAAACTGACTTTCACTTTTCTCTATCACTGATAGGGAGTGGTAAACTGACTTTCAC

2801  TTTTCTCTATCACTGATAGGGAGTGGTAAACTGACTTTCACTTTTTCTCTATCACTGATAGGGAGTGGTAAACTGACTT
                                                                                  XhoI
2881  TCACTTTTCTCTATCACTGATAGGGAGTGGTAAACTGACTTTCACTTTTTCTCTATCACTGATAGGGAGTGGTAAACTCG
```

FIG. 9E

```
                                    BssH II
2961  AGGGGGGGCCCGGTACCCAGCTTTTGTTCCCTTTAGTGAGGGTTAATTGCGGCTTGGCGTAATCATGGTCATAGCTGTT
3041  TCCTGTGTGAAATTGTTATCCGCTCACAATTCCACACAACATACGAGCCGGAAGCATAAAGTGTAAAGCCTGGGGTGCCT
                                                                            PvuII
3121  AATGAGTGAGCTAACTCACATTAATTGCGTTGCGCTCACTGCCCGCTTTCCAGTCGGGAAACCTGTCGTGCCAGCTGCAT
3201  TAATGAATCGGCCAACGCGCGGGGAGAGGCGGTTTGCGTATTGGGCGCTCTTCCGCTTCCTCGCTCACTGACTCGCTGCG
3281  CTCGGTCGTTCGGCTGCGGCGAGCGGTATCAGCTCACTCAAAGGCGGTAATACGGTTATCCACAGAATCAGGGGATAACG
3361  CAGGAAAGAACATGTGAGCAAAAGGCCAGCAAAAGGCCAGGAACCGTAAAAAGGCCGCGTTGCTGGCGTTTTTCCATAGG
3441  CTCCGCCCCCCTGACGAGCATCACAAAAATCGACGCTCAAGTCAGAGGTGGCGAAACCCGACAGGACTATAAAGATACCA
3521  GGCGTTTCCCCCTGGAAGCTCCCTCGTGCGCTCTCCTGTTCCGACCCTGCCGCTTACCGGATACCTGTCCGCCTTTCTCC
3601  CTTCGGGAAGCGTGGCGCTTTCTCATAGCTCACGCTGTAGGTATCTCAGTTCGGTGTAGGTCGTTCGCTCCAAGCTGGGC
3681  TGTGTGCACGAACCCCCCGTTCAGCCCGACCGCTGCGCCTTATCCGGTAACTATCGTCTTGAGTCCAACCCGGTAAGACA
3761  CGACTTATCGCCACTGGCAGCAGCCACTGGTAACAGGATTAGCAGAGCGAGGTATGTAGGCGGTGCTACAGAGTTCTTGA
3841  AGTGGTGGCCTAACTACGGCTACACTAGAAGGACAGTATTTGGTATCTGCGCTCTGCTGAAGCCAGTTACCTTCGGAAAA
3921  AGAGTTGGTAGCTCTTGATCCGGCAAACAAACCACCGCTGGTAGCGGTGGTTTTTTTGTTTGCAAGCAGCAGATTACGCG
4001  CAGAAAAAAAGGATCTCAAGAAGATCCTTTGATCTTTTCTACGGGGTCTGACGCTCAGTGGAACGAAAACTCACGTTAAG
4081  GGATTTGGTCATGAGATTATCAAAAAGGATCTTCACCTAGATCCTTTTAAATTAAAAATGAAGTTTTAAATCAATCTAA
4161  AGTATATATGAGTAAACTTGGTCTGACAGTTACCAATGCTTAATCAGTGAGGCACCTATCTCAGCGATCTGTCTATTTCG
4241  TTCATCCATAGTTGCCTGACTCCCCGTCGTGTAGATAACTACGATACGGGAGGGCTTACCATCTGGCCCCAGTGCTGCAA
4321  TGATACCGCGAGACCCACGCTCACCGGCTCCAGATTTATCAGCAATAAACCAGCCAGCCGGAAGGGCCGAGCGCAGAAGT
4401  GGTCCTGCAACTTTATCCGCCTCCATCCAGTCTATTAATTGTTGCCGGGAAGCTAGAGTAAGTAGTTCGCCAGTTAATAG
4481  TTTGCGCAACGTTGTTGCCATTGCTACAGGCATCGTGGTGTCACGCTCGTCGTTTGGTATGGCTTCATTCAGCTCCGGTT
                                                                            PvuI
4561  CCCAACGATCAAGGCGAGTTACATGATCCCCATGTTGTGCAAAAAAGCGGTTAGCTCCTTCGGTCCTCCGATCGTTGTC
4641  AGAAGTAAGTTGGCCGCAGTGTTATCACTCATGGTTATGGCAGCACTGCATAATTCTCTTACTGTCATGCCATCCGTAAG
```

FIG. 9F

```
        ScaI
4721  ATGCTTTCTGTGACTGGTGAGTACTCAACCAAGTCATTCTGAGAATAGTGTATGCGGGACCGAGTTGCTCTTGCCCGG
                                                                    XmnI
4801  CGTCAATACGGGATAATACCGCGCCACATAGCAGAACTTTAAAAGTGCTCATCATTGGAAAACGTTCTTCGGGGCGAAAA
4881  CTCTCAAGGATCTTACCGCTGTTGAGATCCAGTTCGATGTAACCCACTGTGCACCCAACTGATCTTCAGCATCTTTAC
4961  TTTCACCAGCGTTTCTGGGTGAGCAAAAACAGGAAGGCAAAATGCCGCAAAAAAGGGAATAAGGGCGACACGGAAATGTT
               SspI
5041  GAATACTCATACTCTTCCTTTTTCAATATTATTGAAGCATTTATCAGGGTTATTGTCTCATGAGCGGATACATATTTGAA
5121  TGTATTTAGAAAAATAAACAAATAGGGGTTCCGCGCACATTTCCCCGAAAAGTGCCAC
```

FIG. 9G

```
          SspI
   1   CTAAATTGTAAGCGTTAATATTTGTTAAAATTCGCGTTAAATTTTGTTAAATCAGCTCATTTTTTAACCAATAGGCCG
  81   AAATCGGCAAAATCCCTTATAAATCAAAAGAATAGACCGAGATAGGGTTGAGTGTTGTTCCAGTTTGGAACAAGAGTCA
 161   CTATTAAAGAACGTGGACTCCAACGTCAAAGGGCAAAAACCGTCTATCAGGCGATGGCCCACTACGTGAACCATCACC
 241   CTAATCAAGTTTTTTGGGGTCGAGGTGCCGTAAAGCACTAAATCGAACCCTAAAGGGAGCCCCGATTTAGAGCTTGAC
 321   GGGGAAAGCCGGCAAGCTGGCGAGAAGGAAGCAAAGGAAGAAAAGCGAAGAGGCGGCGCTAGGGCGCTGGCAAGTGTAGCG
 401   GTCACGCTGCGCGTAACCACCACACCCGCCGCCTTAATGCCGCCTACGGGCCGCTCCCATTCCCATTCAGGCTGCG
                 PvuI                                                    PvuII                BssHII
 481   CAACTGTTGGGAAGGGCGATCGGTGCGGGCCTCTTCGCTATTACGCCAGCTGGCGAAAGGGGGATGTGCTGCAAGGCCGAT
 561   TAAGTTGGGTAACGCCAGGGTTTTCCCAGTCACGACGTTGTAAAACGACGGCCAGTGAGCGCGCGTAATACGACTCACTA
           SstI
           SacI  BstXI    NotI   XbaI
 641   TAGGGCGAATTGGAGCTCCACCGCGGTGGCGGCCGCTCTAGAGCAATTCCTTTGCCTAATTTAAATGAGGACTTAACCTG
                                                                         ─────────▶
 721   TGGAAATATTTGATGTGGGAAGCTGTTACTGTTAAAACTGAGGTTATTGGGTAACTGCTATGTTAAACTTGCATTCAG
       ═══════════════════════════════════════════════════════════════════════════════
 801   GGACACAAAAAACTCATGAAAATGTGCTGGAAAACCATTCAAGGGTCAAATTTCATTTTTTGCTGTTGGTGGGAA
       ═══════════════════════════════════════════════════════════════════════════════
              PstI                                                        HindII
 881   CCTTTGGAGCTGCAGGGTGTGTTAGCAAACTACAGGACCAAATATCCTGCTCAAACTGTAACCCCAAAAATGCTACAGT
       ═══════════════════════════════════════════════════════════════════════════════
 961   TGACAGTCAGCAGATGAACACTGACCACAAGGCTGTTTTTGGATAAGGATAATGCTTATCCAGTGGAGTGCTGGGTTCCTG
       ═══════════════════════════════════════════════════════════════════════════════
```

FIG.10B

```
1041  ATCCAAGTAAAAATGAAAACACTAGATATTTGGAACCTACACAGGTGGGGAAAAATGTGCCTCCTGTTTTGCACATTACT
                                                                                  HindII
1121  AACACAGCAACCACAGTGCTTCTTGATGAGCAGGGTGTTGGGCCCTTGTGCAAAGCTGACAGCTTGTATGTTTCTGCTGT 1201  TGACATTTGTGGGCTGTTTACCAACACTTCTGGAACACAGCAGTGAAGGGACTTCCCAGATATTTTAAAATTACCCTTA 1281  GAAAGCGGTCTGTGAAAAACCCCTACCCAATTTCCTTTTGTTAAGTGACCTAATTAACAGGAGGACACAGAGGGTGGAT
                                                                              BamHI
1361  GGGCAGCCTATGATTGGAATGTCCTCTCAAGTAGAGGAGGTTAGGGTTTATGAGGACACAGAGGAGCTTCCTGGGATCC 1441  AGACATGATAAGATACATTGATGAGTTTGGACAAACCACAACTAGAATGCAGTGAAAAAAATGCTTTATTTGTGAAATTT
                                                           HindII
1521  GTGATGCTATGCTTTATTTGTAACCATTATAAGCTGCAATAAACAAGTTAACAACAACAATTGCATTCATTTTATGTTT 1601  CAGGTTCAGGGGGAGGTGTGGGAGGTTTTTTAAAGCAAGTAAAACCTCTACAAATGTGGTATGGCTGATTATGATCTTTG
```

1681 TGAAGGAACCTTACTTCTCTGTGGTGTGACATAATTGGACAAACTACCTACAGAGATTTAAAGCTCTAAGGTAAATATAAAA

1761 TTTTTAAGTGTATAATGTGTTAAACTACTGATTCTAATTGTTTGTGTATTTTAGATTCCAACCTATGGAACTGATGAATG

1841 GGAGCAGTGGTGGAATGCCTTTAATGAGGAAAACCTGTTTTTGCTCAGAAGAAATGCCATCTAGTGATGATGAGGCTACTG

1921 CTGACTCTCAACATTCTACTCCTCCAAAAAAAGAAGAAAGGTAGAGACCCCAAGGACTTTCCTTCAGAATTGCTAAGT

2001 TTTTGAGTCATGCTGTGTTTAGTAATAGAACTCTTGCTGTTTGCTATTTACACCACAAAGGAAAAAGCTGCACTGCT

2081 ATACAAGAAAATTATGGAAAAATATTCTGTAACCTTTATAAGTAGGCATAACAGTTATAATCATAACATACTGTTTTTC

2161 TTACTCCACACAGGCATAGAGTGTCTGCTATTAATAACATGCTCAAAAATTGTGTACCTTTAGCTTTTTAATTTGTAAA

2241 GGGGTTAATAAGGAATATTTGATGTATAGTGCCTTGACTAGAGATCCGCCTCCGGGCGAATTCTGCCATTCATCCGCTTA
                                                    ①

2321 TTATCACTTATTCAGGCGTAGCACCAGGCGTTTAAGGGCACCAATAACTGCCTTAAAAAAAATTACGCCCCGCCCTGCCAC

2401 TCATCGGCAGTGCTCTAGAACTAGTGGATCCCCCGGGCTGCAGGAATTCGATGATCCTCGGCCCTACCCACCGTACTC
     XbaI  SpeI BamHI SmaI  PstI  EcoRI  ①
                                         337◀···GlyGlyTyrGlu

FIG. 10E

```
2481 GTCAATTCCAAGGGCATCGGTAAACATCTGCTCAAACATCGGCCATATCCAGAGCGCCCTAGGGGGCGGAGTCGT
332► AspIleGlyLeuAlaAspThrPheMetGlnGluPheAspAlaMetAspLeuAlaGlyTyrProAlaSerAspHi
                                   SmaI
2561 GGGGGTAAATCCGGACCCGGGAATCCCCGTCCCCACAACATGTCCAGATCGAAATCGTCTAGGCGCTCGGCATGCCC
305► sProThrPheGlyProGlyProSerAspGlyProSerAspPheAspAspLeuAlaMetAspLeuAlaAspAlaHisAlaM
                                                                  HindII
                                                                  SalI
2641 ATCGCCAGTCGTCCGCGTCTAAGTGGAGCTCGTCCCCCAGGCTGACATCGGTCGGGGGGCCGTCGACAGTCTGCCGT
278► etAlaValAspIleArgProAlaThrProProAlaThrSerLeuArgArgThr
     SacII
2721 GTCTCCGGCGGGAGAAGGACAGGCCCGGAGCCGCCAGCCCCCTCTTCGGGGGCGTCGTCTCCGGAGATCGAGCA
252► HisGlyAlaProLeuPheSerLeuArgProAlaLeuGlyAlaAspAspProLeuAspLeuGluLe
2801 GGCCCTCGATGTAGACCCGTAATTGTTTTCGTACGGCGGCTGTACGCGGACCCACTTTCACATTTAAGTGTTTT
225► uGlyGluIleThrSerGlyTyrTyrAsnLysThrArgAlaArgSerGlySerGluCysLysLeuGlnLysG
      NdeI
2881 TCTAATCGCATATGATCAATTCAAGGCCCGAATAAGAAGGCTGGCTCTGCACCTTGGTGATCAAATAATTCGATAGCTTG
198► luLeuGlyCysIleIleLeuGluLeuGlyPheLeuPheAlaProGluAlaGlyGlnHisAspPheLeuGluIleAlaGln
2961 TCGTAATAATGCGGCCATACTACATCAGTACTAGCTGTTTCCCTTCTTCTTTACCGACTGATCGTCTTGATCTTCCAATA
172► ArgLeuLeuProProMetSerSerAspThrProProThrGlyArgGlyLysAlaValGlnLeuHisGlyGlnAspGluLeuVa
3041 CGCAACCTAAAGTAAAGTAAAATGCCCACAGCGGCTGAGTGCATATAATGCATTCTCTAGTGAAAAACCTTGTGGCATAAAAAG
145► lCysGlyLeuPheHisGlyValAlaSerLeuAlaTyrLeuAlaAsnGluLeuSerPheGlyGlnGlnCysLeuPheA
3121 GCTAATTGATTTTCGAGAGTTTCATACTGTTTTCTGTAGGCCGTACCTAAATGTACTTTTGCTCATGCGATGACT
118► laLeuGlnAsnGluLeuThrGluTyrGlnLysGlyLeuThrProArgThrGlyLeuHisValLysAlaGlyAspArgHisSer
3201 TAGTAAAGCACATCTAAAACATTTTACCGTTATTACCTAAAAATCTGCCAGCTTCCCCTTCTAAAGGCCAAAACTGAC
92► LeuLeuAlaCysArgPheSerLysAlaAsnArgLeuPheAspGlnTrpProSerGlyLeuProCysPheHisTh
3281 TATGTGCCTATCTAACATCTCAATGGCGTGAGCAAAGCCCGCTTATTTTTACATGCCAATACAATGTAGCC
65► rHisHisArgAspLeuMetGlnIleIleAlaLeuAlaAspLeuGluAlaGlnAspArgLysAsnLysValHisTrpTyrLeuThrProG
```

FIG. 10F

```
3361 TGCTCTACACCTAGCTTCTGGGCCAGTTTACGGGTTGTTAAACCTTCGATTCCGACCTCATTAAGCAGCTCTAATGCGCT
  38► lnGluValGlyLeuLysGlnAlaLeuLysThrLeuGlyThrThrLeuGlyllelleGlyValGlyAsnLeuLeuGluLeuAlaSer
                              Xbal  Ncol       HindIII ClaI    Sall         XbaI BamHI
                                                           HindII ⓘ
3441 GTTAATCACTTTACTTTTATCTAGAAGCCATGGTGGCAAGCTTATCGATACCGTCGACTCGAGGATC
  12► AsnIleValLysSerLysAspLeuArgSerAlaⓂet ← START OF tTAᵏ
                Smal    SacI EcoRI
3521 CCCGGGTACCGAGCTCGAATTCGGGCCCCGGGAGCCTGGATCGGTCCCCGGTGTCTTCTTCATGGAGGTCAAAACAGGCTGGA
                                                                                   ▲ Smal
                                                                           SacI
3601 TGGGCTCTCCAGGGCATCGACGGTCACTAAACGAGCTCTGCTTATATAGGCCTCCCACCGTACACGCCTACTCGACCC
3681 GGGTACCGAGCTCGACTTTCACTTTTCTCTATCACTGATAGGGAGTGGTAAACTCGACTTTCACTTTTCTCTATCACTGA
          SacI
           ↓
3761 TAGGGAGTGGTAAACTCGACTTTCACTTTTCTCTATCACTGATAGGGAGTGGTAAACTCGACTTTCACTTTTCTCTATCA
3841 CTGATAGGGAGTGGTAAACTCGACTTTCACTTTTCTCTATCACTGATAGGGAGTGGTAAACTCGAGTTTCACTTTTCTCT
                                                                         Xhol
3921 ATCACTGATAGGGAGTGGTAAACTCGACTTTCACTTTTCTCTATCACTGATAGGGAGTGGTAAACTCGAGGGGGGGCCCG
           BssH II
4001 GTACCCAGCTTTGTTCCCTTTAGTGAGGGTTAATGCGCGCTTGGCGTAATCATGGTCATAGCTGTTTCCTGTGTGAAA
4081 TTGTTATCCGCTCACAATTCCACACAACATACGAGCCGGAAGCATAAAGTGTAAAGCCTGGGGTGCCTAATGAGTGAGCT
                                                                         PvuI
4161 AACTCACATTAATTGCGTTGCGCTCACTGCCCGCTTTCCAGTCGGGAAACCTGTCGTGCCAGCTGCATTAATGAATCGGC
4241 CAACGCGCGGGGAGAGGCGGTTTGCGTATTGGGCGCTCTTCCGCTTCCTCGCTCACTGACTCGCTGCGCTCGGTCGTTCG
4321 GCTGCGGCGAGCGGTATCAGCTCACTCAAAGGCGGTAATACGGTTATCCACAGAATCAGGGGATAACGCAGGAAAGAACA
4401 TGTGAGCAAAAGGCCAGCAAAAGGCCAGGAACCGTAAAAAGGCCGCGTTGCTGGCGTTTTTCCATAGGCTCCGCCCCCT
4481 GACGAGCATCACAAAAATCGACGCTCAAGTCAGAGGTGGCGAAACCCGACAGGACTATAAAGATACCAGGCGTTTCCCCC
```

FIG. 10G

```
4561  TGAAGCTCCCCTCGTGCGGCTCTCCTGTGTCCGACCCTGCCCCTGCCCCTTACCGGATACCTGTCGCCTTTCTCTCCTTCGGGAAGCC
4641  TGGGCTTTCTCATAGCTCACGCTGTAGGTATCTCAGTTCGGTGTAGGTCGTTCGCTCCAAGCTGGGCTGTGCACGAA
4721  CCCCCGTTCAGCCGGTTCAGCCCCGACCGGTGCCCTTATCCGGTAACTATCGTCTGAGTCCAACCCGGTAACGACACGACTATCGCC
4801  ACTGGCAGCAGCCACTGTAACAGGATTAGCAGAGCGAGGTATGTAGCGGTGCTACAGAGTTCTTGAAGTGTGGCCTA
4881  ACTACGGCTACACTAGAAGGACACAGTATTGGTATCTGCCCTCTGCTGAAGCCAGTTACCTTCGGAAAAAGAGTTGGTAGC
4961  TCTTGATCCGGCAAACAAACCACCGCTGTAGCCGGTGGTTTTTGTTGCAAGCAGCAGATTACCGCGCAGAAAAAAGG
5041  ATCTCAAGAAGATCCTTTGATCTTTTCTACGGGCTCGACGCTCAGTGGAACGAAAACTCACGTTAAGGATTTTGGTCA
5121  TGAGATTATCAAAAAGGATCTTCACCTAGATCCTTTTAAATAAAATGAAGTTTAAATCAATCTAAAGTATATATGAG
5201  TAAACTTGGTCTGACAGTTACCAATGCTTAATCAGTGAGGCACCTATCTCAGCGATCTGTCTATTCGTTCATCCATAGT
5281  TGCCTGACTCCCCGTCGTGTAGATAACTACGATACGGGAGGGCTTACATCTGCCCCAGTGCTGCAATGATACCGCGAG
5361  ACCCACGCTCACCGGCTCCAGATTTATCAGCAATAAACCAGCCAGCCGGAAGGGCGAGCGCAGAAGTGGTCCTGCAACT
5441  TTATCCGCCTCCATCCAGTCTATTAATTGTGCCGGGAAGCTAGAGTAAGTAGTTCGCCAGTTAATAGTTTGCGCAACGT
5521  TGTTGCCATTGCTACAGGCATCGTGGTGTCAAACGCTCGTCGTTGGTATGGCCTTCATTCAGCTCCGGTTCCCAACGATCAA
                                                                              PvuI
5601  GGCGAGTTACATGATCCCCATGTTGTGCAAAAAAGCGGTTAGCTCCTTCGGTCCTCCGATCGTTGTCAGAAGTAAGTTG
5681  GCCGCAGTGTTATCACTCATGGTTATGGCAGCACTGCCATAATTCTCTTACTGTCATGCCATCCGTAAGATGCTTTTCTGT
           ScaI                                                                    XmnI
5761  GACTGGTGAGTACTCAACCAAGTCATTCTGAGAATAGTGTATGCGGCGACCGAGTTGCTCTTGCCCGGCGTCAATACGGG
5841  ATAATACCGCGCCACATAGCAGAACTTTAAAAGTGCTCATCATTGGAAACGTTCTTCGGGGCGAAAACTCTCAAGGATC
5921  TTACCGCTGTTGAGATCCAGTTCGATGTAACCCACTCGTGCACCCAACTGATCTTCAGCATCTTTTACTTTCACCAGCGT
6001  TTCTGGGTGAGCAAAAACAGGAAGGCAAATGCCGCAAAAAAGGGAATAAGGGCGACACGGAAATGTTGAATACTCATAC
         SspI
6081  TCTTCCTTTTTCAATATTATTGAAGCATTTATCAGGGTTATTGTCTCATGAGCGGATACATATTTGAATGTATTTAGAAA
6161  AATAAACAAATAGGGGTTCCGCGCACATTTCCCCGAAAAGTGCCAC
```

```
      XhoI
  1   CTCGAGGAGC TTGGCCCATT GCATACGGTTG TATCCATATC ATAATATGTA CATTTATATT GGCTCATGTC
              HindII
 71   CAACATTACC GCCATGTTGA CATTGATTAT TGACTAGTTA TTAATAGTAA TCAATTACGG GGTCATTAGT 141   TCATAGCCCA TATATGGAGT TCCGGGTTAC ATAACTTACG GTAAATGGCC CGCCTGGCTG ACCGCCCAAC 211   GACCCCCGCC CATTGACGTC AATAATGACG TATGTTCCCA TAGTAACGCC AATAGGGACT TTCCATTGAC
                                                                       NdeI
281   GTCAATGGGT GGAGTATTTA CGCTAAACTG CCCACTTGGC AGTACATCAA GTGTATCATA TGCCAAGTAC 351   GCCCCCTATT GACGTCAATG ACGGTAAATG GCCCGCCTGG CATTATGCCC AGTACATGAC CTTATGGGAC
                                    NcoI
421   TTTCCTACTT GGCAGTACAT CTACGTATTA GTCATCGCTA TTACCATGGT GATGCGGTTT TGGCAGTACA 491   TCAATGGGCG TGGATAGCGG TTTGACTCAC GGGGATTTCC AAGTCTCCAC CCCATTGACG TCAATGGGAG 561   TTTGTTTTGG CACCAAAATC AACGGGACTT TCCAAAATGT CGTAACAACT CCGCCCCATT GACGCAAATG
                   SacI
631   GGCGGTAGGC GTGTACGGTG GGAGGTCTAT ATAAGCAGAG CTCGTTTAGT GAACCGTCAG ATCGCCTGGA
                                                                       SacII    EcoRI
701   GACGCCATCC ACGCTGTTTT GACCTCCATA GAAGACACCG GGACCGATCC AGCCTCCGCG GCCCGAATT
                                                                            ▲
      NdeI
771   CAT
```

FIG. 11B

```
      XbaI
774 ATG TCT AGA TTA GAT AAA AGT AAA GTG ATT AAC AGC GCA TTA GAG CTG CTT AAT GAG GTC
  1►Met Ser Arg Leu Asp Lys Ser Lys Val Ile Asn Ser Ala Leu Glu Leu Leu Asn Glu Val
834 GGA ATC GAA GGT TTA ACA ACC CGT AAA CTC GCC CAG AAG CTA GGT GTA GAG CAG CCT ACA
 21►Gly Ile Glu Gly Leu Thr Thr Arg Lys Leu Ala Gln Lys Leu Gly Val Glu Gln Pro Thr
894 TAT TGG CAT GTA AAA AAT AAG CGG GCT TTG CTC GAC GCC TTA GCC ATT GAG ATG TTA
 41►Leu Tyr Trp His Val Lys Asn Lys Arg Ala Leu Leu Asp Ala Leu Ala Ile Glu Met Leu
954 GAT AGG CAC CAT ACT CAC TTT TGC CCT TTA GAA GGG GAA AGC TGG CAA GAT TTT TTA CGT
 61►Asp Arg His His Thr His Phe Cys Pro Leu Glu Gly Glu Ser Trp Gln Asp Phe Leu Arg
1014 AAT AAC GCT AAA AGT TTT AGA TGT GCT TTA CTA TTA GAA ACT CTC AGT GAT GGA GCA AAA GTA CAT
 81►Asn Asn Ala Lys Ser Phe Arg Cys Ala Leu Leu Leu Glu Thr His Arg Asp Gly Ala Lys Val His
1074 TTA GGT ACA CGG CCT ACA GAA AAA CAG TAT GAA ACT CTC GAA AAT CAA TTA GCC TTT TTA
101►Leu Gly Thr Arg Pro Thr Glu Lys Gln Tyr Glu Thr Leu Glu Asn Gln Leu Ala Phe Leu
1134 TGC CAA CAA GGT TTT TCA GAG AAT GCA TTA TAT GCA CTC AGC GCT GTG GGG CAT TTT
121►Cys Gln Gln Gly Phe Ser Glu Asn Ala Leu Tyr Ala Leu Ser Ala Val Gly His Phe
1194 ACT TTA GGT TGC GTA TTG GAA GAT CAA GAG CAT CAA GTC GCT AAA GAA GAA AGG GAA ACA
141►Thr Leu Gly Cys Val Leu Glu Asp Gln Glu His Gln Val Ala Lys Glu Glu Arg Glu Thr
1254 CCT ACT ACT GAT AGT ATG CCG CCA TTA TTA CGA CAA GCT ATC GAA TTT GAT CAC CAA
161►Pro Thr Thr Asp Ser Met Pro Pro Leu Leu Arg Gln Ala Ile Glu Phe Asp His Gln
                                                                          NdeI
1314 GGT GCA GAG CCA GCC TTC TTA TTC GGC CTT GAA TTG ATC ATA TGC GGA TTA GAA AAA CAA
181►Gly Ala Glu Pro Ala Phe Leu Phe Gly Leu Glu Leu Ile Ile Cys Gly Leu Glu Lys Gln
```

FIG. 11C

```
1374 CTT AAA TGT GAA AGT GGG TCC GCG TAC AGC CGC GCG CGT ACG AAA AAC AAT TAC GGG TCT
 201►Leu Lys Cys Glu Ser Gly Ser Ala Tyr Ser Arg Ala Arg Thr Lys Asn Asn Tyr Gly Ser
1434 ACC ATC GAG GGC CTG CTC GAT CTC CCG GAC GAC GCC CCC GAA GAG GCG GGG CTG GCG
 221►Thr Ile Glu Gly Leu Leu Asp Leu Pro Asp Asp Ala Pro Glu Glu Ala Gly Leu Ala
                                                                HindII
                                                                 SalI
1494 GCT CCG CGC CTG TCC TTT CTC CCC GCG GGA CAC ACG CGC AGA CTG TCG ACG GCC CCC CCG
 241►Ala Pro Arg Leu Ser Phe Leu Pro Ala Gly His Thr Arg Arg Leu Ser Thr Ala Pro Pro
             SacII
              SacI                                                           SmaI
1554 ACC GAT GTC AGC CTG GGG GAC GAG CTC CAC TTA GAC GGC GAG GAC GTG GCG ATG GCG CAT
 261►Thr Asp Val Ser Leu Gly Asp Glu Leu His Leu Asp Gly Glu Asp Val Ala Met Ala His
1614 GCC GAC GCG CTA GAC GAT TTC GAT CTG GAC ATG TTG GGG GAC GGG GAT TCC CCG GGT CCG
 281►Ala Asp Ala Leu Asp Asp Phe Asp Leu Asp Met Leu Gly Asp Gly Asp Ser Pro Gly Pro
1674 GGA TTT ACC CCC CAC GAC TCC GCC CCC TAC GGC GCT CTG GAT ATG GCC GAC TTC GAG TTT
 301►Gly Phe Thr Pro His Asp Ser Ala Pro Tyr Gly Ala Leu Asp Met Ala Asp Phe Glu Phe
       BamHI
1734 GAG CAG ATG TTT ACC GAT GCC CTT GGA ATT GAC GAG TAC GGT GGG TAG
 321►Glu Gln Met Phe Thr Asp Ala Leu Gly Ile Asp Glu Tyr Gly Gly •••
1782 GGGGCGGCGAG GATCCAGACA TGATAAGATA CATTGATGAG TTTGGACAAA CCACAACTAG AATGCAGTGA
1852 AAAAAATGCT TTATTTGTGA AATTTGTGAT GCTATTGCTT TATTTGTAAC CATTATAAGC TGCAATAAAC
      HindII
1922 AAGTTAACAA CAACAATTGC CTCTACAAAT GTGGTATGGC TGATTATGAT TCAGGGGAG GTGTGGGAGG TTTTTTAAAG
1992 CAAGTAAAAC CTCTACAAAC GTGGTATGGC TGATTATGAT CCTGCAAGCC TCGTCGTCTG GCCGGACCAC
2062 GCTATCTGTG CAAGGTCCCC GGACGCGCGC TCCATGAGCA GAGCGCCCGC CGCCGAGGCA AGACTCGGGC
```

FIG. 11D

```
                                HindII
2132 GGCGCCCTGC CCGTCCCACC AGGTCAACAG GCGGTAACCG GCCTCTTCAT CGGGAATGCG CGGGACCTTC
                                                          HindIII
2202 AGCATCGCCG GCATGTCCCC TGGGGACGG GAAGTATCAG CTCGACCAAG CTTGGGGAGA TTTTCAGGAG
2272 CTAAGGAAGC TAAAATGGAG AAAAAAATCA CTGGATATAC CACCGTTGAT ATATCCCAAT GGCATCGTAA
                                                                    PvuII
2342 AGAACATTTT GAGGCATTTC AGTCAGTTGC TCAATGTACC TATAACCAGA CCGTTCAGCT GCATTAATGA
2412 ATCGGCCAAC GCGCGGGGAG AGGGGGTTTG CGTATTGGGC GCTCTTCCGC TTCCTCGCTC ACTGACTCGC
2482 TGCGCTCGGT CGTTCGGCTG CGGCGAGCGG TATCAGCTCA CTCAAAGGCG GTAATACGGT TATCCACAGA
2552 ATCAGGGGAT AACGCAGGAA AGAACATGTG AGCAAAAGGC CAGCAAAAGG CCAGGAACCG TAAAAAGGCC
2622 GCGTTGCTGG CGTTTTTCCA TAGGCTCCGC CCCCCTGACG AGCATCACAA AAATGACGC TCAAGTCAGA
2692 GGTGGCGAAA CCCGACAGGA CTATAAAGAT ACCAGGCGTT TCCCCCTGGA AGCTCCCTCG TGCGCTCTCC
2762 TGTTCCGACC CTGCCGCTTA CCGGATACCT GTCCGCCTTT CTCCCTTCGG GAAGCGTGGC GCTTTCTCAA
2832 TGCTCACGCT GTAGGTATCT CAGTTCGGTG TAGGTCGTTC GCTCCAAGCT GGGCTGTGTG CACGAACCCC
2902 CCGTTCAGCC CGACCGCTGC GCCTTATCCG GTAACTATCG TCTTGAGTCC AACCCGGTAA GACACGACTT
2972 ATCGCCACTG GCAGCAGCCA CTGGTAACAG GATTAGCAGA GCGAGGTATG TAGGCGGTGC TACAGAGTTC
3042 TTGAAGTGGT GGCCTAACTA CGGCTACACT AGAAGGACAG TATTTGGTAT CTGCGCTCTG CTGAAGCCAG
3112 TTACCTTCGG AAAAAGAGTT GGTAGCTCTT GATCCGGCAA ACAAACCACC GCTGGTAGCG GTGGTTTTTT
3182 TGTTTGCAAG CAGCAGATTA CGCGCAGAAA AAAAGGATCT CAAGAAGATC CTTTGATCTT TTCTACGGGG
3252 TCTGACGCTC AGTGGAACGA AAACTCACGT TAAGGGATTT TGGTCATGAG ATTATCAAAA AGGATCTTCA
3322 CCTAGATCCT TTTAAATTAA AAATGAAGTT TTAAATCAAT CTAAAGTATA TATGAGTAAA CTTGGTCTGA
3392 CAGTTACCAA TGCTTAATCA GTGAGGCACC TATCTCAGCG ATCTGTCTAT TTCGTTCATC CATAGTTGCC
3462 TGACTCCCCG TCGTGTAGAT AACTACGATA CGGGAGGGCT TACCATCTGG CCCCAGTGCT GCAATGATAC
3532 CGCGAGACCC ACGCTCACCG GCTCCAGATT TATCAGCAAT AAACCAGCCA GCCGGAAGGG CCGAGCGCAG
3602 AAGTGGTCCT GCAACTTTAT CCGCCTCCAT CCAGTCTATT AATTGTTGCC GGGAAGCTAG AGTAAGTAGT
3672 TCGCCAGTTA ATAGTTTGCG CAACGTTGTT GCCATTGCTA CAGGCATCGT GGTGTCACGC TCGTCGTTTG
```

FIG. 11E

```
3742 GTATGGCTTC ATTCAGCTCC GGTTCCCAAC GATCAAGGCG AGTTACATGA TCCCCCATGT TGTGCAAAAA
3812 AGCGGGTTAGC TCCTTCGGTC CTCCGATCGT TGTCAGAAGT AAGTTGGCCG CAGTGTTATC ACTCATGGT
                                                                         ScaI
3882 ATGGCAGCAC TGCATAAATTC TCTTACTGTC ATGCCATCCG TAAGATGCTT TTCTGTGACT GGTGAGTACT
3952 CAACCAAGTC ATTCTGAGAA TAGTGTATGC GGCGACCGAG TTGCTCTTGC CCGGCGTCAA TACGGGATAA
4022 TACCGCGCCA CATAGCAGAA CTTTAAAAGT GCTCATCATT GGAAAACGTT CTTCGGGGCG AAAACTCTCA
4092 AGGATCTTAC CGCTGTTGAG ATCCAGTTCG ATGTAACCCA CTCGTGCACC CAACTGATCT TCAGCATCTT
4162 TTACTTTCAC CAGGGTTTCT GGGTGAGCAA AAACAGGAAG GCAAAATGCC GCAAAAAAGG GAATAAGGGC
4232 GACACGGAAA TGTTGAATAC TCATACTCTT CCTTTTTCAA TATTATTGAA GCATTTATCA GGGTTATTGT
4302 CTCATGAGCG GATACATATT TGAATGTATT TAGAAAAATA AACAAATAGG GGTTCCGCGC ACATTTCCCC
4372 GAAAAGTGCC ACCTGACGTC TAAGAAACCA TTATTATCAT GACATTAACC TATAAAAATA GGCGTATCAC
4442 GAGGCCCTTT CGTC
```

FIG. 11F

```
      EcoRI XhoI
  1 GAATTCCTCG AGTTTACCAC TCCCTATCAG TGATAGAGAA AAGTGAAAGT CGAGTTTACC ACTCCCTATC

71 AGTGATAGAG AAAAGTGAAA GTCGAGTTTA CCACTCCCTA TCAGTGATAG AGAAAAGTGA AAGTCGAGTT

141 TACCACTCCC TATCAGTGAT AGAGAAAAGT GAAAGTCGAG TTTACCACTC CCTATCAGTG ATAGAGAAAA

211 GTGAAAGTCG AGTTTACCAC TCCCTATCAG TGATAGAGAA AAGTGAAAGT CGAGTTTACC ACTCCCTATC

281 AGTGATAGAG AAAAGTGAAA GTCGAGCTCG GTACCCGGGT CGAGTAGGCG TGTACGGTGG GAGGCCTATA

351 TAAGCAGAGC TCGTTTAGTG AACCGTCAGA TCGCCTGGAG ACGGCCATCC ACGCTGTTTG ACCTCCATAG
                                                     EcoRI      XbaI  SalI
421 AAGACACCGG GACCGGATCCA GCCTCCGCGG CCCCGAATTC GAGCTCGGTA CCCGGGGATC CTCTAGAGTC
491 GACCTGCAGG C
         HindIII 502 ATG CAA GCT TGG CAT TCC GGT ACT GTT GGT AAA ATG GAA GAC GCC AAA AAC ATA AAG AAA
  1►Met Gln Ala Trp His Ser Gly Thr Val Gly Lys Met Glu Asp Ala Lys Asn Ile Lys Lys
                                          XbaI
562 GGC CCG GCG CCA TTC TAT CCT CTA GAG GAT GGA ACC GCT GGA GAG CAA CTG GAT AAG CCT
 21►Gly Pro Ala Pro Phe Tyr Pro Leu Glu Asp Gly Thr Ala Gly Glu Gln Leu Asp Lys Pro
622 ATG AAG AGA TAC GCC CTG GTT CCT GGA ACA ATT GCT TTT ACA GAT GCA CAT GCA GAG GTG
 41►Met Lys Arg Tyr Ala Leu Val Pro Gly Thr Ile Ala Phe Thr Asp Ala His Ala Glu Val
682 AAC ATC ACG TAC GCG GAA TAC TTC GAA ATG TCC GTT CGG TTG GCA GAA GCT GTG AAA CGA
 61►Asn Ile Thr Tyr Ala Glu Tyr Phe Glu Met Ser Val Arg Leu Ala Glu Ala Val Lys Arg
```

FIG. 12B

```
 742 TAT GGG CTG AAT ACA AAT CAC AGA ATC GTC GTA TTC AGT GAA AAC TCT CTT CAA TTC TTT
  81►Tyr Gly Leu Asn Thr Asn His Arg Ile Val Val Phe Ser Glu Asn Ser Leu Gln Phe Phe
 802 ATG CCG GTG TTG GGC GCG TTA TTT ATC GGA GTT GCA GTT GCG CCC GCG AAC GAC ATT TAT
 101►Met Pro Val Leu Gly Ala Leu Phe Ile Gly Val Ala Val Ala Pro Ala Asn Asp Ile Tyr
 862 AAT GAA CGT GAA TTG CTC AAC AGT ATG AAC ATT TCG CAG CCT AAC GTA GTG TTG GTT TCC
 121►Asn Glu Arg Glu Leu Leu Asn Ser Met Asn Ile Ser Gln Pro Asn Val Val Leu Val Ser
 922 AAA AAG GGG TTG CAA AAA ATT TTG AAC GTG CAA AAA TTA CCA ATA ATC CAG AAA ATT
 141►Lys Lys Gly Leu Gln Lys Ile Leu Asn Val Gln Lys Lys Leu Pro Ile Ile Gln Lys Ile
 982 ATT ATC ATG GAT CTC AAA ACG GAT TAC CAG GGA TTT CAG TCG ATG TAC ACG TTC GTC ACA
 161►Ile Ile Met Asp Leu Lys Thr Asp Tyr Gln Gly Phe Gln Ser Met Tyr Thr Phe Val Thr
1042 TCT CAT CTA CCT CCC GGT TTT AAT GAA TAC GAT TTT GTA CCA GAG TCC TTT GAT CGT GAC
 181►Ser His Leu Pro Pro Gly Phe Asn Glu Tyr Asp Phe Val Pro Glu Ser Phe Asp Arg Asp
                                          EcoRI
1102 AAA ACA ATT GCA CTG ATA ATG AAT TCC TCT GGA TCT ACT GGG TTA CCT AAG GGT GTG GCC
 201►Lys Thr Ile Ala Leu Ile Met Asn Ser Ser Gly Ser Thr Gly Leu Pro Lys Gly Val Ala
1162 CTT CCG CAT AGA ACT GCC TGC GTC AGA TTC TCG CAT GCC AGA GAT CCT ATT TTT GGC AAT
 221►Leu Pro His Arg Thr Ala Cys Val Arg Phe Ser His Ala Arg Asp Pro Ile Phe Gly Asn
1222 CAA ATC ATT CCG GAT ACT GCG ATT TTA AGT GTT CCA TTC CAT CAC GGT TTT GGA ATG
 241►Gln Ile Ile Pro Asp Thr Ala Ile Leu Ser Val Pro Phe His His Gly Phe Gly Met
1282 TTT ACT ACA CTC GGA TAT TTG ATA TGT GTC CGA GTC GTC TTA ATG TAT AGA TTT GAA
 261►Phe Thr Thr Leu Gly Tyr Leu Ile Cys Val Arg Val Val Leu Met Tyr Arg Phe Glu
1342 GAA GAG CTG TTT TTA CGA TCC CTT CAG GAT TAC AAA ATT CAA AGT GCG TTG CTA GTA CCA
 281►Glu Glu Leu Phe Leu Arg Ser Leu Gln Asp Tyr Lys Ile Gln Ser Ala Leu Leu Val Pro
1402 ACC CTA TTT TCA TTC GCC AAA AGC ACT CTG ATT GAC AAA TAC GAT TTA TCT AAT TTA
 301►Thr Leu Phe Ser Phe Ala Lys Ser Thr Leu Ile Asp Lys Tyr Asp Leu Ser Asn Leu
```

FIG. 12C

```
1462 CAC GAA ATT GCT TCT GGG GGC GCA CCT CTT TCG AAA GAA GTC GGG GAA GCG GTT GCA AAA
 321►His Glu Ile Ala Ser Gly Gly Ala Pro Leu Ser Lys Glu Val Gly Glu Ala Val Ala Lys
1522 CGC TTC CAT CTT CCA GGG ATA CGA CAA GGA TAT GGG CTC ACT GAG ACT ACA TCA GCT ATT
 341►Arg Phe His Leu Pro Gly Ile Arg Gln Gly Tyr Gly Leu Thr Glu Thr Thr Ser Ala Ile
1582 CTG ATT ACA CCC GAG GGG GAT GAT AAA CCG GGC GTC GGT AAA GTT GTT CCA TTT TTT
 361►Leu Ile Thr Pro Glu Gly Asp Asp Lys Pro Gly Val Gly Lys Val Val Pro Phe Phe
1642 GAA GCG AAG GTT GTG GAT CTG GAT ACC GGG AAA ACG CTG GGC GTT AAT CAG AGA GGC GAA
 381►Glu Ala Lys Val Val Asp Leu Asp Thr Gly Lys Thr Leu Gly Val Asn Gln Arg Gly Glu
1702 TTA TGT GTC AGA GGA CCT ATG ATG TCC GGT TAT GTA AAC AAT CCG CAA GCG ACC AAC
 401►Leu Cys Val Arg Gly Pro Met Met Ser Gly Tyr Val Asn Asn Pro Gln Ala Thr Asn
1762 GCC TTG ATT GAC AAG GAT TGG CTA CAT TCT GGA GAC ATA GCT TAC TGG GAC GAA GAC
 421►Ala Leu Ile Asp Lys Asp Trp Leu His Ser Gly Asp Ile Ala Tyr Trp Asp Glu Asp
1822 CAC TTC TTC ATA GTT GAC CGC TTG AAG TCT TTA ATT AAA GGA TAT AAA TAC CAG GTG
 441►His Phe Phe Ile Val Asp Arg Leu Lys Ser Leu Ile Lys Tyr Lys Gly Tyr Gln Val
1882 GCC CCC GCT GAA TTG GAA TCG ATA TTG TTA CAA CAC CCC AAC ATC TTC GAC GCG GGC GTG
 461►Ala Pro Ala Glu Leu Glu Ser Ile Leu Leu Gln His Pro Asn Ile Phe Asp Ala Gly Val
1942 GCA GGT CTT CCC GAC GAT GCC GGT GAA CTT CCC GCC GCC GTT GTT TTG GAG CAC
 481►Ala Gly Leu Pro Asp Asp Ala Gly Glu Leu Pro Ala Ala Val Val Leu Glu His
2002 GGA AAG ACG ATG GAA GAT ACG GAG ATC GTG GAT TAC GTC GCC AGT CAA GTA ACA ACC GCC
 501►Gly Lys Thr Met Glu Asp Thr Glu Ile Val Asp Tyr Val Ala Ser Gln Val Thr Thr Ala
2062 AAA AAG TTG CGC GGA GGA GTT GTG TTT GTG GAC GAA GTA CCG AAA GGT CTT ACC GGA AAA
 521►Lys Lys Leu Arg Gly Gly Val Val Phe Val Asp Glu Val Pro Lys Gly Leu Thr Gly Lys
2122 CTC GAC GCA AGA AAA ACT AGA GAG ATC CTC ATA AAG GCC GGA AAG TCC AAA
 541►Leu Asp Ala Arg Lys Thr Arg Glu Ile Leu Ile Lys Ala Lys Gly Lys Ser Lys
2182 TTG TAA
 561►Leu
```

FIG. 12D

```
                                                              XbaI
2188  AATGTAACTG TATTCAGCGA TGACGAAATT CTTAGCTATT GTAATGACTC TAGAGGATCT TTGTGAAGGA
2258  ACCTTACTTC TGTGGTGTGA CATAATTGGA CAAACTACCT ACAGAGATTT AAAGCTCTAA GGTAAATATA
2328  AAATTTTTAA GTGTATAATG TGTTAAACTA CTGATTCTAA TTGTTTGTGT ATTTTAGATT CCAACCTATG
2398  GAACTGATGA ATGGGAGCAG TGGTGGAATG CCTTTAATGA GGAAAACCTG TTTTGCTCAG AAGAAATGCC
2468  ATCTAGTGAT GATGAGGCTA CTGCTGACTC TCAACATTCT ACTCCTCCAA AAAAGAAGAG AAAGGTAGAA
2538  GACCCCAAGG ACTTTCCTC AGAATTGCTA AGTTTTTTGA GTCATGCTGT GTTAGTAAT AGAACTCTTG
2608  CTTGCTTTGC TATTTACACC ACAAAGGAAA AAGCTGCACT GCTATACAAG AAAATTATGG AAAAATATTC
2678  TGTAACCTTT ATAAGTAGGC ATAACAGTTA TAATCATAAC ATACTGTTTT TTCTTACTCC ACACAGGCAT
2748  AGAGTGTCTG CTATTAATAA CTATGCTCAA AAATTGTGTA CCTTTAGCTT TTTAATTTGT AAAGGGTTA
2818  ATAAGGAATA TTTGATGTAT AGTGCCTTGA TCATAATCAG CCATACCACA TTTGTAGAGG TTTTACTTGC
2888  TTTAAAAAAC CTCCCACACC TCCCCTGAA CCTGAAACAT AAAATGAATG CAATTGTTGT TGTTAACTTG
2958  TTTATTGCAG CTTATAATGG TTACAAATAA AGCAATAGCA TCACAAATTT CACAAATAAA GCATTTTTTT
                                                           XbaI
3028  CACTGCATTC TAGTTGTGGT TTGTCCAAAC TCATCAATGT ATCTTATCAT GTCTGCCTCT AGAGCTGCAT
3098  TAATGAATCG GCCAACGCGC GGGGAGAGGC GGTTTGCGTA TTGGGCGCTC TTCCGCTTCC TCGCTCACTG
3168  ACTCGCTGCG CTCGGTCGTT CGGCTGCGGC GAGCGGTATC AGCTCACTCA AAGGCGGTAA TACGGTTATC
3238  CACAGAATCA GGGGATAACG CAGGAAAGAA CATGTGAGCA AAAGGCCAGC AAAAGGCCAG GAACCGTAAA
3308  AAGGCCGCGT TGCTGGCGTT TTTCCATAGG CTCCGCCCCC CTGACGAGCA TCACAAAAAT CGACGCTCAA
3378  GTCAGAGGTG GCGAAACCCG ACAGGACTAT AAAGATACCA GGCGTTTCCC CCTGGAAGCT CCCTCGTGCG
3448  CTCTCCTGTT CCGACCCTGC CGCTTACCGG ATACCTGTCC GCCTTTCTCC CTTCGGGAAG CGTGGCGCTT
3518  TCTCAATGCT CACGCTGTAG GTATCTCAGT TCGGTGTAGG AGTCCACTCA CGAACCGGCT TGTGTGCACG
3588  AACCCCCCGT TCAGCCCGAC CGCTGCGCCT TATCCGGTAA CTATCGTCTT GAGTCCAACC CGGTAAGACA
3658  CGACTTATCG CCACTGGCAG CAGCCACTGG TAACAGGATT AGCAGAGCGA GGTATGTAGG CGGTGCTACA
3728  GAGTTCTTGA AGTGGTGGCC TAACTACGGC TACACTAGAA GGACAGTATT TGGTATCTGC GCTCTGCTGA
3798  AGCCAGTTAC CTTCGGAAAA AGAGTTGGTA GCTCTTGATC GCTCAAACAA ACCACCGCTG GTAGCGGTGG
```

FIG. 12E

```
3868  TTTTTTTGTT TGCAAGCAGC AGATTACGCG CAGAAAAAAA GGATCTCAAG AAGATCCTTT GATCTTTTCT
3938  ACGGGGTCTG ACGCTCAGTG GAACGAAAAC TCACGTTAAG GGATTTTGGT CATGAGATTA TCAAAAAGGA
4008  TCTTCACCTA GATCCTTTTA AATTAAAAAT GAAGTTTTAA ATCAATCTAA AGTATATATG AGTAAACTTG
4078  GTCTGACAGT TACCAATGCT TAATCAGTGA GGCACCTATC TCAGCGATCT GTCTATTTCG TTCATCCATA
4148  GTTGCCTGAC TCCCCGTCGT GTAGATAACT ACGATACGGG AGGGCTTACC ATCTGGCCCC AGTGCTGCAA
4218  TGATACCGCG AGACCCACGC TCACCGGCTC CAGATTTATC AGCAATAAAC CAGCCAGCCG GAAGGGCCGA
4288  GCGCAGAAGT GGTCCTGCAA CTTTATCCGC CTCCATCCAG TCTATTAATT GTTGCCGGGA AGCTAGAGTA
4358  AGTAGTTCGC CAGTTAATAG TTTGCGCAAC GTTGTTGCCA TTGCTACAGG CATCGTGGTG TCACGCTCGT
4428  CGTTTGGTAT GGCTTCATTC AGCTCCGGTT CCCAACGATC AAGGCGAGTT ACATGATCCC CCATGTTGTG
4498  CAAAAAAGCG GTTAGCTCCT TCGGTCCTCC GATCGTTGTC AGAAGTAAGT TGGCCGCAGT GTTATCACTC
4568  ATGGTTATGG CAGCACTGCA TAATTCTCTT ACTGTCATGC CATCCGTAAG ATGCTTTTCT GTGACTGGTG
4638  AGTACTCAAC CAAGTCATTC TGAGAATAGT GTATGCGGCG ACCGAGTTGC TCTTGCCCGG CGTCAATACG
4708  GGATAATACC GCGCCACATA GCAGAACTTT AAAAGTGCTC ATCATTGGAA AACGTTCTTC GGGGCGAAAA
4778  CTCTCAAGGA TCTTACCGCT GTTGAGATCC AGTTCGATGT AACCCACTCG TGCACCCAAC TGATCTTCAG
4848  CATCTTTTAC TTTCACCAGC GTTTCTGGGT GAGCAAAAAC AGGAAGGCAA AATGCCGCAA AAAAGGGAAT
4918  AAGGGCGACA CGGAAATGTT GAATACTCAT ACTCTTCCTT TTTCAATATT ATTGAAGCAT TTATCAGGGT
4988  TATTGTCTCA TGAGCGGATA CATATTTGAA TGTATTTAGA AAAATAAACA AATAGGGGTT CCGCGCACAT
5058  TTCCCCGAAA AGTGCCACCT GACGTCGACGT CTAAGAAACC ATTATTATCA TGACATTAAC CTATAAAAT
5128  AGGGGTATCA CGAGGCCCTT TCGTCTTCAA
```

AUTOREGULATORY TETRACYCLINE-REGULATED SYSTEM FOR INDUCIBLE GENE EXPRESSION IN EUCARYOTES

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention is related to the recombinant DNA technology. A tetracycline-regulated system which provides autoregulatory, inducible gene expression in cultured cells and transgenic animals is described.

2. Related Art

Systems for inducible mammalian gene expression have typically encountered limitations such as basal leakiness, toxic or nonspecific effects of inducing agents or treatments, limited cell type applicability and low levels of expression (reviewed in Yarranton, G. T., *Curr. Opin. Biotech.* 3:506–511 (1992)). Recently, a system was described (Gossen, M. & Bujard, H., *Proc. Natl. Acad. Sci. USA* 89:5547–5551 (1992)) that overcomes many of these difficulties by placing target genes under the control of a regulatory sequence (tetO) from the tetracycline-resistance operon of Tn10. In bacteria, this short sequence is bound tightly by the tetracycline repressor protein (tetR), and binding is blocked by the antibiotic tetracycline (Hillen, W. & Wissmann, A., in *Protein-Nucleic Acid Interaction, Topics in Molecular and Structural Biology*, Saenger, W. & Heinemann, U., eds., Macmillan, London (1989), pp. 143–162). A hybrid fusion protein, the tetracycline transactivator (tTA), combines the tetR DNA binding domain with the transcriptional activation domain of VP-16, such that when tTA binds to a minimal promoter containing tetO sequences, transcription of the target gene is activated. Tetracycline binding to tTA prevents activation presumably by causing a conformational change in the tetR portion of tTA which blocks binding of tTA to tetO (Hinrichs, W., et al., *Science* 264:418–420 (1994)); gene activation is achieved by removing tetracycline (Gossen, M. & Bujard, H., *Proc. Natl. Acad. Sci. USA* 89:5547–5551 (1992)).

The primary limitation of this system is difficulty in expressing even moderate levels of the tTA protein (undetectable by western blotting and barely detectable by gel electrophoresis mobility shift assay (Gossen, M. & Bujard, H., *Proc. Natl. Acad. Sci. USA* 89:5547–5551 (1992))). Gossen and Bujard speculated that this was due to transcriptional "squelching" (Gill, G. & Ptashne, M., *Nature* (London) 334:721–724 (1988)) by the VP16 transactivator domain leading to death of cells expressing even modest levels of the tTA protein. These results combined with the observation of an apparently low level of expression of an inducible luciferase transgene using this system (Furth, P. A., et al., *Proc. Natl. Acad. Sci. USA* 91:9302–9306 (1994)) suggest that inefficiencies in tTA expression may contribute to the difficulty.

SUMMARY OF THE INVENTION

By placing the tTA gene under the control of a promoter containing tetO, an autoregulatory tTA expression vector is created that allows high levels of tTA expression. It is demonstrated herein that this strategy permits the creation of highly inducible transfected cells with much greater efficiency than the constitutive system. Furthermore, it allows the creation of transgenic mice in which expression of a luciferase reporter gene can be controlled by altering the concentration of tetracycline in the drinking water of the animals. The autoregulated expression of transactivator protein should make the tetracycline system applicable to a wide array of problems requiring inducible mammalian gene expression.

The first embodiment of the invention relates to a composition of matter comprising a polynucleotide molecule encoding a tetracycline transactivator fusion protein, said protein comprising a prokaryotic tet repressor and a eucaryotic transcriptional activator protein, and said polynucleotide molecule being operably linked to an inducible minimal promoter, which promoter contains at least one tet operator sequence. The open reading frame of the polynucleotide molecule encoding the tetracycline transactivator fusion protein is modified at its 5' end to provide an optimal context for translational initiation. In a preferred embodiment of the invention, it is modified to provide a unique restriction site, such as HindIII. In the most preferred embodiment of this invention, the open reading frame of the polynucleotide molecule encoding the tetracycline transactivator fusion protein is modified at its 5' end to encode an oligonucleotide identified as (SEQ ID NO:1). In a preferred embodiment, the polynucleotide molecule encoding a tetracycline transactivator fusion protein is DNA.

The second embodiment of the invention relates to a cloning vector containing the polynucleotide molecule of the invention. The most preferred embodiments of the invention relate to plasmids pTet-Splice and pTet-tTAK.

The third embodiment of the invention relates to a eucaryotic cell transfected with the polynucleotide molecule of the present invention. In a preferred embodiment, the eucaryotic cell contains tetracycline in an amount sufficient to suppress binding of tetracycline transactivator fusion protein to said inducible minimal promoter. In another preferred embodiment of the invention, the eucaryotic cell is further transfected with a polynucleotide molecule encoding a heterologous protein operably linked to an inducible minimal promoter, which contains at least one tet operator sequence. In the most preferred embodiment of the invention, at least one of the polynucleotide molecules is operably linked to a minimal promoter and seven tet operator sequences. In a further preferred embodiment, the polynucleotide molecule encoding a tetracycline transactivator fusion protein is expressed in an amount sufficient to drive expression of the polynucleotide molecule, encoding the heterologous protein, in the absence of tetracycline. In another preferred embodiment, the tetracycline transactivator fusion protein is present in an amount sufficient to drive expression of the heterologous protein.

The fourth embodiment of the invention relates to a method to decrease or shut off expression of a heterologous protein comprising
(a) transforming a eucaryotic cell with
(i) a first polynucleotide molecule encoding a tetracyline transactivator fusion protein, said protein comprising a prokaryotic tet repressor and a eucaryotic transcriptional activator protein, and said polynucleotide molecule being operably linked to an inducible minimal promoter, which promoter contains at least one tet operator sequence;
(ii) a second polynucleotide molecule encoding the heterologous protein, said protein being operably linked to an inducible minimal promoter, and said promoter containing at least one tet operator sequence; and (b) cultivating the eucaryotic cell in a medium comprising tetracycline or a tetracycline analogue. In a preferred embodiment, the second polynucleotide molecule is operably linked to a minimal promoter and seven tet operator sequences.

The fifth embodiment of the invention relates to a method to activate or enhance the expression of a heterologous protein comprising (a) transforming a eucaryotic cell with
(i) a first polynucleotide molecule encoding tetracycline transactivator fusion protein, said protein comprising a prokaryotic tet repressor and a eucaryotic transcriptional activator protein, and said polynucleotide molecule being operably linked to an inducible promoter, which promoter contains at least one tet operator sequence;
(ii) a second polynucleotide molecule encoding the heterologous protein, said protein being operably linked to an inducible minimal promoter, and said promoter containing at least one tet operator sequence; and (b) cultivating the eucaryotic cell in a medium lacking tetracycline or a tetracycline analogue.

The sixth embodiment of the invention relates to a kit comprising a carrier means having in close confinement therein at least two container means, wherein a first container means contains a first polynucleotide molecule encoding a tetracycline transactivator fusion protein, said protein comprising a procaryotic tet repressor and a eucaryotic transcriptional activator protein, and said polynucleotide molecule being operably linked to an inducible minimal promoter, which promoter contains at least one tet operator sequence; and a second container means contains a second polynucleotide molecule encoding said inducible minimal promoter, which promoter contains at least one tet operator sequence, which tet operator sequence is strategically positioned for being operably linked to a heterologous polynucleotide sequence encoding a polypeptide.

The seventh embodiment of the invention relates to a kit comprising a carrier means having in close confinement therein at least two container means, wherein a first container means contains a eucaryotic cell transfected with a first polynucleotide molecule encoding a tetracycline transactivator fusion protein, said protein comprising a procaryotic tet repressor and a eucaryotic transcriptional activator protein, and said polynucleotide molecule being operably linked to an inducible minimal promoter, which promoter contains at least one tet operator sequence; and a second container means contains a second polynucleotide molecule comprising an inducible minimal promoter, which promoter contains at least one tet operator sequence, which tet operator sequence is strategically positioned for being operably linked to a heterologous polynucleotide sequence encoding a heterologous polypeptide.

The polynucleotides described in this invention and cell lines containing said polynucleotides are research tools which allow one to tightly and quantitatively control the expression of a large variety of genes. This is of interest in broad areas of basic as well as applied research.

The invention also relates to the construction of eucaryotic production cell lines and strains in which the synthesis of the product, RNA or protein, is controlled by the tet regulatory system. These cell lines and strains allow one to induce protein synthesis at a predetermined time point or within a time window during a fermentation process. This control allows one to synthesize in large scale cultures gene products whose prolonged presence is lethal to the cells. Alternatively, the cells allow one to induce production of RNA when it is desirable to generate RNA molecules used to achieve a variety of cellular tasks, regulation, and function. Induction of RNA production can be controlled where, for example, the RNA are used as antisense oligos to inhibit the function of a gene which is either homologous or heterologous to the cell.

The invention also relates to the construction of cell lines which can be used in screening systems to identify compounds of pharmaceutical or other commercial value. In such systems, the expression of target molecules including but not limited to receptors such as the GABA or estrogen receptor, whose long term presence, in particular, in high copy numbers is often cell damaging, can be temporarily and quantitatively controlled.

The invention also relates to the construction of transgenic animals in which the expression of a single gene can be controlled externally by the tet regulatory system. Such genes include human genes whose expression, failure of expression, or other defects are involved in human diseases. Such transgenic animals can serve as models for human diseases in therapeutic studies and for the screening of compounds of pharmaceutical interest. The invention also relates to the construction of transgenic animals for the production of compounds of pharmaceutical or other commercial interest.

Another important application of this system makes possible the temporal control of gene expression, where for example, the gene of interest is introduced into a cell, animal, or plant to compensate for lethal knock out of certain genes in the transgene. Using the system to introduce a copy of the gene which has been suppressed or deactivated, enough protein or RNA can be produced to allow growth and development of the cell or the plant or animal until a time at which it is desired to shut off production of the gene and carry out the manipulations that require the lethal knock out of said gene.

BRIEF DESCRIPTION OF THE FIGURES

FIG. 2A depicts a bar graph analysis of clones containing pcDNA-tTAk (constitutive tTA expression). Seventeen stable transfectant clones (S1-1 to S1-17) were derived and assayed for the ability to carry out V(D)J recombination by transient co-transfection with a V(D)J recombination substrate and Tetp-controlled RAG-1 and RAG-2 expression vectors. Parallel transfections were performed in the presence (Tet+) and absence (Tet–) of tetracycline in the growth media, and the V(D)J recombination frequency (expressed as a percent) was determined as described in Materials and Methods. For comparison, four control assays performed in NIH3T3 cells are also shown (first two samples): transfection of the recombination substrate in the absence of RAG-1 and RAG-2, with and without tetracycline, and co-transfection of the recombination substrate with constitutive RAG expression vectors, with and without tetracycline. Tetracycline had no effect on V(D)J recombination frequency when RAG-1 and RAG-2 were expressed from constitutive hCMV promoters. Fold induction achieved by removing tetracycline is indicated above the bars in cases where clearly detectable recombination was observed.

FIG. 2B depicts a bar graph analysis of clones containing pTet-tTAk (autoregulatory tTA expression). Ten stable transfectant clones (S2-1 to S2-10) and two clones containing pTet-tTAk, pTet-R1A/C and pTet-R2A (S4-9 and S4-5) were assayed for the ability to carry out V(D)J recombination as described above. The first two samples are the same control samples described in FIG. 2A. Note the difference in the recombination frequency axis scale between FIG. 2A and FIG. 2B. Asterisks (*) mark two Tet+ transfections that yielded very small numbers of ampicillin resistant colonies, making the calculated recombination frequency unreliable. Consequently, the fold-inducibility for these clones is not shown. The number of ampicillin resistant colonies was low in these experiments (range, 350–55,550). Based on additional assays on some of the cell lines, we estimate that the reported recombination frequencies are as much as two fold overestimates in both FIG. 2A and FIG. 2B.

FIGS. 3A, 3B, and 3C are photographs of RNA blots and a Western blot depicting the detection of mRNA and protein expression activated using the inducible, autoregulatory system.

FIG. 3A is a photograph of a RNA blot of total cell RNA from S4-9 (stable co-transfectant of pTet-tTAk, pTet-R1A/ C, and pTet-R2A) cultured 23 h in the presence or absence of tetracycline, and S2-6 (stable transfectant of pTet-tTAk) transiently transfected with either pTet-R1 or pTet-R2 and cultured for 48 hours in the presence or absence of tetracycline. Blots were sequentially hybridized with probes detecting tTAk, RAG-1 and/or RAG-2, and γ-actin mRNA.

FIG. 3B is a photograph of a Western blot of cell extracts from S2-6 cells cultured for 48 hours in the presence or absence of tetracycline. Blot was probed with anti-tet R antibody-containing hybridoma supernatant which detects the tTA protein. The dye front is indicated.

FIG. 3C is a photograph of a blot of total cell RNA from thymus (T) and lung (L) of pTet-tTAk/Tet-luciferase transgenic mice maintained for 7 days in the presence or absence of tetracycline in their drinking water. Approximately 20 μg of RNA was loaded per lane.

FIG. 6 is a photograph of a Western blot of cell extracts from cultured S2-6 and S2-1 cell lines. First lane: marker proteins (no bands, visible); second and third lanes: S2-6 cells grown in the absence of tet for 16 days; fourth and fifth lanes: S2-6 cells grown in the presence of 0.5 μg/ml tet for 16 days; sixth lane: S2-1 cells grown in the presence of 0.5 μg/ml tet for 16 days; and seventh lane: S2-6 cells grown in the absence of tet for 2 days. A signal for the tTA protein is seen in S2-6 cells grown in the absence of tet for 2 days, but not in the same cells cultured in the absence of tet for 16 days. The band seen at the bottom in lanes 2–7 ("protein front") is the dye front and represents a non-specific signal.

FIGS. 9B, 9C, 9D, 9E, 9F, and 9G depict the nucleotide sequence of pTet-Splice (SEQ ID NO 2).

FIGS. 10B, 10C, 10D, 10E, 10F, and 10G depict the nucleotide as well as partial amino acid sequence of pTet-tTAk (SEQ ID NO 3) and (SEQ ID NO 4), respectively.

FIGS. 11B, 11C, 11D, 11E, and 11F depict the nucleotide as well as partial amino acid sequence of pUHD15-1 (SEQ ID NO 5) and (SEQ ID NO 6), respectively.

FIGS. 12B, 12C, 12D, 12E, and 12F depict the nucleotide as well as partial amino acid sequence of pUHC-13-3 (SEQ ID NO 7) and (SEQ ID NO 8), respectively.

DETAILED DESCRIPTION OF THE PREFERRED EMBODIMENTS

A system for tetracycline-regulated inducible gene expression was described recently which relies on constitutive expression of a transactivator fusion protein (tTA) consisting of the DNA binding domain of the tetracycline repressor and the transcriptional activation domain of VP16 (U.S. patent application Ser. No. 08/076,726, herein incorporated by reference in its entirety; Gossen, M. & Bujard, H., *Proc. Natl. Acad. Sci. USA* 89:5547–5551 (1992)). This system yielded only low levels of transactivator protein, probably because tTA is toxic. To avoid this difficulty, the tTA gene was placed under the control of the inducible promoter to which tTA binds, making expression of tTA itself inducible and autoregulatory.

When used to drive expression of the recombination activating genes RAG-1 and RAG-2, the autoregulatory system yielded both substantially higher levels of V(D)J recombination activity (70 fold on average) and inducible expression in a much larger fraction of transfected cells (autoregulatory, 90% vs. constitutive, 18%). In addition, this system allowed the creation of inducible transgenic mice in which expression of a luciferase transgene was induced tens to hundreds fold the basal levels in most tissues examined. Induced levels of expression were highest in thymus and lung and appear to be substantially higher than in previously reported inducible luciferase transgenic mice created with the constitutive system. With the modified system, inducible transactivator mRNA and protein were easily detected in cell lines by RNA and western blotting, and transactivator mRNA was detected by RNA blotting in some tissues of transgenic mice. This autoregulatory system represents an improved strategy for tetracycline regulated gene expression both in cultured cells and in transgenic animals.

As mentioned above, the inducible tetracycline expression system described recently (Gossen, M. & Bujard, H., *Proc. Natl. Acad. Sci. USA* 89:5547–5551 (1992)) relies on constitutive expression of the tTA gene from a fully functional human cytomegalovirus (hCMV) promoter, and a luciferase reporter gene under the control of the inducible promoter Tetp. In this system, tetracycline prevents the activation of luciferase gene expression, but does not prevent the tTA protein from exerting potentially deleterious effects on cells (Gill, G. & Ptashne, M., *Nature* (London) 334:721–724 (1988)).

Figure 1:
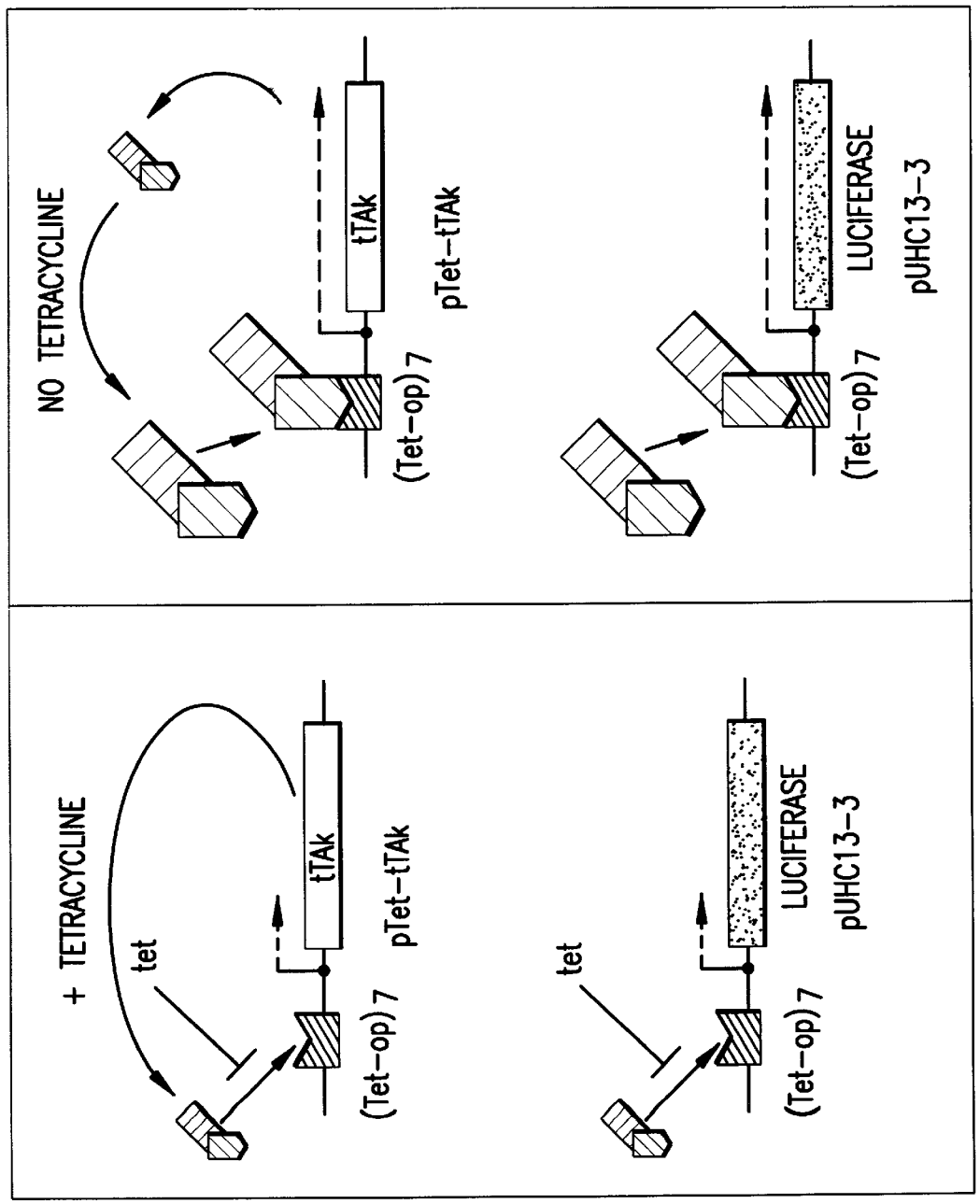
FIG. 1 is a schematic representation depicting the autoregulatory strategy for inducible gene expression. Autoregulatory expression of tTA is accomplished in pTet-tTAk by placing the tTAk gene (white box) under the control of Tetp consisting of seven copies of the tetracycline operator sequence (Tet-op; dark shaded box) upstream of the minimal human cytomegalovirus (hCMV) promoter region containing a TATA box and transcription start site (black circle). The luciferase reporter gene (shaded box) of pUHC13-3 is also controlled by the Tetp promoter. The tTA protein is shown as two adjoining striped boxes to represent the two domains of the protein (for DNA binding and transactivation). In the presence of tetracycline (left panel), the basal activity of the minimal hCMV promoter results in expression of very low levels of the tTA protein (represented as a small tTA icon), and any tTA protein produced is blocked from binding to Tet-op. Both luciferase and tTA expression are therefore maintained at low levels (thin, short dashed lines). When tetracycline is removed (right panel), the small amounts of tTA present bind Tet-op, stimulating expression of the tTA gene. Higher levels of the tTA protein now stimulate higher levels of tTA and thus, luciferase expression (heavy, long dashed lines).

Hence, in the autoregulatory plasmid pTet-tTAk, a modified tTA gene called tTAk was placed under the control of Tetp (FIG. 1). Tetracycline prevents tTA from binding to Tetp, preventing expression of both tTA and luciferase. This negative feedback cycle ensures that little or no tTA is produced in the presence of tetracycline, thereby reducing or eliminating possible toxic effects. When tetracycline is removed, however, this strategy predicts that tiny amounts of tTA protein (which may result from the leakiness of the minimal promoter), will bind to Tet-op and stimulate expression of the tTAk gene. A positive feedforward loop is initiated which in turn leads to higher levels of expression of tTA and thus, luciferase (FIG. 1). For constitutive expression of tTA, the tTAk gene was placed under the control of the hCMV promoter, followed with additional sequences to direct RNA splicing and polyadenylation of the tTA transcript. This plasmid (pcDNA-tTAk) also includes the neo gene, which allows for selection of the plasmid in mammalian cells.

The present invention relates to an autoregulatory control system that in eucaryotic cells allows regulation of expression of an individual gene over 200 to 3700 fold. This system is based on regulatory elements of a tetracycline-resistance operon, e.g. Tn10 of *E. coli* (Hillen & Wissmann, "Topics in Molecular and Structural Biology," in *Protein-Nucleic Acid Interaction*, Saeger & Heinemann, eds., Macmillan, London, 1989, Vol. 10, pp. 143–162), in which transcription of resistance-mediating genes is negatively regulated by a tetracycline repressor (tetR). In the presence of tetracycline or a tetracycline analogue, tetR does not bind to its operators located within the promoter region of the operon and allows transcription. By combining tetR with a protein domain capable of activating transcription in eucaryotes, such as (i) acidic domains (e.g. the C-terminal domain of VP16 from HSV (Triezenberg et al., *Genes Dev.* 2:718–729 (1988)) or empirically determined, non-eucaryotic acidic domains identified by genetic means (Giniger and Ptashne, *Nature* 330:670–672 (1987))) or (ii) proline rich domains (e.g. that of CTF/NF-1 (Mermod et al., *Cell* 58:741–753 (1989))) or (iii) serine/threonine rich domains (e.g. that of Oct-2 (Tanaka and Herr, *Cell* 60:375–386 (1990))) or (iv) glutamine rich domains (e.g. that of Sp1 (Courey and Tjian, *Cell* 55:867–898 (1988))) a hybrid transactivator is generated that stimulates minimal promoters fused to tetracycline operator (tetO) sequences. These promoters are virtually silent in the presence of low concentrations of tetracycline, which prevents the tetracycline-controlled transactivator (tTA) from binding to tetO sequences.

The specificity of the tetR for its operator sequence (Hillen & Wissmann, "Topics in Molecular and Structural Biology," in *Protein-Nucleic Acid Interaction*, Saeger & Heinemann, eds., Macmillan, London, 1989, Vol. 10, pp. 143–162) as well as the high affinity of tetracycline for tetR (Takahashi et al., *J. Mol. Biol.* 187:341–348 (1986)) and the well-studied chemical and physiological properties of tetracyclines constitute a basis for an autoregulatory inducible expression system in eucaryotic cells far superior to the lacR/O/IPTG system.

In particular, the invention relates to a first polynucleotide molecule coding for a transactivator fusion protein comprising the tet repressor (tetR) and a protein domain capable of activating transcription in eucaryotes, wherein the first polynucleotide molecule is operably linked to an inducible minimal promoter, which promoter contains at least one tet operator sequence. The polynucleotide coding for tetR may be obtained according to Postle et al., *Nucl. Acids Res.* 12:4849–4863 (1984), the contents of which are fully incorporated by reference herein. Other tetR sequences and the respective binding sites for these repressors are identified (Waters et al., *Nucl. Acids Res.* 11:6089–6105 (1983); Postle et al., *Nucl. Acids Res.* 12:4849–4863 (1984); Unger et al., *Gene* 31:103–108 (1984); Unger et al., *Nucl. Acids Res.* 12:7693–7703 (1984); Tovar et al., *Mol. Gen. Genet.* 215:76–80 (1988); for comparison and overview see Hillen and Wissmann in *Protein-Nucleic Acid Interaction*, Topics in Molecular and Structural Biology, Saenger and Heinemann (eds.), Macmillan, London, Vol. 10, pp. 143–162 (1989)) and can also be utilized for the expression system described.

The polynucleotide coding for the negatively charged C-terminal domain of HSV-16, a protein known to be a powerful transcription transactivator in eucaryotes, may be obtained according to Triezenberg et al., *Genes Dev.* 2:718–729 (1988), the contents of which are fully incorporated by reference herein. Preferably, the activating domain comprises the C-terminal 130 amino acids of the virion protein 16.

The polynucleotide molecule coding for tetR may be linked to a polynucleotide molecule coding for the activating domain of HSV-16 and recombined with vector DNA in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases.

The tetO sequence may be obtained, for example, according to Hillen & Wissmann, "Topics in Molecular and Structural Biology," in *Protein-Nucleic Acid Interaction*, Saeger & Heinemann, eds., Macmillan, London, 1989, Vol. 10, pp. 143–162, the contents of which are fully incorporated by reference herein. Other tetO sequences which may be used in the practice of the invention may be obtained from the references given in the following (Waters et al., *Nucl. Acids Res.* 11:6089–6105 (1983); Postle et al., *Nucl. Acids Res.* 12:4849–4863 (1984); Unger et al., *Gene* 31:103–108 (1984); Unger et al., *Nucl. Acids Res.* 12:7693–7703 (1984); Tovar et al., *Mol. Gen. Genet.* 215:76–80 (1988); for comparison and overview see Hillen and Wissmann in *Protein-Nucleic Acid Interaction*, Topics in Molecular and Structural Biology, Saenger and Heinemann (eds.), Macmillan, London, Vol. 10, pp. 143–162 (1989)), the disclosures of which are fully incorporated by reference herein in their entirety. One, two, three, four, five, six, seven, eight, nine or ten or more copies of the tet operator sequence may be employed, with a greater number of such sequences allowing an enhanced range of regulation. Multiple copies of the tet operator sequence provides a synergistic effect on the ability to control expression of the heterologous protein.

The polynucleotide sequence specifying the cytomegalovirus promoter may be obtained according to Boshart et al., *Cell* 41:521–530 (1985), the contents of which are fully incorporated by reference herein. Preferably, positions +75 to –53 or +75 to –31 of the promoter-enhancer may be employed. The promoter may be followed by a polylinker and then by the gene coding for the tetracycline transactivator fusion protein.

The invention also relates to an autoregulatory tetracycline-regulated system for inducing gene expression in eucaryotes, wherein a second polynucleotide molecule is introduced into the host. The second polynucleotide molecule encodes a protein of interest, wherein said polynucleotide is operably linked to a minimal promoter operatively linked to at least one tet operator (tetO) sequence. The minimal promoter linked to at least one tetO sequence is obtained as described above with regard to the first polynucleotide molecule. The difference between the first and the second polynucleotide molecules is that the promoter may be followed by a polylinker and then by the gene encoding the protein of interest. While the luciferase gene or other reporter genes may be used to demonstrate the operability of the regulatory system, the invention is not intended to be so limited.

The invention further relates to homologous and heterologous genes involved in developmental and differentiation processes, as well as in metabolic pathways ensuring cellular function and communication. It relates furthermore to cellular systems utilized in the production of substances of commercial interest, including, but not limited to immunoglobulins, components of the cytoskeleton, cell adhesion proteins, receptors, cytokines peptide hormones and enzymes.

The present invention also relates to eucaryotic cells transfected with the polynucleotide molecules of the present invention. In particular, the invention relates to eucaryotic cells transfected with (a) a first polynucleotide molecule coding for a transactivator fusion protein comprising a prokaryotic tet repressor and a protein capable of activating transcription in eucaryotes, wherein said first polynucleotide molecule is operably linked to a minimal promoter and at least one tet operator sequence; and (b) a second polynucleotide molecule coding for a protein, wherein said second polynucleotide molecule is operably linked to a minimal promoter and at least one tet operator sequence.

The two polynucleotide molecules may reside on the same or separate vectors. In a preferred embodiment, the first polynucleotide is integrated into the chromosome of a eucaryotic cell or transgenic animal and the second polynucleotide is introduced as part of a vector. Integration may be achieved where there is crossover at regions of homology shared between the incoming polynucleotide molecule and the particular genome.

The expression of the heterologous protein from such transfected eucaryotic cells may be tightly regulated. Unexpectedly, it has been determined that the autoregulatory expression system of the present invention may be used to induce expression by greater than 200 to 3700 fold, compared to greater than 50 to 100 fold increase observed when the constitutive expression system is used. In addition, it has been discovered that the expression system of the present invention allows one to rapidly turn on and off the expression of the heterologous gene in a reversible way. Moreover, it has been discovered that the expression system of the invention allows one to achieve a desired level of expression according to how much tetracycline or tetracycline analogue is employed. Thus, the autoregulatory expression system of the present invention is a great advance in the art.

The invention also relates to a method to decrease or to shut off (deactivate) the expression of a protein coded for by a polynucleotide, comprising cultivating the transfected eucaryotic cells of the present invention in a medium comprising tetracycline or a tetracycline analogue. It is possible to closely control the extent of expression by carefully controlling the concentration of tetracycline or tetracycline analogue in the culture media. As little as 0.0001 $\mu$g/ml of tetracycline will begin to result in a decrease of polypeptide (luciferase) expression. At about 0.1–1.0 $\mu$g/ml the expression is essentially shut off. The concentration of tetracycline or tetracycline analog which can be used to regulate the expression level may range from about 0.0001 to about 1 $\mu$g/ml.

The invention also relates to a method to turn on (activate) or to increase the expression of a protein coded for by a polynucleotide, comprising cultivating the eucaryotic cell of the invention in a medium lacking tetracycline or a tetracycline analogue.

Media which may be used in the practice of the invention include any media which are compatible with the transfected eucaryotic cells of the present invention. Such media are commercially available (Gibco/BRL).

The invention also relates to transgenic animals comprising one or two of the polynucleotide molecules of the present invention. Such transgenic animals may be obtained, for example, by injecting the polynucleotide into a fertilized egg which is allowed to develop into an adult animal. In particular, a few hundred DNA molecules are injected into the pro-nucleus of a fertilized one cell egg. The microinjected eggs are then transferred into the oviducts of pseudopregnant foster mothers and allowed to develop. It has been reported by Brinster et al., *Proc. Natl. Acad. Sci. USA* 82:4438–4442 (1985), the contents of which are fully incorporated by reference herein, that about 25% of mice which develop will inherit one or more copies of the microinjected DNA. Alternatively, the transgenic animals may be obtained by utilizing recombinant ES cells for the generation of the transgenes, as described by Gossler et al., *Proc. Natl. Acad. Sci. USA* 83:9065–9069 (1986), the contents of which are fully incorporated by reference herein. Animals transgenic for the gene encoding a tetR/ transcriptional activator domain fusion protein under the transcriptional control of at least one Tet-op sequences described above and/or the gene under control of this regulatory protein can be generated e.g. by the coinjection of the two polynucleotide molecules. Alternatively, independent animal lines transgenic for only one of the polynucleotides described can be generated in a first step:

(i) Animals transgenic only for the gene encoding the desired heterologous protein to be controlled by the transactivator can be screened for the desired nonactivated expression level. This includes indicator animals transgenic for a reporter gene (e.g. cat, luc, lacZ) under transcriptional control of the tetR/transcriptional activator domain fusion protein dependent minimal promoter, which are easy to screen for integration sites showing the desired, in general a low level basal expression. If advantageous, these empirically determined loci can be used subsequently for a homologous recombination approach (Mansour et al., Nature 336:348–352 (1988)), by which the reporter gene is substituted by a respective gene of interest in the previously analyzed integration site.

(ii) Animals transgenic only for a gene encoding a tetR/transcriptional activator domain fusion protein can be analyzed for the desired expression pattern of the regulator protein.

Subsequently, the desired double transgenic animals are obtained by breeding the two complementary transgenic animal lines.

The Definitions

In the description that follows, a number of terms used in recombinant DNA technology are utilized extensively. In order to provide a clear and consistent understanding of the specification and claims, including the scope to be given such terms, the following definitions are provided.

Expression: Expression is the process by which a polypeptide is produced from a structural gene. The process involves transcription of the gene into mRNA and the translation of such mRNA into polypeptide(s).

Autoregulatory expression vector: It refers to the invention as described herein. A modified tTA gene called tTAk is placed under the control of Tetp (FIG. 1). Tetracycline prevents tTA from binding to Tetp, preventing expression of both tTA and thus the desired protein (such as luciferase in FIG. 1). This negative feedback cycle ensures that little or no tTA is produced in the presence of tetracycline, thereby reducing or eliminating possible toxic effects. When tetracycline is removed, however, this strategy predicts that tiny amounts of tTA protein (which may result from the leakiness of the minimal promoter), will bind to Tet-op and stimulate expression of the tTAk gene. A positive feedforward loop is initiated which in turn leads to higher levels of expression of tTA and thus, luciferase (FIG. 1).

Optimal context for translational initiation: consists of the ATG methionine initiation codon, plus flanking nucleotides as defined by: Kozak, M., Cell 44:283–292 (1986). The sequence is: CC(A or G)CCATGG, with the initiation codon shown in bold. This sequence provides for the most efficient initiation of translation by the translation machinery.

Promoter: A DNA sequence generally described as the region 5' of a gene, located proximal to the start site of transcription. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Inducible Minimal Promoter: It refers to the minimum number of nucleic acids from a promoter sequence, which in combination with other regulatory elements, is capable of initiating transcription. A minimal promoter, at the minimum, defines the transcription start site but by itself is not capable, if at all, of initiating transcription efficiently. The activity of such minimal promoters depend on the binding of activators such as a tetracycline-controlled transactivator to operably link binding sites.

V(D)J Recombination: So called for the variable (V), diversity (D), and joining (J) gene segments used in recombination, it is a process by which the developing lymphocytes begin to generate their enormous range of binding specificities from a limited amount of genetic information. It is known to assemble seven different loci in developing lymphocytes: $\mu$, $\kappa$, and $\lambda$ in B cells, and $\alpha$, $\beta,\lambda$, and $\delta$ in T cells (for reviews see Blackwell and Alt (1988), Immunoglobulin genes, In Molecular Immunology, Hames and Glover, eds. (Washington, D.C.: IRL Press), pp. 1–60; Davis and Bjorkman, Nature 334:395–402 (1988); Raulet, D. H., Annu. Rev. Immunol. 7:175–207 (1989)).

RAG-1 and RAG-2: RAG-1 (recombination activating gene-1) and RAG-2 are genes co-expressed in maturing lymphocytes. Expression of both genes is absolutely required for V(D)J recombination and lymphocyte development. When transfected together into fibroblasts, RAG-1 and RAG-2 induce V(D)J recombination activity. The RAG-1 and RAG-2 genes lie adjacent to each other in the vertebrate genome and encode unrelated proteins. Both RAG-1 and RAG-2 are conserved between species that carry out V(D)J recombination, and their expression pattern correlates precisely with that of V(D)J recombinase activity.

Founder: It is the original (first generation) transgenic animal, i.e. an animal carrying a transgene, which has been made by manipulating the genome of a fertilized egg and implanting the egg into a pseudopregnant animal.

Operator: It is the site on DNA at which a repressor protein binds to prevent transcription from initiating at the adjacent promoter.

Operon: is a unit of bacterial gene expression and regulation, including structural genes and control elements in DNA recognized by regulator gene product(s).

Repressor: It is a protein that binds to operator on DNA or to RNA to prevent transcription or translation, respectively.

Repression: is the ability of an organism to prevent synthesis of certain enzymes when their products are present: more generally, refers to inhibition of transcription (or translation) by binding of repressor protein to specific site on DNA (or mRNA).

Open Reading Frame (ORF): contains a series of triplets coding for amino acids without any termination codons; sequence is (potentially) translatable into protein.

Heterologous Protein: is a protein that does not naturally occur in the specific host organism in which it is present.

Unique Restriction site: refers to a single occurrence of a site on the nucleic acid that is recognized by a restriction enzyme.

Tetracycline Transactivator Fusion Protein: A hybrid fusion protein, the tetracycline transactivator (tTA), combines the tetR DNA binding domain with the transcriptional activation domain of VP-16, such that when tTA binds to a minimal promoter containing tetO sequences, transcription of the target gene is activated. Tetracycline binding to tTA prevents activation presumably by causing a conformational change in the tetR portion of tTA which blocks binding of tTA to tetO (Hinrichs, W., et al., Science 264:418–420

(1994)); gene activation is achieved by removing tetracycline (Gossen, M. & Bujard, H., *Proc. Natl. Acad. Sci. USA* 89:5547–5551 (1992)).

Domain: of a protein is a discrete continuous part of the amino acid sequence that can be equated with a particular function.

Cloning vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector.

Expression vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Eucaryotic Cell: According to the invention, a eucaryotic cell may be a cell of any eucaryotic organism including, but not limited to, yeast, plant cells, insect cells, e.g. Schneider and Sf9 cells; mammalian cells, e.g. lymphoid and HeLa cells (human), NIH3T3 and embryonic stem cells (murine), and RK13 (rabbit) cells.

Recombinant Eucaryotic Host: According to the invention, a recombinant eucaryotic host may be any eucaryotic cell which contains the polynucleotide molecules of the present invention on an expression vector or cloning vector. This term is also meant to include those eucaryotic cells that have been genetically engineered to contain the desired polynucleotide molecules in the chromosome, genome or episome of that organism. Thus, the recombinant eucaryotic host cells are capable of stably or transiently expressing the proteins.

Recombinant vector: Any cloning vector or expression vector which contains the polynucleotide molecules of the invention.

Host: Any prokaryotic or eucaryotic cell that is the recipient of a replicable vector. A "host," as the term is used herein, also includes prokaryotic or eucaryotic cells that can be genetically engineered by well known techniques to contain desired gene(s) on its chromosome or genome. For examples of such hosts, see Sambrook et al., *Molecular Cloning: A Laboratory Manual*, Second Edition, Cold Spring Harbor Laboratory, Cold Spring Harbor, N.Y. (1989).

Gene: A DNA sequence that contains information needed for expressing a polypeptide or RNA molecule, including an RNA molecule which is not translated into polypeptide and functions as RNA, e.g., ribosomal genes.

Structural gene: A DNA sequence that is transcribed into messenger RNA (mRNA) that is then translated into a sequence of amino acids characteristic of a specific polypeptide.

Polynucleotide molecules: A polynucleotide molecule may be a polydeoxyribonucleic acid molecule (DNA) or a polyribonucleic acid molecule (RNA).

Complementary DNA (cDNA): A "complementary DNA," or "cDNA" gene includes recombinant genes synthesized by reverse transcription of mRNA and from which intervening sequences (introns) have been removed.

Fragment: A "fragment" of a polypeptide or a polynucleotide molecule is meant to refer to any polypeptide or polynucleotide subset of that molecule.

Tetracycline Analogue: A "tetracycline analogue" is any one of a number of compounds that are closely related to tetracycline and which bind to the tet repressor with a $K_a$ of at least about $10^6$ $M^{-1}$. Preferably, the tetracycline analogue binds with an affinity of about $10^9$ $M^{-1}$ or greater, e.g. $10^{11} M^{-1}$. Examples of such tetracycline analogues include, but are not limited to those disclosed by Hlavka and Boothe, "The Tetracyclines," in *Handbook of Experimental Pharmacology* 78, R. K. Blackwood et al. (eds.), Springer-Verlag, Berlin, N.Y., 1985; L. A. Mitscher, "The Chemistry of the Tetracycline Antibiotics," *Medicinal Research* 9, Dekker, N.Y., 1978; Noyee Development Corporation, "Tetracycline Manufacturing Processes," *Chemical Process Reviews*, Park Ridge, N.J., 2 volumes, 1969; R. C. Evans, "The Technology of the Tetracyclines," *Biochemical Reference Series* 1, Quadrangle Press, New York, 1968; and H. F. Dowling, "Tetracycline," *Antibiotics Monographs*, no. 3, Medical Encyclopedia, New York, 1955; the contents of each of which are fully incorporated by reference herein.

Figure 5:
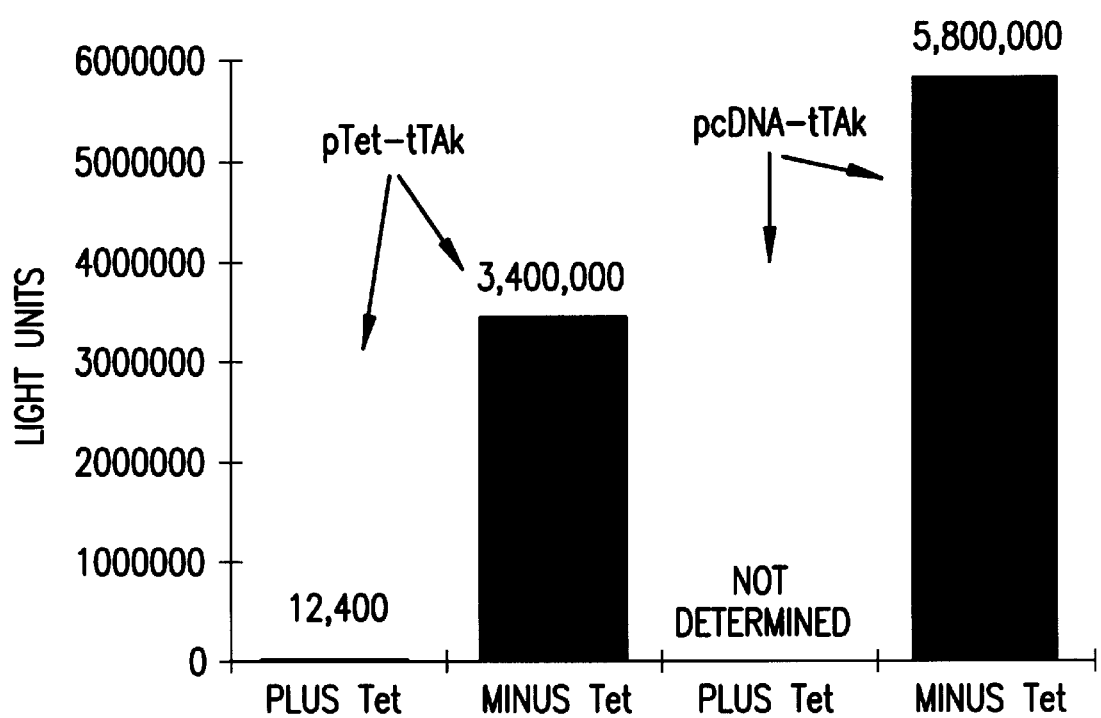
FIG. 5 is a graph depicting the ability of pTet-tTAk to induce expression of luciferase activity in a transfected fibroblast cell line. pUHC13-3 was co-transfected with either pTet-tTAk or pcDNA-tTAk into NIH3T3 fibroblast cells, and 48 hours later the cells were harvested and the luciferase light units present in the extracts was measured. pTet-tTAk transfections were performed in the presence and absence of tetracycline (tet), while pcDNA-tTAk transfection was performed only in the absence of tet. It is important to note that the luciferase values have not been corrected for transfection efficiency. In addition, under the conditions used, pcDNA-tTAk would replicate inside the cells while pTet-tTAk would not. Therefore, comparisons between the values obtained with pTet-tTAk and pcDNA-tTAk are not meaningful.

Comparison of the constitutive and autoregulatory inducible expression systems in cultured cells After confirming that pcDNA-tTAk and pTet-tTAk could direct high levels of expression of luciferase activity, and that expression directed by pTet-tTAk was inducible (see FIG. 5), the functional properties of these plasmids were compared in a more stringent assay: the ability to express high levels of the proteins encoded by the recombination activating genes RAG-1 and RAG-2 (Schatz, D. G. et al., *Cell* 59:1035–1048 (1989); Oettinger, M. A. et al., *Science* 248:1517–1523 (1990)). During lymphoid development, RAG-1 and RAG-2 participate in the assembly of functional immunoglobulin and T cell receptor genes from component variable (V), diversity (D) and joining (J) gene segments, a process known as V(D)J recombination. Most important for the experiments described here, RAG-1 and RAG-2 are necessary and sufficient to activate the V(D)J recombinase in non-lymphoid cells (reviewed in Schatz, D. G. et al., *Annu. Rev. Immunol.* 10:359–383 (1992)), and the activity of the V(D)J recombinase can be quantitatively assayed using extrachromosomal recombination substrates (Hesse, J. E. et al., *Cell* 49:775–783 (1987)).

Extensive efforts to express RAG-1 and RAG-2 in NIH3T3 fibroblast cells using a variety of promoters have revealed that it is difficult to achieve a recombination frequency (Rn) of greater than a few percent, as assayed with standard extrachromosomal recombination substrates (Sadofsky, et al., *Nuc. Acids. Res.* 22:1805–1809 (1994); Sadofsky, et al., *Nuc. Acids. Res.* 21:5644–5650 (1993); Cuomo and Oettinger, *Nuc. Acids. Res.* 22:1810–1814 (1994)). Only high titer RAG-retroviruses developed by others have reproducibly shown the ability to achieve an Rn as high as 10% (Silver, D. P. et al., *Proc. Natl. Acad. Sci. USA* 90:6100–6104 (1993)). What is clear, however, is that Rn correlates strongly with RAG expression levels over at least three orders of magnitude (Rn from 0.01% to well above 10%; Oltz, E. M., et al., *Mol. Cell. Biol.* 13(10):6223–6230 (1993)). Thus the ability to express the RAG proteins, as measured by V(D)J recombinase activity, is an appropriate test of an inducible expression system both because of the difficulties that have been encountered in expressing the proteins and because of the sensitivity and range of the assay.

Figure 2A:
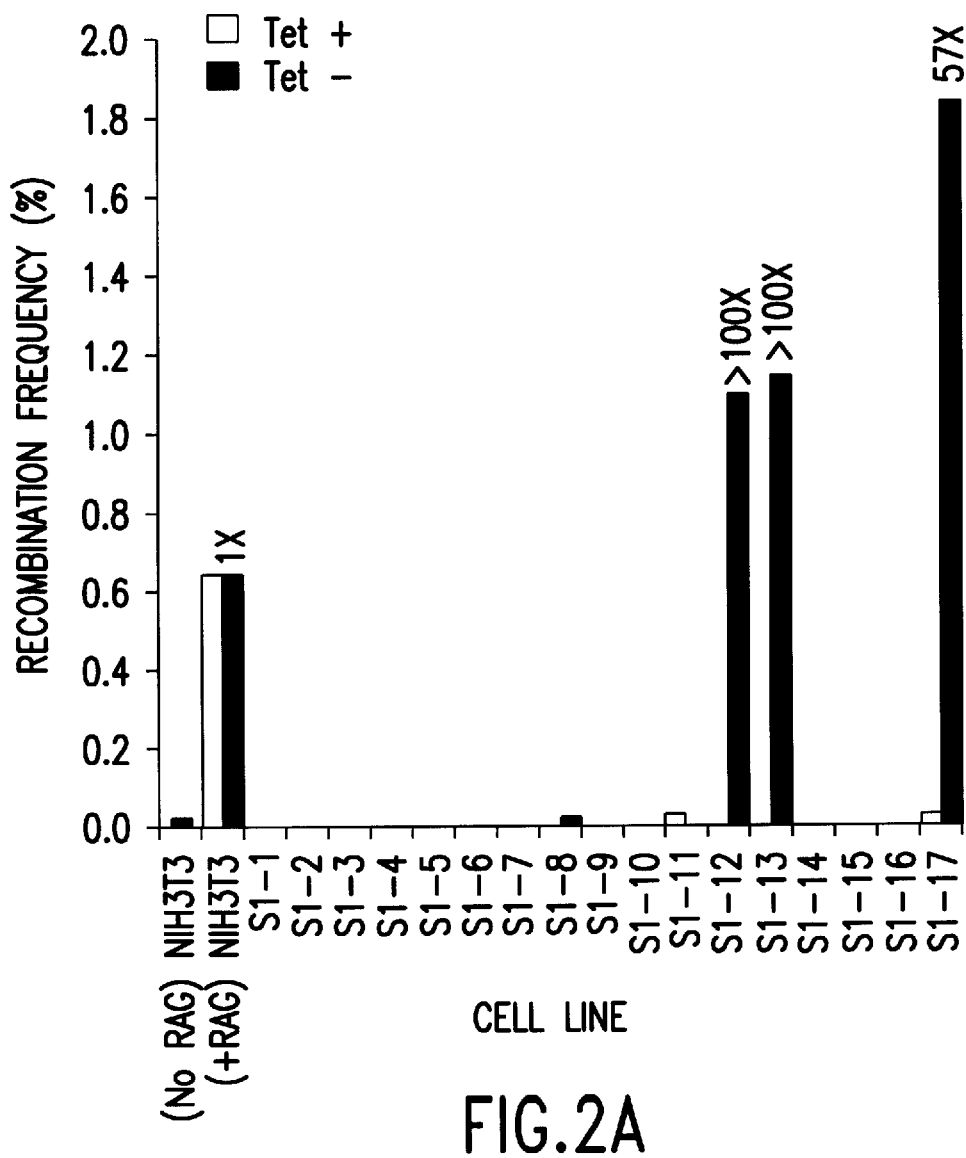
FIGS. 2A and 2B are bar graphs which depict inducible V(D)J recombination in NIH3T3 fibroblasts.
Figure 2B:
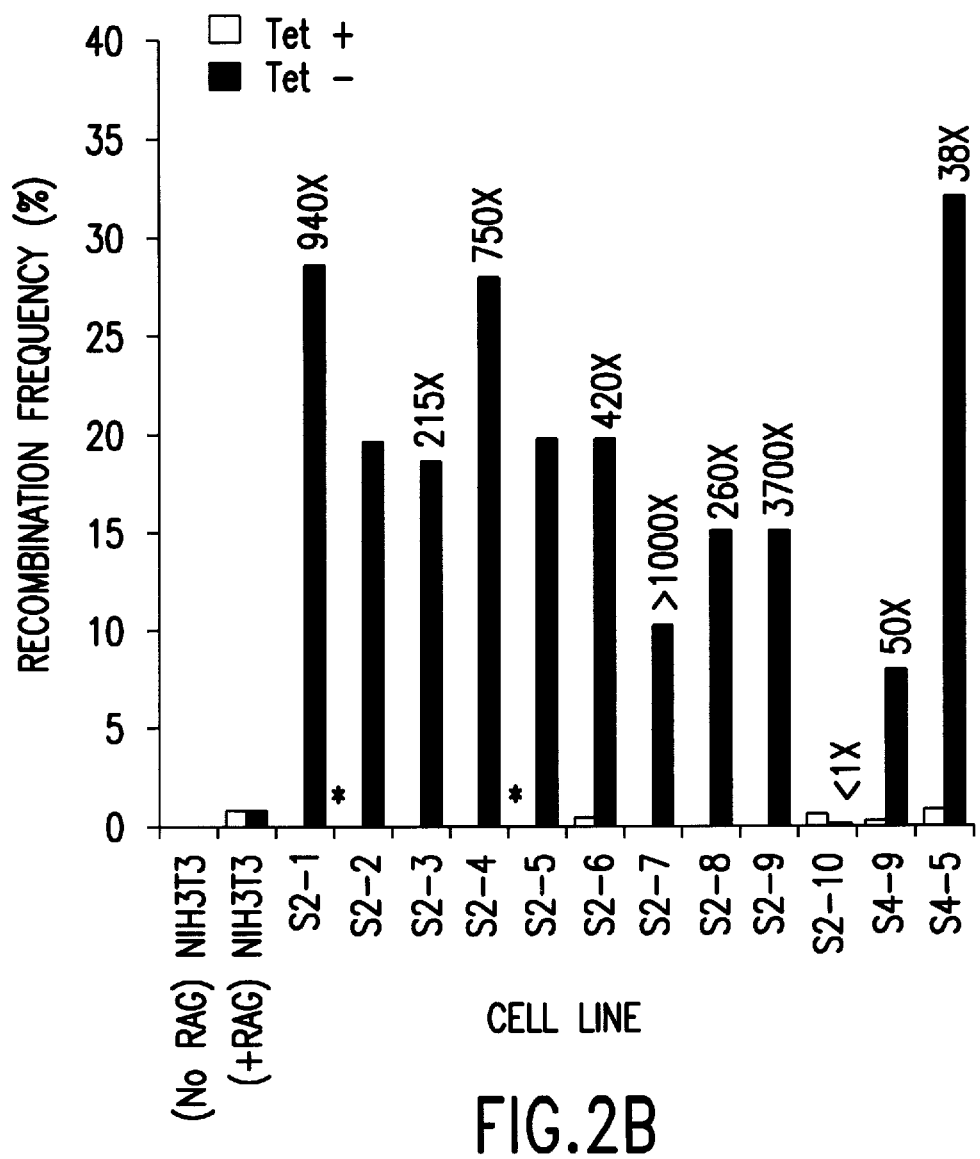

NIH3T3 fibroblast clones stably transfected with pcDNA-tTAk (17 clones) or with pTet-tTAk (10 clones) were tested for their ability to perform V(D)J recombination after transient transfection with a recombination substrate and Tetp-regulated RAG-1 and RAG-2 (FIG. 2). Each clone was assayed in parallel in the presence (uninduced state) or absence (induced state) of tetracycline and the results compared to control transfections either lacking RAG-1 or RAG-2 (first sample in FIGS. 2A and 2B) or containing highly active, constitutive RAG expression constructs (in which RAG expression is driven by the hCMV promoter; second sample in FIGS. 2A and 2B). In addition, two NIH3T3 clones stably transfected with pTet-tTAk and the Tetp-regulated RAG expression vectors were assayed by transient transfection of the recombination substrate in the presence or absence of tetracycline (last two samples in FIG. 2B).

The autoregulatory expression system (pTet-tTAk) represents a substantial improvement over the constitutive expression system (pcDNA-tTAk). Only 3 of 17 (18%) pcDNA-tTAk transfectants had clearly detectable levels of V(D)J recombination (FIG. 2A), with the highest levels of recombination (in clone S1-17) being 3 fold that seen in the positive control with constitutively active RAG expression vectors (second sample; FIG. 2A). Removal of tetracycline induced recombination in these three clones (S1-12, S1-13, S1-17) by greater than 50 to 100 fold. In contrast, 9 of 10 (90%) pTet-tTAk transfectants (FIG. 2B) showed high levels of recombination (note the difference in scale between FIGS. 2A and 2B), with the highest levels (28% in S2-1) being nearly 50 fold higher than the positive control (FIG. 2B, second sample). Inducibility in these nine clones was excellent, ranging from over 200 fold to 3700 fold. Equally high were the observed recombination frequencies achieved in clones stably transfected with pTet-tTAk and Tetp-regulated RAG plasmids (S4-9 and S4-5; last two samples in FIG. 2B).

Figure 6:
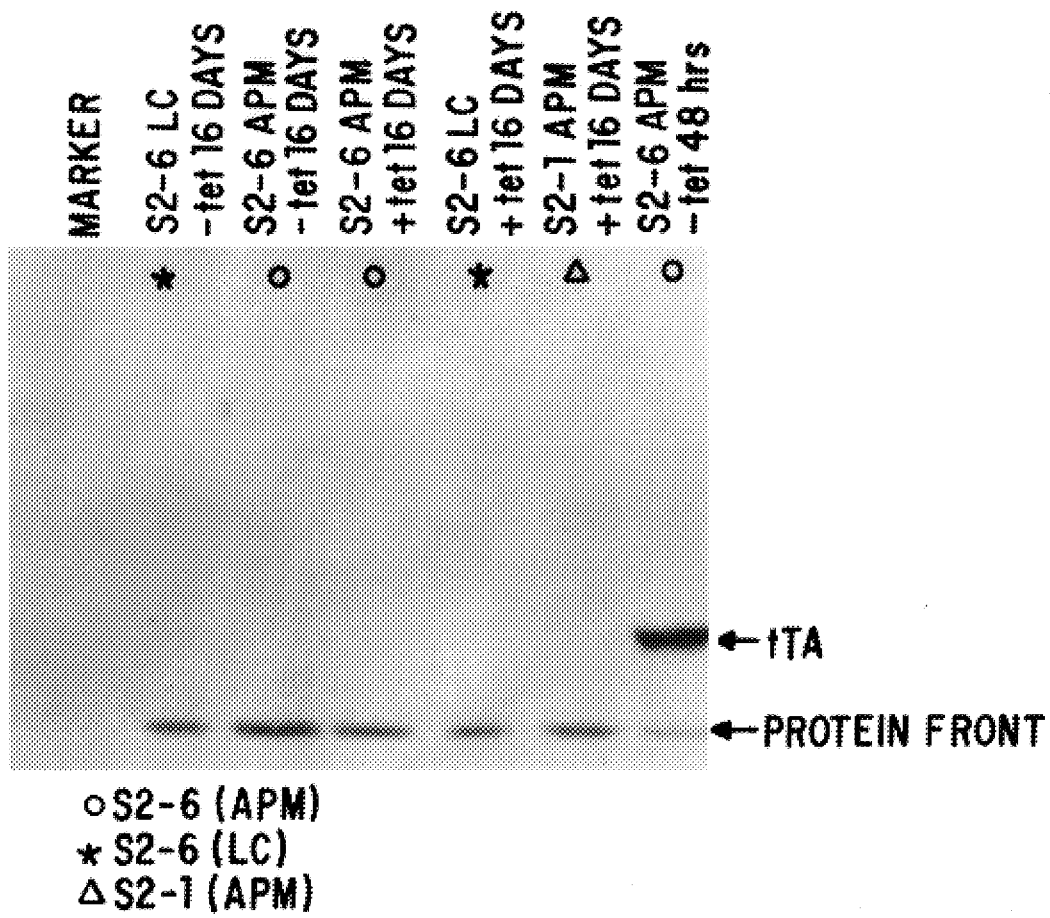
FIG. 6 is a photograph of an autoradiograph depicting loss of tTA protein at 16 days without tetracycline in S2-6 cells.

Further characterization of the pTet-tTAk transfectant S2-6 and the pTet-tTAk+pTet-R1A/C+pTet-R2A transfectant S4-9 demonstrated that the ability to induce high levels of V(D)J recombinase activity is reproducible and that recombination decreases three fold with 0.01 µg/ml tetracycline and twenty fold with 0.1 µg/ml tetracycline. Greater than 50% cell death was observed within 10 days and a loss of detectable tTA protein was detected by 3 weeks in S2-6 cells cultured in the absence of tetracycline (FIG. 6).

FIG. 3A demonstrates that mRNA corresponding to the tTAk and RAG-1 and RAG-2 genes is detected in induced cell lines stably expressing tTA and stably or transiently expressing RAG-1 and/or RAG-2. FIG. 3B shows that in S2-6 cells induced for 48 hours by tetracycline removal, tTA protein is easily detectable by Western blotting.

The creation of inducible transgenic mice

To assess the potential of using the autoregulatory tetracycline system in transgenic mice, the relevant portions of pTet-tTAk and pUHC13-3 were purified and co-microinjected into fertilized eggs, which were then implanted into pseudopregnant female mice. Five transgene positive founders were screened for inducibility by measurement of luciferase levels in peripheral blood mononuclear cells (PBMCs) from mice removed from tetracycline for 3 to 18 days. Three founders, #17, #19, and #20 showed high levels of luciferase activity after induction, ranging from 70–900 fold that obtained in extracts of PBMCs from transgene negative mice in the same experiments (Table 1). Founder #11 was leaky and #12 showed no inducible luciferase in PBMCs. It is presumed that variability in inducibility and leakiness of transgenes in different founders is a consequence of the site of integration and/or structure of the integrated transgenes. There was no obvious correlation between levels of luciferase expression or leakiness in PBMCs and the copy number of the transgenes. Particularly significant was that when mouse #20 was again given water containing tetracycline for 18 days, after a previous 7 day induction in the absence of tetracycline, luciferase levels dropped essentially to background, demonstrating that transgene induction is reversible (Table 1). Germline transmission of the transgenes from founders #17 and #20, but not #19 was achieved.

TABLE 1

Luciferase levels in peripheral blood mononuclear cells of transgenic and control mice

| | Transgene Copy #[a] | | Days after removal of tetracycline from drinking water[b] | | | | |
|---|---|---|---|---|---|---|---|
| Mouse | pTet-tTA | pTet-Luc | Day 0 | Day 3 | Day 7 | Day 18 | Day 7* |
| 15 | — | — | ND | 50 (1) | 9.4 (1) | ND | ND |
| 21 | — | — | 11 (1.2) | ND | 0 | 36 (0.5) | ND |
| 13 | — | — | ND | ND | 60 (1) | 69 (1) | ND |
| 17 | 15 | 30 | ND | 1317 (26) | 8595 (914) | ND | ND |
| 20 | 80 | 120 | ND | 1137 (23) | 7300 (777) | ND | 88 (1.3) |
| 11 | 40 | 20 | 943 (100) | ND | 3983 (66) | 3013 (44) | ND |
| 19 | 20 | 40 | 0 (1) | ND | 18250 (304) | ND | ND |

[a]The approximate transgene copy number of pTet-tTA and pUHC13-3 (pTet-luc) as estimated from Southern blotting.
[b]Values represent light units (with lysis buffer background subtracted) per $10^6$ cells measured in cell extracts of PBMCs from mice removed from tetracycline for the indicated number of days. Values in parentheses are the fold increase or decrease in luciferase activities relative to that in cell extracts from a transgene negative mouse in the assay performed the same day.
Day 7* denotes luciferase activity measured in cell extracts from mice in whose drinking water tetracycline was removed for 7 days and then restored for 18 days.

Figure 4:
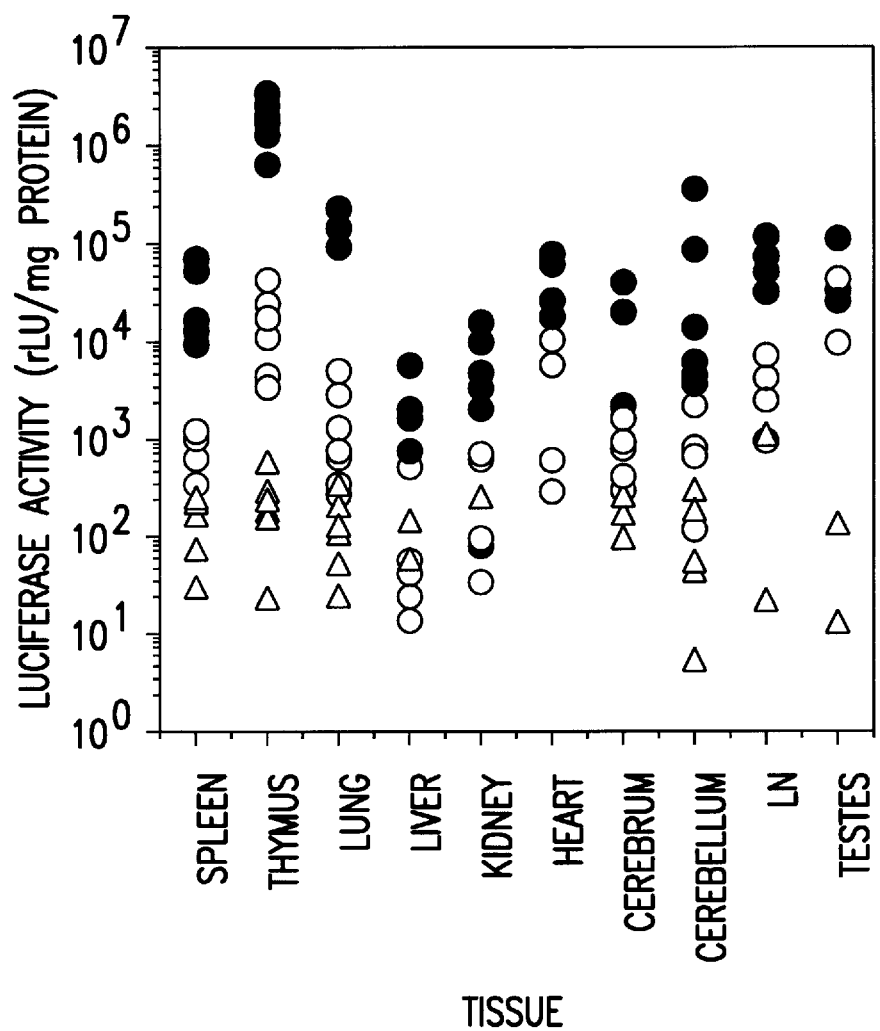
FIG. 4 is a graph depicting inducible luciferase activity in tissues of transgenic mice. Values represent the relative light units (rLU) (with lysis buffer background subtracted) per mg protein in tissue lysates from 4–7 week old mice maintained for 7–8 days in the presence or absence of tetracycline in their drinking water. Open triangles are transgene negative mice; open circles are uninduced transgene positive mice; and closed circles are induced transgene positive mice. Mice were genetically identical with respect to the transgenes. Results are compiled from three separate experiments.

To analyze more carefully the inducibility of luciferase in transgenic mice, a variety of tissues and organs of second or third generation transgene positive progeny of founder #17 and #20 (backcrossed to C57B1/6) were removed from tetracycline for 7 or 8 days and were compared to transgene identical positive progeny maintained on tetracycline. As shown in FIG. 4 and Table 2, the progeny of mouse #51 (from Founder #17) showed luciferase activity in all organs examined. Levels of luciferase activity varied substantially between tissues, with expression consistently high in thymus and lung, and low in liver and kidney. Induction ranged from 2-fold in testes to 150-fold in thymus. Luciferase activity ($10^5$–$4 \times 10^6$ rLU/mg protein) was also detected in day 17 fetal brain and liver of transgene positive mice conceived in the absence of tetracycline. Additionally, transgene positive mice conceived and maintained from gestation through 3.5 months in the absence of tetracycline continued to express optimal levels of luciferase and appeared normal. Progeny from founder #20 also showed highest levels of inducible luciferase activity in thymus and lung, although inducibility and tissue distribution of luciferase were more restricted than in the progeny of founder #17. Northern blotting demonstrated that tTA mRNA levels were clearly induced in the thymus and lung from progeny of mouse #51 after removal of tetracycline (FIG. 3C). Mice removed from tetracycline for up to 6 months appear healthy, indicating that induction of the tTA protein in vivo is not toxic or lethal. It was also observed that mRNA hybridizes to a probe specific for the luciferase gene in thymus from induced mice.

TABLE 2

Average luciferase activity and fold induction in tissues of transgenic mice[a]

| Tissue | Av. TG Neg. | Av. Unind. | Av. Ind. | Fold Induction |
|---|---|---|---|---|
| Spleen | 107 (9) | 684 (8) | 33,180 (10) | 48 |
| Thymus | 220 (9) | 16,243 (8) | 2,448,580 (10) | 151 |
| Lung | 138 (9) | 1,617 (8) | 169,538 (10) | 105 |
| Liver | 69 (3) | 214 (6) | 2,022 (8) | 9 |
| Kidney | 87 (3) | 361 (6) | 9,440 (8) | 26 |
| Heart | 0 (3) | 5,971 (6) | 32,540 (8) | 5 |
| Cerebrum | 94 (7) | 754 (6) | 9,836 (8) | 13 |
| Cerebellum | 91 (7) | 904 (6) | 67,410 (8) | 75 |
| LN | 617 (2) | 3,892 (4) | 74,449 (5) | 19 |
| Testes | 71 (2) | 30,398 (2) | 60,911 (3) | 2 |

[a]The average values combine data from the experiments shown in FIG. 4. The number of mice in each group is indicated in parentheses. The average fold induction for each tissue is shown. Values represent rLU/mg protein with lysis buffer background (130 rLU to 180 rLU) subtracted.

The autoregulatory system (pTet-tTAk) described here represents a substantial improvement over a constitutive expression strategy (pcDNA-tTAk) in cultured cells, in all likelihood because it prevents toxic effects of the transactivator in the uninduced state and allows for higher levels of transactivator after induction. The constitutive expression strategy is less effective in two regards: a smaller fraction of clones produce any expression at all (18% versus 90%) and induced V(D)J recombinase levels are much lower (by more than 70 fold, averaging over all clones). The kinetics of induction of gene expression with the two systems appears comparable. In preliminary experiments with the autoregulatory system, strong expression of transactivator mRNA is observed 12 hours post induction consistent with the optimal level of protein expression observed at 24 hours with the constitutive system (Gossen, M. & Bujard, H., Proc. Natl. Acad. Sci. USA 89:5547–5551 (1992)). Stable transfection of pTet-tTAk should allow easy derivation of activator cell lines in which a variety of genes can be inducibly expressed by subsequent transient or stable transfection.

Previous attempts to create inducible transgenic mice using genes activated by heavy metal ions or aromatic hydrocarbons have been hampered by leakiness, relatively low levels of induction, restricted tissue specificity, and toxicity or carcinogenicity of inducing agents (Jones, S. N. et al., Nucl. Acids Res. 19(23):6547–6551 (1991); Goodnow, C. C. et al., Nature 342:385–391 (1989); and reviewed in Yarranton, G. T., Curr. Opin. Biotech. 3:506–511 (1992)). The constitutive tetracycline system has been used to create inducible transgenic mice (Furth, P. A., et al., Proc. Natl. Acad. Sci. USA 91:9302–9306 (1994)) and avoids some of the difficulties of these earlier approaches. Assuming that equally sensitive luciferase measurement procedures were employed, the autoregulatory system provides approximately two orders of magnitude more luciferase activity in thymus ($1.1 \times 10^4$ rLU/mg protein maximum with the constitutive system vs. $2.5 \times 10^6$ rLU/mg protein with the autoregulatory system) and lung ($1.5 \times 10^3$ rLU/mg protein maximum with constitutive system vs. $1.7 \times 10^5$ rLU/mg protein with autoregulatory system). Additional benefits of the autoregulatory system appear to be a greater induction of luciferase activity in the thymus (150-fold vs. 67-fold), and easily detectable levels of luciferase activity in tissues which show little or no activity in the unmodified system such as lung, kidney and brain. Additionally, since activity in thymus, spleen, and lymph nodes is detected, this system might be especially suited to studies of the immune system. No gross perturbations of splenic architecture were observed in hematoxalin/eosin stained tissue sections from adult, luciferase expressing, transgenic mice maintained in the absence of tetracycline since conception. As seen with the unmodified system, leakiness varies between tissues, though it is higher in the thymus with the autoregulatory system than with the constitutive system.

By comparison to luciferase protein standards, the luciferase activity that was observed in thymus corresponds to an average of approximately 30 molecules of luciferase per cell. However, it is not known what fraction of cells express luciferase activity or how expression levels vary between expressing cells. Since induction of tTA expression in this system depends upon a low level of leakiness of the tTA transgene, it is expected that inducibility will vary with the transcriptional profiles of individual cell types and stages of differentiation. Therefore, per cell calculations of luciferase protein may under represent the actual levels induced in individual cells.

These results demonstrate that highly inducible and reversible expression from a Tetp-controlled reporter transgene can be obtained using the pTet-tTAk construct, and suggest that mice can develop normally in the presence of tetracycline and these transgenes, and that induction by removal of tetracycline does not lead to any obvious ill-effects on the mice, their ability to breed, or fetal development. Therefore, the potential toxicity of the tTA protein in vivo may not be a serious difficulty. Induced mice still express optimal levels of luciferase 3.5 months post tetracycline removal and remain viable at least six months in the absence of tetracycline, suggesting that transgene expression is tolerated and is not downregulated.

The pTet-tTAk system should be able to direct expression of any desired gene or genes in an inducible manner. This expression system should be widely applicable to the study of gene function in transfected cells and in vivo, to the creation of disease models for the testing of therapeutic agents, and to efforts to understand the development of mammalian organisms. It will be particularly useful in allowing regulated transgenic expression of genes otherwise too toxic to be tolerated by the organism during development.

EXAMPLES

The following examples are intended to further illustrate certain preferred embodiments of the invention and are not intended to be limiting in nature.

Figure 12A:
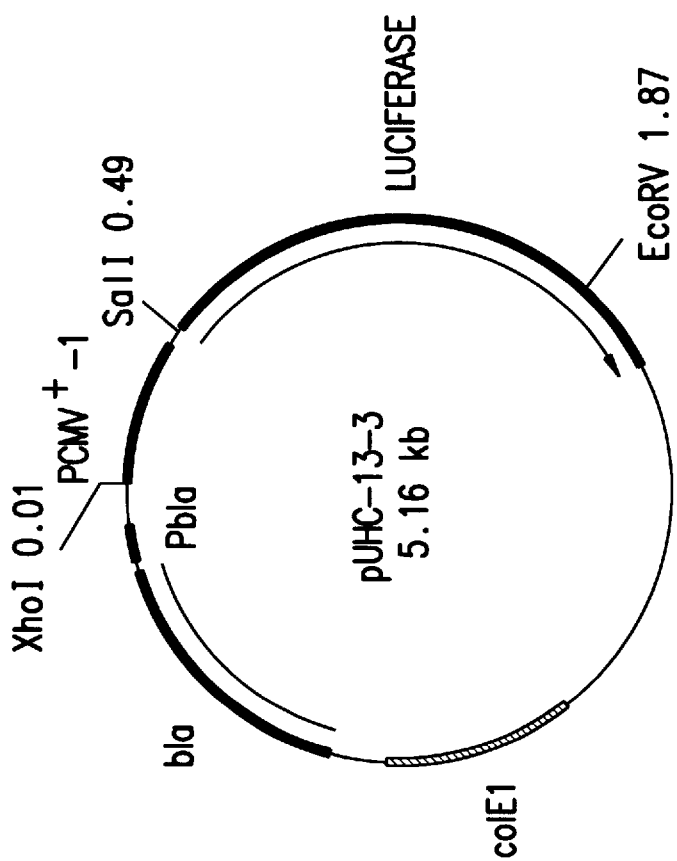
FIG. 12A depicts a restriction map of pUHC-13-3.

Materials and Methods
Details of Plasmid Constructions:
The plasmid pUHC 13-3 (described by Gossen & Bujard, Proc. Natl. Acad. Sci. USA:89:5547–5551 (1992)) is 5157 base pairs in size and has three EcoRI restriction sites (at positions 454, 667, 4036) which may be used for a diagnostic restriction digest. The plasmid consists of three main fragments: (1) pBR322-sequences including co1E1-origin of replication, β-lactamase-resistance-gene with the P$_{bla/p3}$ of Tn2661 (HincII-site and PstI-site removed); (2) the regulatory region with hCMV minimal promotor (−53 relative to start site) with heptamerized tet-operators upstream; and (3) the luciferase gene with 3'-flanking region from pSV-2-luc (de Wet, et al., *Mol. Cell. Biol.* 7:725–37 (1987)). See FIG. 12A for a map of pUHC 13-3, and FIGS. 12B–12F for a sequence of pUHC 13-3.

Figure 7:
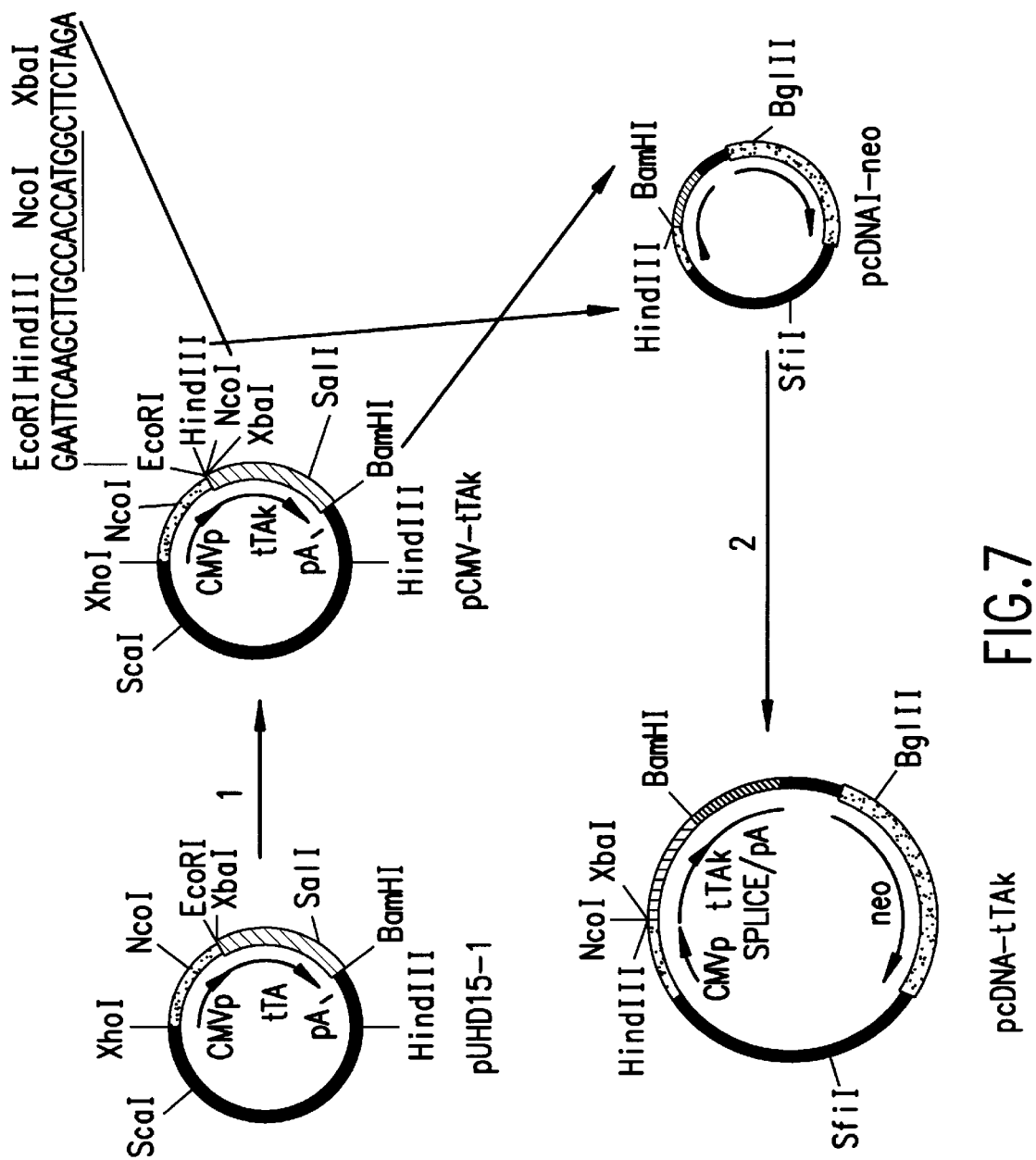
FIG. 7 is a schematic depiction of the construction of pCMV-tTAk, pcDNAI-neo, and pcDNA-tTAk (SEQ ID NO:1).
Figure 11A:
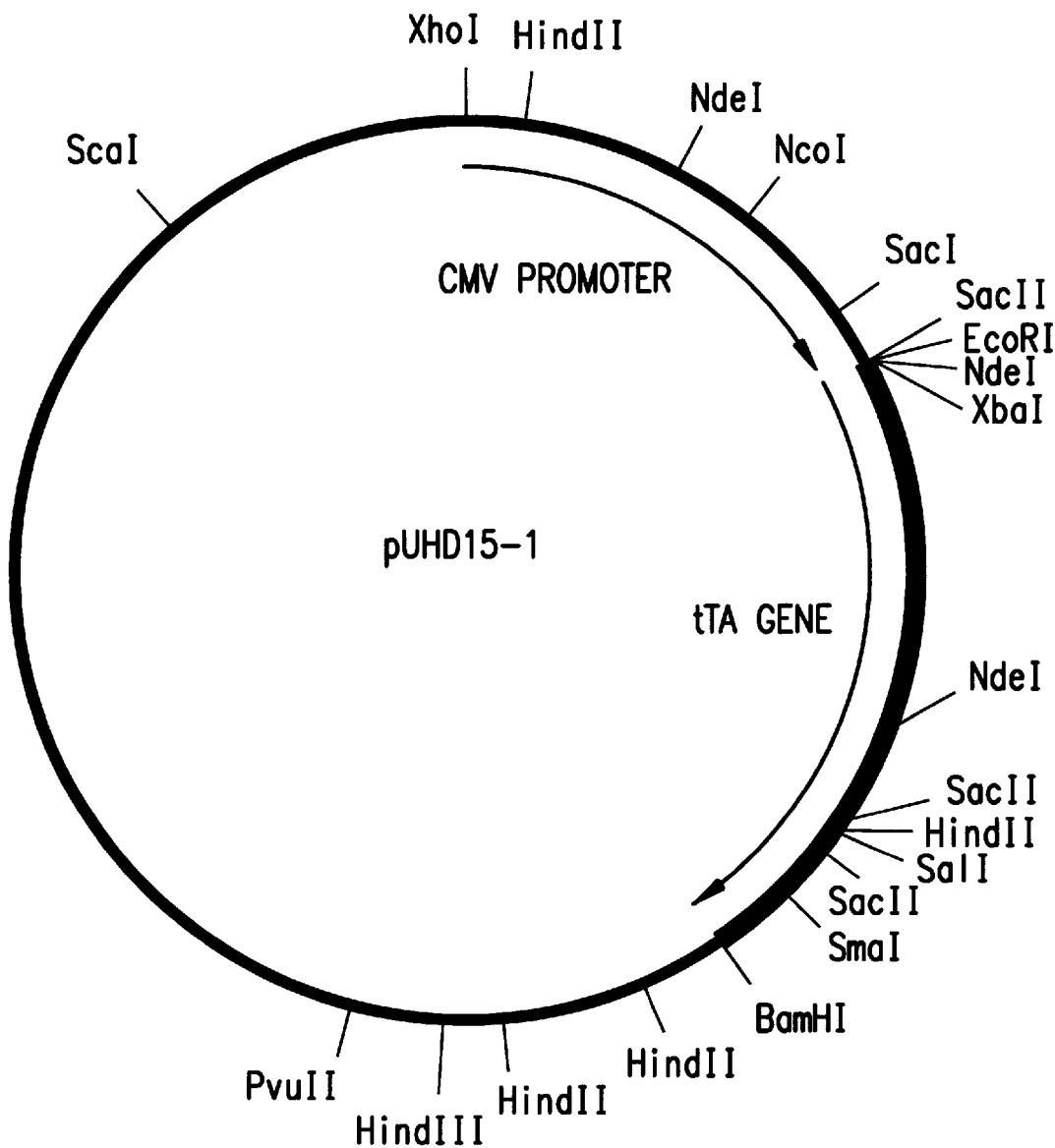
FIG. 11A depicts a restriction map of pUHD15-1.

Sequences between the EcoRI and XbaI sites of pUHD15-1 (see FIG. 11), Gossen & Bujard, *Proc. Natl. Acad. Sci. USA*:89:5547–5551 (1992), were replaced with a double-stranded oligonucleotide, whose sequence is shown in the top right of FIG. 7, to generate pCMV-tTAk (step 1). The inserted sequence provides the tTA gene with an optimal context for the initiation of translation, Kozac, M., *Nuc. Acids Res.* 12:857–872 (1984), inserts an amino acid into the tTA protein (alanine at position 2) and provides a unique HindIII site for subsequent cloning steps. This modified tTA gene is herein referred to as tTAk. The HindIII to BamHI fragment of pCMV-tTAk containing the tTAk gene was then cloned into the HindIII to BamHI sites of pcDNAI-neo (Invitrogen Corporation) to generate pcDNA-tTAk (step 2 of FIG. 7).

Figure 10A:
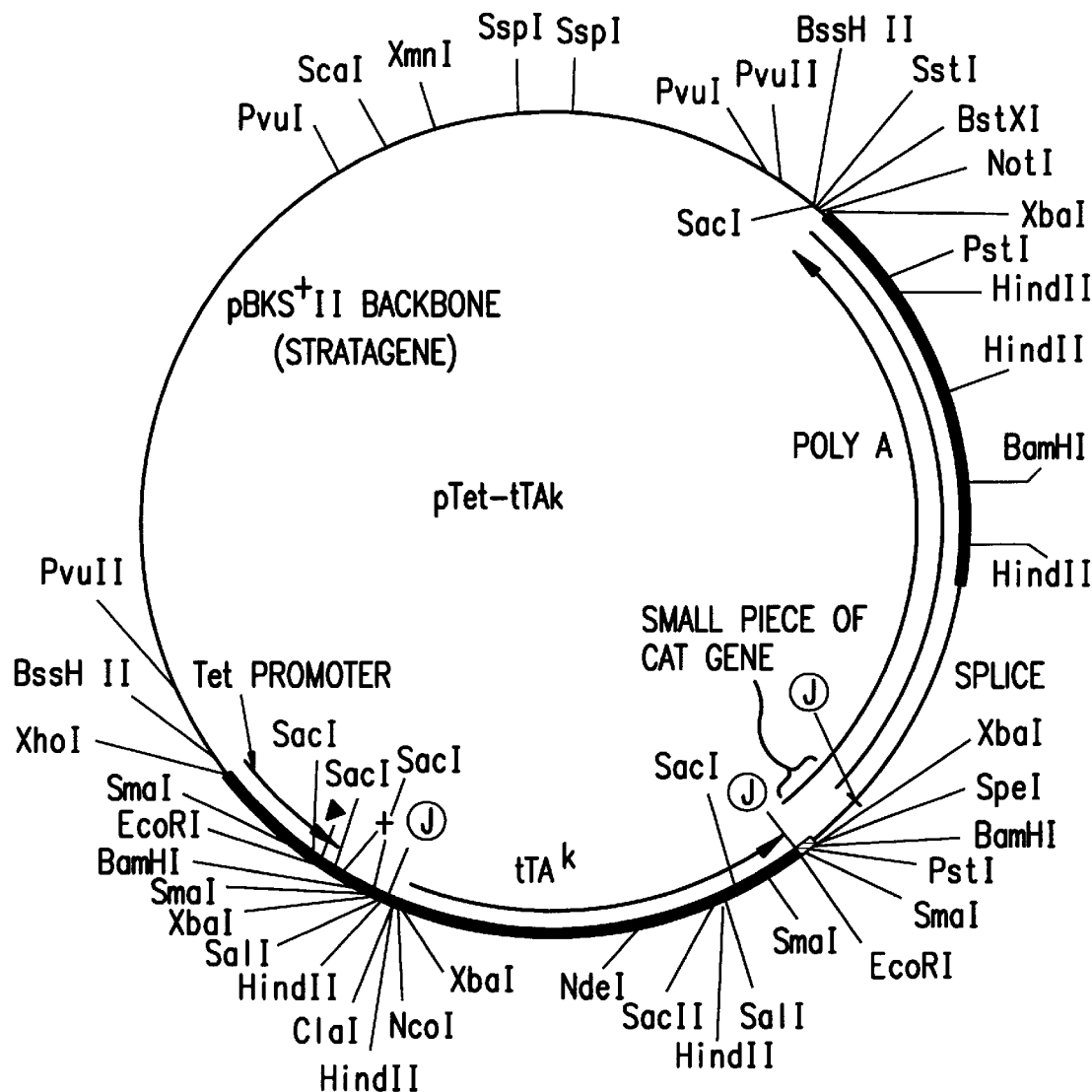
FIG. 10A depicts a restriction map of pTet-tTAk.

The plasmid pTet-tTAk places a modified tTA gene called tTAk (abbreviation used herein for the tTA gene with a consensus kozak translation initiation site inserted therein) under control of the Tet promoter of pUHC-13-3 (Gossen & Bujard, *Proc. Natl. Acad. Sci. USA*:89:5547–5551 (1992)). The construct is therefore autoregulatory.

pTet-tTAk was constructed by first constructing a vector with the Tet promoter of pUHC-13-3 in a vector with an SV40 splice and poly-A site and then inserting tTAk between the Tet promoter and the splice/poly A. The SV40 intervening sequence is derived from the small T antigen: Mbo I (0.56 mu=4100) to Mbo I (0.44 mu=4710). The SV40 poly-A sequence is SV40 from BclI (0.19 mu=2770) to EcoRI (0 mu=1782), and contains the early polyadenylation sequence and the 3' terminal sequence of the SV40 late region (coordinates given are for SV40). Just upstream of the splice region is 125 bp derived from the 3' end of the bacterial CAT gene (untranslated sequences); these sequences appear to have no harmful effect, and were included only because they provide a convenient restriction site. See FIG. 10A for a map of pTet-tTAk and FIGS. 10B–10G for the sequence of pTet-tTAk.

Figure 8:
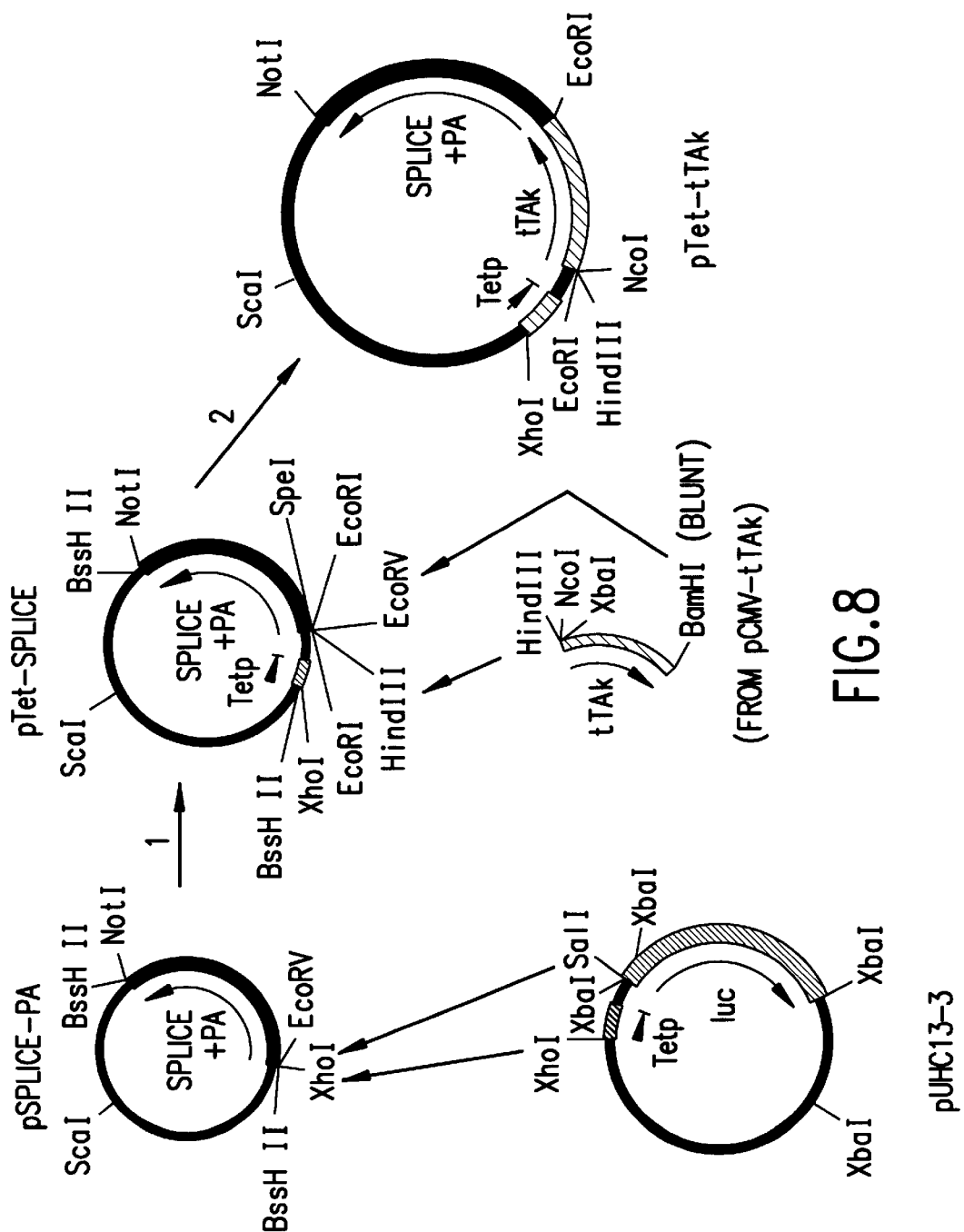
FIG. 8 is a schematic depiction of the construction of pTet-Splice and pTet-tTAk.
Figure 9A:
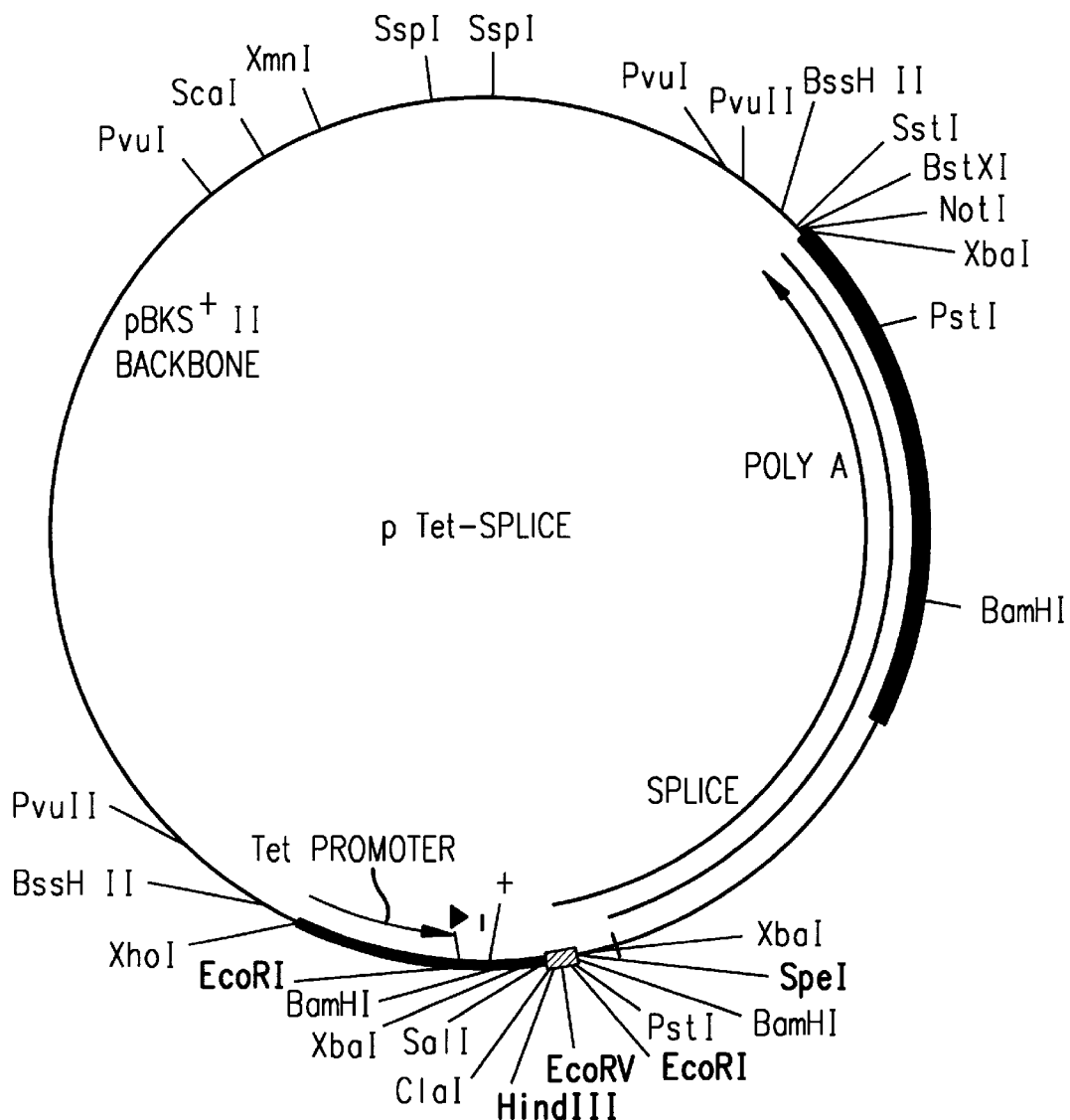
FIG. 9A depicts a restriction map of pTet-Splice. Cloning sites are shown in boldface print. Note that there are two EcoRI sites.

The starting plasmid for the construction of pTet-tTAk, pSplice-PA, was constructed by inserting the ScaI to EcoRI fragment of pHAV-CAT, Jones, et al., *Nuc. Acids Res.* 19:6547–6551 (1991), into the XbaI site of pBKSII⁺ (Stratagene) by ligation of XbaI linkers after Klenow fill in of the EcoRI site. The pSplice-PA plasmid contains the SV40 intervening sequence derived from the small T antigen and the SV40 early polyadenylation sequence, as shown in FIG. 8. The XhoI to SalI fragment of pUHC13-3, Gossen & Bujard, *Proc. Natl. Acad. Sci. USA*:89:5547–5551 (1992), which contains seven copies of the tet operator upstream of a minimal human cytomegalovirus (hCMV) promoter, was cloned into the unique XhoI site of pSplice-PA to yield pTet-Splice (FIG. 8, step 1). This tet operator-containing promoter is referred to herein as Tetp. pTet-Splice contains a number of unique restriction sites for easy insertion of genes of interest between Tetp and the splice/poly A sequences. See FIG. 9A for a map of pTet-Splice and FIGS. 9B–9G for the sequence of pTet-Splice. The HindIII to BamHI (blunted with Klenow) fragment of pCMV-tTAk containing the tTAk gene was then cloned into the HindIII to EcoRV sites of pTet-Splice to yield pTet-tTAk (FIG. 8, step 2).

The Tetp-controlled mouse RAG-1 expression construct used in these experiments was constructed by inserting the coding region of pR1A/C as a BamHI (blunted with Klenow) to XbaI fragment into the EcoRV to SpeI sites of pTet-Splice to yield pTet-R1A/C. However, the nucleic acid molecule encoding RAG-1 can be synthesized chemically using known methods in the art or can be isolated from any other source. For the complete sequence of RAG-1, see Schatz, D. G. etal., *Cell* 59:1035–1048 (1989). The RAG-1 coding region of pR1A/C has been altered, as compared to full length mouse RAG-1, by deletion of amino acids 2–89 and amino acids 1009–1040, the addition of six histidines immediately following the second codon, the insertion of alanine and serine codons immediately after the histidines to introduce a site for NheI, and the addition of a consensus translation initiation context surrounding the AUG start codon. This deletion mutant of RAG-1 has significantly greater V(D)J recombinase activity than full length mouse RAG-1.

The tetracycline-controlled mouse RAG-2 expression construct used here was constructed by inserting the XhoI to XbaI fragment of pR2A-CDM8 into the SalI to SpeI sites of pTet-Splice to yield pTet-R2A. However, the nucleic acid molecule encoding RAG-2 can be synthesized chemically using known methods in the art or can be isolated from any other available source. For the complete sequence of RAG-2, see U.S. Pat. No. 5,159,066, issued Oct. 27, 1992, or Oettinger, M. A. et al., *Science* 248:1517–1523 (1990). The RAG-2 coding region of pR2A-CDM8 has been altered, relative to full length mouse RAG-2, by the C-terminal deletion of amino acids 492–527, the addition of a consensus translation initiation context surrounding the AUG start codon, and the insertion of an alanine codon at position 2. This RAG-2 mutant has somewhat higher V(D)J recombinase activity than full length mouse RAG-2.

Example 1

Construction of plasmids

The EcoRI-BamHI fragment of pUHD15-1 (Gossen, M. & Bujard, H., *Proc. Natl. Acad. Sci. USA* 89:5547–5551 (1992)) containing the tTA open reading frame (ORF) was modified at its 5' end by addition of a 30 bp oligonucleotide (SEQ ID NO 1) to provide an optimal context for translational initiation (Kozak, M., *Nucl. Acids Res.* 12:857–872 (1984)) and a unique HindIII site for subsequent cloning. The added nucleotides are those shown at the top right, FIG. 7. The number of added nucleotides depends on whether one counts the nucleotides of the EcoRI and XbaI enzyme sites. For simplicity, the modified 5' end of the ORF is referred to herein as a 30 bp oligo. The modified tTA gene is hereafter referred to as tTAk. The HindIII-BamHI tTAk fragment was cloned into the HindIII-BamHI sites of pcDNAI-neo (Invitrogen Corporation) to yield pcDNA-tTAk. In pcDNA-tTAk, the tTAk gene is under the transcriptional control of the enhancer and promoter sequences of the immediate early gene of human cytomegalovirus (hCMV). The plasmid pSplice-PA was constructed by inserting the SV40 small T antigen intervening sequence and the SV40 early polyadenylation sequence from pHAV-CAT (Jones, S. N. et al., *Nucl. Acids Res.* 19:6547–6551 (1991)), into pBKSII⁺ (Stratagene). The XhoI-SalI fragment of pUHC13-3 (Gossen, M. & Bujard, H., *Proc. Natl. Acad. Sci. USA* 89:5547–5551 (1992)), containing seven copies of the tet operator upstream of a minimal promoter (hereafter referred to as Tetp), was cloned upstream of the splice/polyA sequences of pSplice-PA to yield pTet-Splice. The tTAk gene was cloned into pTet-Splice to yield pTet-tTAk, placing the start site of transcription 143 bases upstream of the tTAk AUG (FIG. 1).

The Tetp-controlled mouse RAG-1 expression construct (pTet-R1A/C) was constructed by inserting the coding region of pR1A/C into pTet-Splice. The RAG-1 coding region of pR1A/C has been altered, as compared to full length mouse RAG-1, by small N and C terminal deletions which result in at least a two-fold increase in V(D)J recombinase activity, i.e. two fold increase in VDJ with R1A/C over R1A and R2A over R2. The Tetp-controlled mouse RAG-2 expression construct (pTet-R2A) was constructed by inserting the coding region of pR2A-CDM8 into pTet-Splice. This RAG-2 coding region is altered relative to full length mouse RAG-2 by a small C-terminal deletion which results in a small increase in V(D)J recombinase activity. pTet-R1 and pTet-R2 consist of the complete RAG-1 and RAG-2 ORFs, respectively, inserted into pTet-splice.

Example 2

Cell culture and derivation of transfected cell lines

Stable transfectants of pcDNA-tTAk were generated by calcium phosphate/glycerol shock transfection of 10 μg of linearized plasmid into 0.5×10⁶ NIH 3T3 fibroblast cells as described (Schatz, D. G. et al., *Cell* 59:1035–1048 (1989)) and 48 hours after transfection plating cells in 0.75 mg/ml G418 plus 0.5 μg/ml tetracycline. Single colonies picked after 12 days were expanded in 0.5 mg/ml G418, 0.5 μg/ml tetracycline.

Stable transfectants of pTet-tTAk alone or pTet-tTAk plus pTet-R1A/C plus pTet-R2A, were generated by transfecting 10 μg of each linearized plasmid with 1 μg of linearized pSV2-His, followed by selection in media containing L-histidinol but lacking histidine as described previously (Schatz, D. G. et al., *Cell* 59:1035–1048 (1989)). Transfected cells were maintained in the presence of 0.5 μg/ml tetracycline, beginning at the time of transfection.

Example 3

Assay for V(D)J recombinase activity

V(D)J recombinase activity was measured using the extrachromosomal reporter plasmid pD243 (a signal joint deletion substrate) as described by others (Lewis, S. M. & Hesse, J. E., *EMBO J*. 10(12):3631–3639 (1991)). Briefly, NIH3T3 fibroblast cell lines were transfected with 10 μg of pD243, and where indicated 6 μg of pTet-R1A/C and 4.8 μg of pTet-R2A, by the calcium phosphate/glycerol shock transfection method. Tetracycline was omitted from the culture medium after the transfection in the samples indicated "tet⁻". In other cases ("tet⁺"), cells were maintained in media containing 0.5 μg/ml tetracycline. Extrachromosomal plasmid molecules were harvested by rapid alkaline lysis of the cells 48 hours after transfection, and a small aliquot of the isolated DNA was electroporated into MC1061 bacteria. The electroporated bacteria were spread on LB agar plates containing 100 μg/ml ampicillin (A) and on plates containing 11 μg/ml chloramphenicol and 100 μg/ml ampicillin (CA). After sixteen hours of growth at 37° C. the percent recombination, Rn, was calculated as the total number of CA resistant colonies divided by the total number of A resistant colonies, multiplied by 100. Greater than 99% of plasmids harvested from NIH3T3 fibroblasts 48 hours after transfection have replicated at least once (as indicated by their resistance to digestion by DpnI), demonstrating that essentially all of the harvested plasmid molecules have entered the nucleus of transfected cells and are therefore assumed to have been accessible for recombination (Lieber, M. R. et al., *Genes and Devel*. 1:751–761 (1987)).

Example 4

RNA blot analysis

Electrophoresis of total cell RNA in 1–1.2% agarose/formaldehyde gels was followed by blotting to nylon membranes (Zetabind, CUNO or Genescreen Plus, NEN) and subsequent hybridization with DNA probes prepared using a random hexamer labelling kit (Boehringer Mannheim). Probes detecting RAG-1 and RAG-2 mRNA were prepared from fragments of the RAG-1 or RAG-2 coding regions (Schatz, D. G. et al., *Cell* 59:1035–1048 (1989); Oettinger, M. A. et al., *Science* 248:1517–1523 (1990)), respectively. The probe for actin has been described previously (Schatz, D. G. et al., *Cell* 59:1035–1048 (1989)).

Example 5

Western blot analysis

Protein from $1.5 \times 10^7$ cells per lane was subjected to SDS-PAGE on an 8% polyacrylamide gel and electroblotted to a 0.2 micron PVDF membrane (BIO-RAD Laboratories). Membranes were blocked at room temperature (RT) overnight in a solution of 1% BSA, 0.5% gelatin, in TTBS (Tris buffered saline+0.1% Tween-20), washed 2×5 minutes in TTBS and probed overnight with a monoclonal anti-tet R antibody (9F10)-containing hybridoma supernatant (S. Freundlieb and H. Bujard, Heidelberg, Germany), diluted 1:4 in 1% BSA in TTBS. The blots were washed 4×10 minutes in TTBS and tTA protein was detected by incubation for 40 minutes with goat anti-mouse antibody (1:10,000 in TTBS) (Amersham), washing in TTBS 4×10 minutes and TBS 2×10 minutes, and subsequent developing with an ECL western blotting kit (Amersham).

Example 6

Transgenic mice and assays for luciferase

Mice doubly transgenic for pTet-tTAk (XhoI to NotI fragment) and pUHC13-3 (XhoI to AseI fragment) were created by co-microinjection of gel purified DNA (in the presence of 0.5 μg/ml tetracycline) into fertilized F1 (C57BL/6×C3H) eggs, which were then implanted into the uterus of pseudopregnant females. Pregnant females were provided with water containing 100 μg/ml tetracycline and 5% sucrose. Progeny were screened by probing Southern blots of tail DNA with tTA (761 bp XbaI-SalI) or luciferase (1365 bp HindIII-EcoRV) fragments labeled with α-$^{32}$P-dCTP as above. Transgene copy number was estimated by comparison of the Southern blot signal to those obtained from dilutions of plasmid DNA fragments.

Luciferase activity in tissues of transgenic mice was measured using an assay system according to the manufacturers instructions (#E1500, Promega Corporation). Peripheral blood mononuclear cells (PBMCs) ($0.1–1.0 \times 10^6$ cells) were lysed in 50 μl of lysis buffer for 15 minutes at room temperature, and after pelleting the insoluble material for 5 seconds at 14,000 rpm, 20 μl of the supernatant was mixed with 100 μl of luciferin reagent and the light produced in 10 seconds was measured in a luminometer (Berthold, Lumat LB9501, Germany). The number of cell equivalents of lysate in the assay was used to normalize luciferase activity between samples. Other tissues, harvested and quick frozen in liquid nitrogen, were ground to a powder with a cold mortar and pestle, placed in 100–200 μl luciferase lysis buffer, and incubated at RT for 15 minutes. Cell debris was pelleted for 10 seconds at 14,000 rpm and supernatant was stored at −70° C. until analysis. 20 μl supernatant was used in luciferase assays. For normalization of luciferase activity between tissue lysates, total protein concentration in lysates was determined using a Bradford protein assay (Bio-Rad Laboratories). Samples were assayed within the linear range of the assay and only approximately 2-fold variation was observed as lysates were diluted. Firefly luciferase protein standard (Sigma) added to extracts from a variety of tissues from wild type mice showed no variation in activity.

While the foregoing invention has been described in some detail for purposes of clarity and understanding, it will be appreciated by one skilled in the art from a reading of this disclosure that various changes in form and detail can be made without departing from the true scope of the invention and appended claims. All patents and publications mentioned herein are incorporated by reference in their entirety.

---

What is claimed is:

1. A polynucleotide comprising a nucleotide sequence encoding a tetracycline transactivator fusion protein, said protein comprising a prokaryotic tet repressor and a eucaryotic transcriptional activator protein, and said polynucleotide molecule being operably linked to an inducible minimal promoter, which promoter contains at least one tet operator sequence.

2. The polynucleotide molecule as claimed in claim 1, wherein the open reading frame of the polynucleotide molecule encoding the tetracycline transactivator fusion protein is modified at its 5' end to provide an optimal context for translational initiation.

3. The polynucleotide molecule as claimed in claim 1 which is DNA.

4. The polynucleotide molecule as claimed in claim 2, wherein the 5' end of the open reading frame of the polynucleotide molecule encoding the tetracycline transactivator fusion protein is further modified to provide a unique restriction site.

5. A cloning or expression vector comprising the polynucleotide molecule of any one of claims 1,2 or 4.

6. A eucaryotic cell comprising the polynucleotide molecule of any one of claims 1,2 or 4.

7. A host cell comprising the polynucleotide molecule of any of claims 1,2 or 4.

8. The polynucleotide molecule as claimed in claim 4, wherein the unique restriction site is HindIII.

9. The vector of claim 5, wherein said vector is pTet-Splice.

10. The vector of claim 5, wherein said vector is pTet-tTAk.

11. A host cell comprising the vector of claim 5.

12. The vector as claimed in claim 5, wherein said vector is a plasmid.

13. The eucaryotic cell as claimed in claim 6, wherein said eucaryotic cell further comprises a polynucleotide molecule encoding a heterologous protein operably linked to an inducible minimal promoter, which promoter contains at least one tet operator sequence.

14. The eucaryotic cell as claimed in claim 6, which further comprises tetracycline or a tetracycline analogue in an amount sufficient to suppress binding of tetracycline transactivator fusion protein to said inducible minimal promoter.

15. The host cell as claimed in claim 7, wherein said host cell further comprises a polynucleotide molecule encoding a heterologous protein operably linked to an inducible minimal promoter, which promoter contains at least one tet operator sequence.

16. The polynucleotide molecule as claimed in claim 8, wherein the open reading frame of the polynucleotide molecule encoding the tetracycline transactivator fusion protein is modified at its 5' end to comprise the nucleotide sequence identified as SEQ ID NO 1.

17. The eucaryotic cell as claimed in claim 13, wherein at least one of the polynucleotide molecules is operably linked to a minimal promoter and seven tet operator sequences.

18. The eucaryotic cell as claimed in claim 13, wherein the polynucleotide molecule encoding a tetracycline transactivator fusion protein is expressed in an amount sufficient to enhance expression of the polynucleotide molecule, encoding the heterologous protein, in the absence of tetracycline or a tetracycline analogue.

19. The eucaryotic cell as claimed in claim 13 wherein the tetracycline transactivator fusion protein is present in an amount sufficient to enhance expression of the heterologous protein.

20. The eucaryotic cell as claimed in claim 13, wherein the polynucleotide molecule encoding a tetracycline transactivator fusion protein is expressed in an amount sufficient to activate expression of the polynucleotide molecule, encoding the heterologous protein, in the absence of tetracycline or a tetracycline analogue.

21. The eucaryotic cell as claimed in claim 13 wherein the tetracycline transactivator fusion protein is present in an amount sufficient to activate expression of the heterologous protein.

22. The host cell as claimed in claim 15, wherein at least one of the polynucleotide molecules is operably linked to a minimal promoter and seven tet operator sequences.

23. A method to inhibit expression of a heterologous protein in a eucaryotic cell comprising
(a) obtaining a eucaryotic cell comprising
(i) a first polynucleotide molecule encoding a tetracyline transactivator fusion protein, said protein comprising a procaryotic tet repressor and a eucaryotic transcriptional activator protein, and said polynucleotide molecule being operably linked to an inducible minimal promoter, which promoter contains at least one tet operator sequence;
(ii) a second polynucleotide molecule encoding the heterologous protein, said second polynucleotide molecule being operably linked to an inducible minimal promoter, and said promoter containing at least one tet operator sequence; and
(b) cultivating the eucaryotic cell in a medium comprising tetracycline or a tetracycline analogue such that expression of the heterologous protein is inhibited.

24. The method as claimed in claim 23, wherein the second polynucleotide molecule is operably linked to a minimal promoter and seven tet operator sequences.

25. A method to enhance the expression of a heterologous protein in a eucaryotic cell comprising
(a) obtaining a eucaryotic cell comprising
(i) a first polynucleotide molecule encoding a tetracycline transactivator fusion protein, said protein comprising a prokaryotic tet repressor and a eucaryotic transcriptional activator protein, and said polynucleotide molecule being operably linked to an inducible minimal promoter, which promoter contains at least one tet operator sequence;
(ii) a second polynucleotide molecule encoding the heterologous protein, said second polynucleotide molecule being operably linked to an inducible minimal promoter, and said promoter containing at least one tet operator sequence; and
(b) cultivating the eucaryotic cell in a medium lacking tetracycline or a tetracycline analogue such that expression of the heterologous protein is enhanced.

26. A method to activate the expression of a heterologous protein in a eucaryotic cell comprising
(a) obtaining a eucaryotic cell comprising
(i) a first polynucleotide molecule encoding a tetracycline transactivator fusion protein, said protein comprising a prokaryotic tet repressor and a eucaryotic transcriptional activator protein, and said polynucleotide molecule being operably linked to an inducible minimal promoter, which promoter contains at least one tet operator sequence;
(ii) a second polynucleotide molecule encoding the heterologous protein, said second polynucleotide molecule being operably linked to an inducible minimal promoter, and said promoter containing at least one tet operator sequence; and
(b) cultivating the eucaryotic cell in a medium lacking tetracycline or a tetracycline analogue such that expression of the heterologous protein is activated.

27. A kit comprising a carrier means having in close confinement therein at least two container means, wherein a first container means contains a first polynucleotide molecule encoding a tetracycline transactivator fusion protein, said protein comprising a procaryotic tet repressor and a eucaryotic transcriptional activator protein, and said polynucleotide molecule being operably linked to an inducible minimal promoter, which promoter contains at least one tet operator sequence; and a second container means contains a second polynucleotide molecule encoding said inducible minimal promoter, which promoter contains at least one tet operator sequence, which tet operator sequence is strategically positioned for being operably linked to a heterologous polynucleotide sequence encoding a polypeptide.

28. A kit comprising a carrier means having in close confinement therein at least two container means, wherein a first container means contains a eucaryotic cell transfected with a first polynucleotide molecule encoding a tetracycline transactivator fusion protein, said protein comprising a procaryotic tet repressor and a eucaryotic transcriptional activator protein, and said polynucleotide molecule being operably linked to an inducible minimal promoter, which promoter contains at least one tet operator sequence; and a second container means contains a second polynucleotide molecule comprising an inducible minimal promoter, which promoter contains at least one tet operator sequence, which tet operator sequence is strategically positioned for being operably linked to a heterologous polynucleotide sequence encoding a heterologous polypeptide.

* * * * *

UNITED STATES PATENT AND TRADEMARK OFFICE
CERTIFICATE OF CORRECTION

PATENT NO. : 5,851,796
DATED : Dec. 22, 1998
INVENTOR(S) : David Schatz

It is certified that error appears in the above-identified patent and that said Letters Patent is hereby corrected as shown below:

Column 1, after the title insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Thirteenth Day of April, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:1:

```
GAATTCAAGC  TTGCCACCAT  GGCTTCTAGA                                                    30
```

( 2 ) INFORMATION FOR SEQ ID NO:2:

( i ) SEQUENCE CHARACTERISTICS:
        ( A ) LENGTH: 5178 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:2:

```
CTAAATTGTA  AGCGTTAATA  TTTTGTTAAA  ATTCGCGTTA  AATTTTGTT   AAATCAGCTC    60
ATTTTTTAAC  CAATAGGCCG  AAATCGGCAA  AATCCCTTAT  AAATCAAAAG  AATAGACCGA   120
GATAGGGTTG  AGTGTTGTTC  CAGTTTGGAA  CAAGAGTCCA  CTATTAAAGA  ACGTGGACTC   180
CAACGTCAAA  GGGCGAAAAA  CCGTCTATCA  GGGCGATGGC  CCACTACGTG  AACCATCACC   240
CTAATCAAGT  TTTTTGGGGT  CGAGGTGCCG  TAAAGCACTA  AATCGGAACC  CTAAAGGGAG   300
CCCCCGATTT  AGAGCTTGAC  GGGGAAAGCC  GGCGAACGTG  GCGAGAAAGG  AAGGGAAGAA   360
AGCGAAAGGA  GCGGGCGCTA  GGGCGCTGGC  AAGTGTAGCG  GTCACGCTGC  GCGTAACCAC   420
CACACCCGCC  GCGCTTAATG  CGCCGCTACA  GGGCGCGTCC  CATTCGCCAT  TCAGGCTGCG   480
CAACTGTTGG  GAAGGGCGAT  CGGTGCGGGC  CTCTTCGCTA  TTACGCCAGC  TGGCGAAAGG   540
GGGATGTGCT  GCAAGGCGAT  TAAGTTGGGT  AACGCCAGGG  TTTTCCCAGT  CACGACGTTG   600
TAAAACGACG  GCCAGTGAGC  GCGCGTAATA  CGACTCACTA  TAGGGCGAAT  TGGAGCTCCA   660
CCGCGGTGGC  GGCCGCTCTA  GAGCAATTCC  TTTGCCTAAT  TTAAATGAGG  ACTTAACCTG   720
TGGAAATATT  TTGATGTGGG  AAGCTGTTAC  TGTTAAAACT  GAGGTTATTG  GGGTAACTGC   780
TATGTTAAAC  TTGCATTCAG  GGACACAAAA  AACTCATGAA  AATGGTGCTG  GAAAACCCAT   840
TCAAGGGTCA  AATTTTCATT  TTTTGCTGT   TGGTGGGGAA  CCTTGGAGC   TGCAGGGTGT   900
GTTAGCAAAC  TACAGGACCA  AATATCCTGC  TCAAACTGTA  ACCCCAAAAA  ATGCTACAGT   960
TGACAGTCAG  CAGATGAACA  CTGACCACAA  GGCTGTTTTG  GATAAGGATA  ATGCTTATCC  1020
AGTGGAGTGC  TGGGTTCCTG  ATCCAAGTAA  AAATGAAAAC  ACTAGATATT  TTGGAACCTA  1080
CACAGGTGGG  GAAAATGTGC  CTCCTGTTTT  GCACATTACT  AACACAGCAA  CCACAGTGCT  1140
```

```
TCTTGATGAG CAGGGTGTTG GGCCCTTGTG CAAAGCTGAC AGCTTGTATG TTTCTGCTGT    1200
TGACATTTGT GGGCTGTTTA CCAACACTTC TGGAACACAG CAGTGGAAGG GACTTCCCAG    1260
ATATTTTAAA ATTACCCTTA GAAAGCGGTC TGTGAAAAAC CCCTACCCAA TTTCCTTTTT    1320
GTTAAGTGAC CTAATTAACA GGAGGACACA GAGGGTGGAT GGGCAGCCTA TGATTGGAAT    1380
GTCCTCTCAA GTAGAGGAGG TTAGGGTTTA TGAGGACACA GAGGAGCTTC CTGGGGATCC    1440
AGACATGATA AGATACATTG ATGAGTTTGG ACAAACCACA ACTAGAATGC AGTGAAAAAA    1500
ATGCTTTATT TGTGAAATTT GTGATGCTAT TGCTTTATTT GTAACCATTA TAAGCTGCAA    1560
TAAACAAGTT AACAACAACA ATTGCATTCA TTTTATGTTT CAGGTTCAGG GGGAGGTGTG    1620
GGAGGTTTTT TAAAGCAAGT AAAACCTCTA CAAATGTGGT ATGGCTGATT ATGATCTTTG    1680
TGAAGGAACC TTACTTCTGT GGTGTGACAT AATTGGACAA ACTACCTACA GAGATTTAAA    1740
GCTCTAAGGT AAATATAAAA TTTTAAGTG TATAATGTGT TAAACTACTG ATTCTAATTG    1800
TTTGTGTATT TTAGATTCCA ACCTATGGAA CTGATGAATG GGAGCAGTGG TGGAATGCCT    1860
TTAATGAGGA AAACCTGTTT TGCTCAGAAG AAATGCCATC TAGTGATGAT GAGGCTACTG    1920
CTGACTCTCA ACATTCTACT CCTCCAAAAA AGAAGAGAAA GGTAGAAGAC CCCAAGGACT    1980
TTCCTTCAGA ATTGCTAAGT TTTTGAGTC ATGCTGTGTT TAGTAATAGA ACTCTTGCTT    2040
GCTTTGCTAT TTACACCACA AAGGAAAAAG CTGCACTGCT ATACAAGAAA ATTATGGAAA    2100
AATATTCTGT AACCTTTATA AGTAGGCATA ACAGTTATAA TCATAACATA CTGTTTTTTC    2160
TTACTCCACA CAGGCATAGA GTGTCTGCTA TTAATAACTA TGCTCAAAAA TTGTGTACCT    2220
TTAGCTTTTT AATTTGTAAA GGGGTTAATA AGGAATATTT GATGTATAGT GCCTTGACTA    2280
GAGATCCGCC TCCGGCGAAT TTCTGCCATT CATCCGCTTA TTATCACTTA TTCAGGCGTA    2340
GCACCAGGCG TTTAAGGGCA CCAATAACTG CCTTAAAAAA ATTACGCCCC GCCCTGCCAC    2400
TCATCGCAGT GCTCTAGAAC TAGTGGATCC CCCGGGCTGC AGGAATTCGA TATCAAGCTT    2460
ATCGATACCG TCGACCTCGA CTCTAGAGGA TCCCCGGGTA CCGAGCTCGA ATTCGGGGCC    2520
GCGGAGGCTG GATCGGTCCC GGTGTCTTCT ATGGAGGTCA AAACAGCGTG GATGGCGTCT    2580
CCAGGCGATC TGACGGTTCA CTAAACGAGC TCTGCTTATA TAGGCCTCCC ACCGTACACG    2640
CCTACTCGAC CCGGGTACCG AGCTCGACTT TCACTTTTCT CTATCACTGA TAGGGAGTGG    2700
TAAACTCGAC TTTCACTTTT CTCTATCACT GATAGGGAGT GGTAAACTCG ACTTTCACTT    2760
TTCTCTATCA CTGATAGGGA GTGGTAAACT CGACTTTCAC TTTTCTCTAT CACTGATAGG    2820
GAGTGGTAAA CTCGACTTTC ACTTTTCTCT ATCACTGATA GGGAGTGGTA AACTCGACTT    2880
TCACTTTTCT CTATCACTGA TAGGGAGTGG TAAACTCGAC TTTCACTTTT CTCTATCACT    2940
GATAGGGAGT GGTAAACTCG AGGGGGGGCC CGGTACCCAG CTTTTGTTCC CTTTAGTGAG    3000
GGTTAATTGC GCGCTTGGCG TAATCATGGT CATAGCTGTT TCCTGTGTGA AATTGTTATC    3060
CGCTCACAAT TCCACACAAC ATACGAGCCG GAAGCATAAA GTGTAAAGCC TGGGGTGCCT    3120
AATGAGTGAG CTAACTCACA TTAATTGCGT TGCGCTCACT GCCCGCTTTC CAGTCGGGAA    3180
ACCTGTCGTG CCAGCTGCAT TAATGAATCG GCCAACGCGC GGGGAGAGGC GGTTTGCGTA    3240
TTGGGCGCTC TTCCGCTTCC TCGCTCACTG ACTCGCTGCG CTCGGTCGTT CGGCTGCGGC    3300
GAGCGGTATC AGCTCACTCA AAGGCGGTAA TACGGTTATC CACAGAATCA GGGGATAACG    3360
CAGGAAAGAA CATGTGAGCA AAAGGCCAGC AAAAGGCCAG GAACCGTAAA AAGGCCGCGT    3420
TGCTGGCGTT TTTCCATAGG CTCCGCCCCC CTGACGAGCA TCACAAAAAT CGACGCTCAA    3480
GTCAGAGGTG GCGAAACCCG ACAGGACTAT AAAGATACCA GGCGTTTCCC CCTGGAAGCT    3540
```

| | | | | | | |
|---|---|---|---|---|---|---|
| CCCTCGTGCG | CTCTCCTGTT | CCGACCCTGC | CGCTTACCGG | ATACCTGTCC | GCCTTTCTCC | 3600 |
| CTTCGGGAAG | CGTGGCGCTT | TCTCATAGCT | CACGCTGTAG | GTATCTCAGT | TCGGTGTAGG | 3660 |
| TCGTTCGCTC | CAAGCTGGGC | TGTGTGCACG | AACCCCCGT | TCAGCCCGAC | CGCTGCGCCT | 3720 |
| TATCCGGTAA | CTATCGTCTT | GAGTCCAACC | CGGTAAGACA | CGACTTATCG | CCACTGGCAG | 3780 |
| CAGCCACTGG | TAACAGGATT | AGCAGAGCGA | GGTATGTAGG | CGGTGCTACA | GAGTTCTTGA | 3840 |
| AGTGGTGGCC | TAACTACGGC | TACACTAGAA | GGACAGTATT | TGGTATCTGC | GCTCTGCTGA | 3900 |
| AGCCAGTTAC | CTTCGGAAAA | AGAGTTGGTA | GCTCTTGATC | CGGCAAACAA | ACCACCGCTG | 3960 |
| GTAGCGGTGG | TTTTTTTGTT | TGCAAGCAGC | AGATTACGCG | CAGAAAAAAA | GGATCTCAAG | 4020 |
| AAGATCCTTT | GATCTTTTCT | ACGGGGTCTG | ACGCTCAGTG | GAACGAAAAC | TCACGTTAAG | 4080 |
| GGATTTTGGT | CATGAGATTA | TCAAAAGGA | TCTTCACCTA | GATCCTTTTA | AATTAAAAAT | 4140 |
| GAAGTTTTAA | ATCAATCTAA | AGTATATATG | AGTAAACTTG | GTCTGACAGT | TACCAATGCT | 4200 |
| TAATCAGTGA | GGCACCTATC | TCAGCGATCT | GTCTATTTCG | TTCATCCATA | GTTGCCTGAC | 4260 |
| TCCCCGTCGT | GTAGATAACT | ACGATACGGG | AGGGCTTACC | ATCTGGCCCC | AGTGCTGCAA | 4320 |
| TGATACCGCG | AGACCCACGC | TCACCGGCTC | CAGATTTATC | AGCAATAAAC | CAGCCAGCCG | 4380 |
| GAAGGGCCGA | GCGCAGAAGT | GGTCCTGCAA | CTTTATCCGC | CTCCATCCAG | TCTATTAATT | 4440 |
| GTTGCCGGGA | AGCTAGAGTA | AGTAGTTCGC | CAGTTAATAG | TTTGCGCAAC | GTTGTTGCCA | 4500 |
| TTGCTACAGG | CATCGTGGTG | TCACGCTCGT | CGTTTGGTAT | GGCTTCATTC | AGCTCCGGTT | 4560 |
| CCCAACGATC | AAGGCGAGTT | ACATGATCCC | CCATGTTGTG | CAAAAAAGCG | GTTAGCTCCT | 4620 |
| TCGGTCCTCC | GATCGTTGTC | AGAAGTAAGT | TGGCCGCAGT | GTTATCACTC | ATGGTTATGG | 4680 |
| CAGCACTGCA | TAATTCTCTT | ACTGTCATGC | CATCCGTAAG | ATGCTTTTCT | GTGACTGGTG | 4740 |
| AGTACTCAAC | CAAGTCATTC | TGAGAATAGT | GTATGCGGCG | ACCGAGTTGC | TCTTGCCCGG | 4800 |
| CGTCAATACG | GGATAATACC | GCGCCACATA | GCAGAACTTT | AAAAGTGCTC | ATCATTGGAA | 4860 |
| AACGTTCTTC | GGGGCGAAAA | CTCTCAAGGA | TCTTACCGCT | GTTGAGATCC | AGTTCGATGT | 4920 |
| AACCCACTCG | TGCACCCAAC | TGATCTTCAG | CATCTTTTAC | TTTCACCAGC | GTTTCTGGGT | 4980 |
| GAGCAAAAAC | AGGAAGGCAA | AATGCCGCAA | AAAAGGGAAT | AAGGGCGACA | CGGAAATGTT | 5040 |
| GAATACTCAT | ACTCTTCCTT | TTTCAATATT | ATTGAAGCAT | TTATCAGGGT | TATTGTCTCA | 5100 |
| TGAGCGGATA | CATATTTGAA | TGTATTTAGA | AAAATAAACA | AATAGGGGTT | CCGCGCACAT | 5160 |
| TTCCCCGAAA | AGTGCCAC | | | | | 5178 |

(2) INFORMATION FOR SEQ ID NO:3:

(i) SEQUENCE CHARACTERISTICS:
        (A) LENGTH: 6206 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: complement (2469..3476)

(xi) SEQUENCE DESCRIPTION: SEQ ID NO:3:

| | | | | | | |
|---|---|---|---|---|---|---|
| CTAAATTGTA | AGCGTTAATA | TTTTGTTAAA | ATTCGCGTTA | AATTTTGTT | AAATCAGCTC | 60 |
| ATTTTTTAAC | CAATAGGCCG | AAATCGGCAA | AATCCCTTAT | AAATCAAAAG | AATAGACCGA | 120 |
| GATAGGGTTG | AGTGTTGTTC | CAGTTTGGAA | CAAGAGTCCA | CTATTAAAGA | ACGTGGACTC | 180 |

```
CAACGTCAAA  GGGCGAAAAA  CCGTCTATCA  GGGCGATGGC  CCACTACGTG  AACCATCACC     240

CTAATCAAGT  TTTTTGGGGT  CGAGGTGCCG  TAAAGCACTA  AATCGGAACC  CTAAAGGGAG     300

CCCCCGATTT  AGAGCTTGAC  GGGGAAAGCC  GGCGAACGTG  GCGAGAAAGG  AAGGGAAGAA     360

AGCGAAAGGA  GCGGGCGCTA  GGGCGCTGGC  AAGTGTAGCG  GTCACGCTGC  GCGTAACCAC     420

CACACCCGCC  GCGCTTAATG  CGCCGCTACA  GGGCGCGTCC  CATTCGCCAT  TCAGGCTGCG     480

CAACTGTTGG  GAAGGGCGAT  CGGTGCGGGC  CTCTTCGCTA  TTACGCCAGC  TGGCGAAAGG     540

GGGATGTGCT  GCAAGGCGAT  TAAGTTGGGT  AACGCCAGGG  TTTTCCCAGT  CACGACGTTG     600

TAAAACGACG  GCCAGTGAGC  GCGCGTAATA  CGACTCACTA  TAGGGCGAAT  TGGAGCTCCA     660

CCGCGGTGGC  GGCCGCTCTA  GAGCAATTCC  TTTGCCTAAT  TTAAATGAGG  ACTTAACCTG     720

TGGAAATATT  TTGATGTGGG  AAGCTGTTAC  TGTTAAAACT  GAGGTTATTG  GGGTAACTGC     780

TATGTTAAAC  TTGCATTCAG  GGACACAAAA  AACTCATGAA  AATGGTGCTG  GAAAACCCAT     840

TCAAGGGTCA  AATTTTCATT  TTTTGCTGT  TGGTGGGGAA  CCTTTGGAGC  TGCAGGGTGT     900

GTTAGCAAAC  TACAGGACCA  AATATCCTGC  TCAAACTGTA  ACCCCAAAAA  ATGCTACAGT     960

TGACAGTCAG  CAGATGAACA  CTGACCACAA  GGCTGTTTTG  GATAAGGATA  ATGCTTATCC    1020

AGTGGAGTGC  TGGGTTCCTG  ATCCAAGTAA  AAATGAAAAC  ACTAGATATT  TTGGAACCTA    1080

CACAGGTGGG  GAAAATGTGC  CTCCTGTTTT  GCACATTACT  AACACAGCAA  CCACAGTGCT    1140

TCTTGATGAG  CAGGGTGTTG  GGCCCTTGTG  CAAAGCTGAC  AGCTTGTATG  TTTCTGCTGT    1200

TGACATTTGT  GGGCTGTTTA  CCAACACTTC  TGGAACACAG  CAGTGGAAGG  GACTTCCCAG    1260

ATATTTTAAA  ATTACCCTTA  GAAAGCGGTC  TGTGAAAAAC  CCCTACCCAA  TTTCCTTTTT    1320

GTTAAGTGAC  CTAATTAACA  GGAGGACACA  GAGGGTGGAT  GGGCAGCCTA  TGATTGGAAT    1380

GTCCTCTCAA  GTAGAGGAGG  TTAGGGTTTA  TGAGGACACA  GAGGAGCTTC  CTGGGGATCC    1440

AGACATGATA  AGATACATTG  ATGAGTTTGG  ACAAACCACA  ACTAGAATGC  AGTGAAAAAA    1500

ATGCTTTATT  TGTGAAATTT  GTGATGCTAT  TGCTTTATTT  GTAACCATTA  TAAGCTGCAA    1560

TAAACAAGTT  AACAACAACA  ATTGCATTCA  TTTTATGTTT  CAGGTTCAGG  GGGAGGTGTG    1620

GGAGGTTTTT  TAAAGCAAGT  AAAACCTCTA  CAAATGTGGT  ATGGCTGATT  ATGATCTTTG    1680

TGAAGGAACC  TTACTTCTGT  GGTGTGACAT  AATTGGACAA  ACTACCTACA  GAGATTTAAA    1740

GCTCTAAGGT  AAATATAAAA  TTTTTAAGTG  TATAATGTGT  TAAACTACTG  ATTCTAATTG    1800

TTTGTGTATT  TTAGATTCCA  ACCTATGGAA  CTGATGAATG  GGAGCAGTGG  TGGAATGCCT    1860

TTAATGAGGA  AAACCTGTTT  TGCTCAGAAG  AAATGCCATC  TAGTGATGAT  GAGGCTACTG    1920

CTGACTCTCA  ACATTCTACT  CCTCCAAAAA  AGAAGAGAAA  GGTAGAAGAC  CCCAAGGACT    1980

TTCCTTCAGA  ATTGCTAAGT  TTTTTGAGTC  ATGCTGTGTT  TAGTAATAGA  ACTCTTGCTT    2040

GCTTTGCTAT  TTACACCACA  AAGGAAAAAG  CTGCACTGCT  ATACAAGAAA  ATTATGGAAA    2100

AATATTCTGT  AACCTTTATA  AGTAGGCATA  ACAGTTATAA  TCATAACATA  CTGTTTTTTC    2160

TTACTCCACA  CAGGCATAGA  GTGTCTGCTA  TTAATAACTA  TGCTCAAAAA  TTGTGTACCT    2220

TTAGCTTTTT  AATTTGTAAA  GGGGTTAATA  AGGAATATTT  GATGTATAGT  GCCTTGACTA    2280

GAGATCCGCC  TCCGGCGAAT  TTCTGCCATT  CATCCGCTTA  TTATCACTTA  TTCAGGCGTA    2340

GCACCAGGCG  TTTAAGGGCA  CCAATAACTG  CCTTAAAAAA  ATTACGCCCC  GCCCTGCCAC    2400

TCATCGCAGT  GCTCTAGAAC  TAGTGGATCC  CCCGGGCTGC  AGGAATTCGA  TGATCCTCGC    2460

GCCCCCTACC  CACCGTACTC  GTCAATTCCA  AGGGCATCGG  TAAACATCTG  CTCAAACTCG    2520

AAGTCGGCCA  TATCCAGAGC  GCCGTAGGGG  GCGGAGTCGT  GGGGGGTAAA  TCCCGGACCC    2580
```

```
GGGGAATCCC CGTCCCCCAA CATGTCCAGA TCGAAATCGT CTAGCGCGTC GGCATGCGCC  2640
ATCGCCACGT CCTCGCCGTC TAAGTGGAGC TCGTCCCCCA GGCTGACATC GGTCGGGGGG  2700
GCCGTCGACA GTCTGCGCGT GTGTCCCGCG GGGAGAAAGG ACAGGCGCGG AGCCGCCAGC  2760
CCCGCCTCTT CGGGGGCGTC GTCGTCCGGG AGATCGAGCA GGCCCTCGAT GGTAGACCCG  2820
TAATTGTTTT TCGTACGCGC GCGGCTGTAC GCGGACCCAC TTTCACATTT AAGTTGTTTT  2880
TCTAATCCGC ATATGATCAA TTCAAGGCCG AATAAGAAGG CTGGCTCTGC ACCTTGGTGA  2940
TCAAATAATT CGATAGCTTG TCGTAATAAT GGCGGCATAC TATCAGTAGT AGGTGTTTCC  3000
CTTTCTTCTT TAGCGACTTG ATGCTCTTGA TCTTCCAATA CGCAACCTAA AGTAAAATGC  3060
CCCACAGCGC TGAGTGCATA TAATGCATTC TCTAGTGAAA AACCTTGTTG GCATAAAAAG  3120
GCTAATTGAT TTTCGAGAGT TTCATACTGT TTTTCTGTAG GCCGTGTACC TAAATGTACT  3180
TTTGCTCCAT CGCGATGACT TAGTAAAGCA CATCTAAAAC TTTTAGCGTT ATTACGTAAA  3240
AAATCTTGCC AGCTTTCCCC TTCTAAAGGG CAAAAGTGAG TATGGTGCCT ATCTAACATC  3300
TCAATGGCTA AGGCGTCGAG CAAAGCCCGC TTATTTTTA CATGCCAATA CAATGTAGGC  3360
TGCTCTACAC CTAGCTTCTG GGCGAGTTTA CGGGTTGTTA AACCTTCGAT TCCGACCTCA  3420
TTAAGCAGCT CTAATGCGCT GTTAATCACT TTACTTTTAT CTAATCTAGA AGCCATGGTG  3480
GCAAGCTTAT CGATACCGTC GACCTCGACT CTAGAGGATC CCCGGGTACC GAGCTCGAAT  3540
TCGGGGCCGC GGAGGCTGGA TCGGTCCCGG TGTCTTCTAT GGAGGTCAAA ACAGCGTGGA  3600
TGGCGTCTCC AGGCGATCTG ACGGTTCACT AAACGAGCTC TGCTTATATA GGCCTCCCAC  3660
CGTACACGCC TACTCGACCC GGGTACCGAG CTCGACTTTC ACTTTTCTCT ATCACTGATA  3720
GGGAGTGGTA AACTCGACTT TCACTTTTCT CTATCACTGA TAGGGAGTGG TAAACTCGAC  3780
TTTCACTTTT CTCTATCACT GATAGGGAGT GGTAAACTCG ACTTTCACTT TTCTCTATCA  3840
CTGATAGGGA GTGGTAAACT CGACTTTCAC TTTTCTCTAT CACTGATAGG GAGTGGTAAA  3900
CTCGACTTTC ACTTTTCTCT ATCACTGATA GGGAGTGGTA AACTCGACTT TCACTTTTCT  3960
CTATCACTGA TAGGGAGTGG TAAACTCGAG GGGGGGCCCG GTACCCAGCT TTTGTTCCCT  4020
TTAGTGAGGG TTAATTGCGC GCTTGGCGTA ATCATGGTCA TAGCTGTTTC CTGTGTGAAA  4080
TTGTTATCCG CTCACAATTC CACACAACAT ACGAGCCGGA AGCATAAAGT GTAAAGCCTG  4140
GGGTGCCTAA TGAGTGAGCT AACTCACATT AATTGCGTTG CGCTCACTGC CCGCTTTCCA  4200
GTCGGGAAAC CTGTCGTGCC AGCTGCATTA ATGAATCGGC CAACGCGCGG GGAGAGGCGG  4260
TTTGCGTATT GGGCGCTCTT CCGCTTCCTC GCTCACTGAC TCGCTGCGCT CGGTCGTTCG  4320
GCTGCGGCGA GCGGTATCAG CTCACTCAAA GGCGGTAATA CGGTTATCCA CAGAATCAGG  4380
GGATAACGCA GGAAAGAACA TGTGAGCAAA AGGCCAGCAA AAGGCCAGGA ACCGTAAAAA  4440
GGCCGCGTTG CTGGCGTTTT TCCATAGGCT CCGCCCCCCT GACGAGCATC ACAAAAATCG  4500
ACGCTCAAGT CAGAGGTGGC GAAACCCGAC AGGACTATAA AGATACCAGG CGTTTCCCCC  4560
TGGAAGCTCC CTCGTGCGCT CTCCTGTTCC GACCCTGCCG CTTACCGGAT ACCTGTCCGC  4620
CTTTCTCCCT TCGGGAAGCG TGGCGCTTTC TCATAGCTCA CGCTGTAGGT ATCTCAGTTC  4680
GGTGTAGGTC GTTCGCTCCA AGCTGGGCTG TGTGCACGAA CCCCCCGTTC AGCCCGACCG  4740
CTGCGCCTTA TCCGGTAACT ATCGTCTTGA GTCCAACCCG GTAAGACACG ACTTATCGCC  4800
ACTGGCAGCA GCCACTGGTA ACAGGATTAG CAGAGCGAGG TATGTAGGCG GTGCTACAGA  4860
GTTCTTGAAG TGGTGGCCTA ACTACGGCTA CACTAGAAGG ACAGTATTTG GTATCTGCGC  4920
TCTGCTGAAG CCAGTTACCT TCGGAAAAAG AGTTGGTAGC TCTTGATCCG GCAAACAAAC  4980
```

-continued

| | | | | | |
|---|---|---|---|---|---|
| CACCGCTGGT | AGCGGTGGTT | TTTTTGTTTG | CAAGCAGCAG | ATTACGCGCA | GAAAAAAAGG | 5040 |
| ATCTCAAGAA | GATCCTTTGA | TCTTTTCTAC | GGGGTCTGAC | GCTCAGTGGA | ACGAAAACTC | 5100 |
| ACGTTAAGGG | ATTTTGGTCA | TGAGATTATC | AAAAGGATC | TTCACCTAGA | TCCTTTTAAA | 5160 |
| TTAAAAATGA | AGTTTAAAT | CAATCTAAAG | TATATATGAG | TAAACTTGGT | CTGACAGTTA | 5220 |
| CCAATGCTTA | ATCAGTGAGG | CACCTATCTC | AGCGATCTGT | CTATTTCGTT | CATCCATAGT | 5280 |
| TGCCTGACTC | CCCGTCGTGT | AGATAACTAC | GATACGGGAG | GGCTTACCAT | CTGGCCCAG | 5340 |
| TGCTGCAATG | ATACCGCGAG | ACCCACGCTC | ACCGGCTCCA | GATTATCAG | CAATAAACCA | 5400 |
| GCCAGCCGGA | AGGGCCGAGC | GCAGAAGTGG | TCCTGCAACT | TTATCCGCCT | CCATCCAGTC | 5460 |
| TATTAATTGT | TGCCGGGAAG | CTAGAGTAAG | TAGTTCGCCA | GTTAATAGTT | TGCGCAACGT | 5520 |
| TGTTGCCATT | GCTACAGGCA | TCGTGGTGTC | ACGCTCGTCG | TTTGGTATGG | CTTCATTCAG | 5580 |
| CTCCGGTTCC | CAACGATCAA | GGCGAGTTAC | ATGATCCCCC | ATGTTGTGCA | AAAAAGCGGT | 5640 |
| TAGCTCCTTC | GGTCCTCCGA | TCGTTGTCAG | AAGTAAGTTG | GCCGCAGTGT | TATCACTCAT | 5700 |
| GGTTATGGCA | GCACTGCATA | ATTCTCTTAC | TGTCATGCCA | TCCGTAAGAT | GCTTTTCTGT | 5760 |
| GACTGGTGAG | TACTCAACCA | AGTCATTCTG | AGAATAGTGT | ATGCGGCGAC | CGAGTTGCTC | 5820 |
| TTGCCCGGCG | TCAATACGGG | ATAATACCGC | GCCACATAGC | AGAACTTTAA | AAGTGCTCAT | 5880 |
| CATTGGAAAA | CGTTCTTCGG | GGCGAAAACT | CTCAAGGATC | TTACCGCTGT | TGAGATCCAG | 5940 |
| TTCGATGTAA | CCCACTCGTG | CACCCAACTG | ATCTTCAGCA | TCTTTTACTT | TCACCAGCGT | 6000 |
| TTCTGGGTGA | GCAAAAACAG | GAAGGCAAAA | TGCCGCAAAA | AAGGGAATAA | GGGCGACACG | 6060 |
| GAAATGTTGA | ATACTCATAC | TCTTCCTTTT | TCAATATTAT | TGAAGCATTT | ATCAGGGTTA | 6120 |
| TTGTCTCATG | AGCGGATACA | TATTTGAATG | TATTTAGAAA | AATAAACAAA | TAGGGGTTCC | 6180 |
| GCGCACATTT | CCCCGAAAAG | TGCCAC | | | | 6206 |

( 2 ) INFORMATION FOR SEQ ID NO:4:

( i ) SEQUENCE CHARACTERISTICS:
        ( A ) LENGTH: 336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Ser Arg Leu Asp Lys Ser Lys Val Ile Asn Ser Ala Leu Glu
 1               5                  10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140
```

| | | | | | | | | | | | | | | | |
|---|---|---|---|---|---|---|---|---|---|---|---|---|---|---|---|
| Cys | Val | Leu | Glu | Asp | Gln | Glu | His | Gln | Val | Ala | Lys | Glu | Glu | Arg | Glu |
| 145 | | | | | 150 | | | | 155 | | | | | | 160 |
| Thr | Pro | Thr | Thr | Asp | Ser | Met | Pro | Pro | Leu | Leu | Arg | Gln | Ala | Ile | Glu |
| | | | | 165 | | | | | 170 | | | | 175 | | |
| Leu | Phe | Asp | His | Gln | Gly | Ala | Glu | Pro | Ala | Phe | Leu | Phe | Gly | Leu | Glu |
| | | | 180 | | | | | 185 | | | | | 190 | | |
| Leu | Ile | Ile | Cys | Gly | Leu | Glu | Lys | Gln | Leu | Lys | Cys | Ser | Gly | Ser |
| | | 195 | | | | | 200 | | | | 205 | | | |
| Ala | Tyr | Ser | Arg | Ala | Arg | Thr | Lys | Asn | Asn | Tyr | Gly | Ser | Thr | Ile | Glu |
| | 210 | | | | | 215 | | | | | 220 | | | | |
| Gly | Leu | Leu | Asp | Leu | Pro | Asp | Asp | Asp | Ala | Pro | Glu | Glu | Ala | Gly | Leu |
| 225 | | | | | 230 | | | | | 235 | | | | | 240 |
| Ala | Ala | Pro | Arg | Leu | Ser | Phe | Leu | Pro | Ala | Gly | His | Thr | Arg | Arg | Leu |
| | | | | 245 | | | | | 250 | | | | | 255 | |
| Ser | Thr | Ala | Pro | Pro | Thr | Asp | Val | Ser | Leu | Gly | Asp | Glu | Leu | His | Leu |
| | | | 260 | | | | | 265 | | | | | 270 | | |
| Asp | Gly | Glu | Asp | Val | Ala | Met | Ala | His | Ala | Asp | Ala | Leu | Asp | Asp | Phe |
| | | 275 | | | | | 280 | | | | | 285 | | | |
| Asp | Leu | Asp | Met | Leu | Gly | Asp | Gly | Asp | Ser | Pro | Gly | Pro | Gly | Phe | Thr |
| | 290 | | | | | 295 | | | | | 300 | | | | |
| Pro | His | Asp | Ser | Ala | Pro | Tyr | Gly | Ala | Leu | Asp | Met | Ala | Asp | Phe | Glu |
| 305 | | | | | 310 | | | | | 315 | | | | | 320 |
| Phe | Glu | Gln | Met | Phe | Thr | Asp | Ala | Leu | Gly | Ile | Asp | Glu | Tyr | Gly | Gly |
| | | | | 325 | | | | | 330 | | | | | 335 | |

( 2 ) INFORMATION FOR SEQ ID NO:5:

( i ) SEQUENCE CHARACTERISTICS:
        ( A ) LENGTH: 4455 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 774..1778

( x i ) SEQUENCE DESCRIPTION: SEQ ID NO:5:

```
CTCGAGGAGC TTGGCCCATT GCATACGTTG TATCCATATC ATAATATGTA CATTTATATT      60
GGCTCATGTC CAACATTACC GCCATGTTGA CATTGATTAT TGACTAGTTA TTAATAGTAA     120
TCAATTACGG GGTCATTAGT TCATAGCCCA TATATGGAGT TCCGCGTTAC ATAACTTACG     180
GTAAATGGCC CGCCTGGCTG ACCGCCCAAC GACCCCGCC  CATTGACGTC AATAATGACG     240
TATGTTCCCA TAGTAACGCC AATAGGGACT TTCCATTGAC GTCAATGGGT GGAGTATTTA     300
CGCTAAACTG CCCACTTGGC AGTACATCAA GTGTATCATA TGCCAAGTAC GCCCCCTATT     360
GACGTCAATG ACGGTAAATG GCCCGCCTGG CATTATGCCC AGTACATGAC CTTATGGGAC     420
TTTCCTACTT GGCAGTACAT CTACGTATTA GTCATCGCTA TTACCATGGT GATGCGGTTT     480
TGGCAGTACA TCAATGGGCG TGGATAGCGG TTTGACTCAC GGGGATTTCC AAGTCTCCAC     540
CCCATTGACG TCAATGGGAG TTTGTTTTGG CACCAAAATC AACGGGACTT TCCAAAATGT     600
CGTAACAACT CCGCCCCATT GACGCAAATG GGCGGTAGGC GTGTACGGTG GAGGTCTAT     660
ATAAGCAGAG CTCGTTTAGT GAACCGTCAG ATCGCCTGGA GACGCCATCC ACGCTGTTTT     720
GACCTCCATA GAAGACACCG GGACCGATCC AGCCTCCGCG GCCCCGAATT CAT ATG       776
                                                          Met
```

| | | | | | | | | | | | | | | | | |
|---|---|---|---|---|---|---|---|---|---|---|---|---|---|---|---|---|
| TCT | AGA | TTA | GAT | AAA | AGT | AAA | GTG | ATT | AAC | AGC | GCA | TTA | GAG | CTG | CTT | 824 |
| Ser | Arg | Leu | Asp | Lys | Ser | Lys | Val | Ile | Asn | Ser | Ala | Leu | Glu | Leu | Leu | |
| | | 340 | | | | 345 | | | | | 350 | | | | | |
| AAT | GAG | GTC | GGA | ATC | GAA | GGT | TTA | ACA | ACC | CGT | AAA | CTC | GCC | CAG | AAG | 872 |
| Asn | Glu | Val | Gly | Ile | Glu | Gly | Leu | Thr | Thr | Arg | Lys | Leu | Ala | Gln | Lys | |
| 355 | | | | | 360 | | | | | 365 | | | | | | |
| CTA | GGT | GTA | GAG | CAG | CCT | ACA | TTG | TAT | TGG | CAT | GTA | AAA | AAT | AAG | CGG | 920 |
| Leu | Gly | Val | Glu | Gln | Pro | Thr | Leu | Tyr | Trp | His | Val | Lys | Asn | Lys | Arg | |
| 370 | | | | | 375 | | | | | 380 | | | | | 385 | |
| GCT | TTG | CTC | GAC | GCC | TTA | GCC | ATT | GAG | ATG | TTA | GAT | AGG | CAC | CAT | ACT | 968 |
| Ala | Leu | Leu | Asp | Ala | Leu | Ala | Ile | Glu | Met | Leu | Asp | Arg | His | His | Thr | |
| | | | | 390 | | | | 395 | | | | | 400 | | | |
| CAC | TTT | TGC | CCT | TTA | GAA | GGG | GAA | AGC | TGG | CAA | GAT | TTT | TTA | CGT | AAT | 1016 |
| His | Phe | Cys | Pro | Leu | Glu | Gly | Glu | Ser | Trp | Gln | Asp | Phe | Leu | Arg | Asn | |
| | | | 405 | | | | | 410 | | | | | 415 | | | |
| AAC | GCT | AAA | AGT | TTT | AGA | TGT | GCT | TTA | CTA | AGT | CAT | CGC | GAT | GGA | GCA | 1064 |
| Asn | Ala | Lys | Ser | Phe | Arg | Cys | Ala | Leu | Leu | Ser | His | Arg | Asp | Gly | Ala | |
| | | 420 | | | | | 425 | | | | | 430 | | | | |
| AAA | GTA | CAT | TTA | GGT | ACA | CGG | CCT | ACA | GAA | AAA | CAG | TAT | GAA | ACT | CTC | 1112 |
| Lys | Val | His | Leu | Gly | Thr | Arg | Pro | Thr | Glu | Lys | Gln | Tyr | Glu | Thr | Leu | |
| 435 | | | | | 440 | | | | | 445 | | | | | | |
| GAA | AAT | CAA | TTA | GCC | TTT | TTA | TGC | CAA | CAA | GGT | TTT | TCA | CTA | GAG | AAT | 1160 |
| Glu | Asn | Gln | Leu | Ala | Phe | Leu | Cys | Gln | Gln | Gly | Phe | Ser | Leu | Glu | Asn | |
| 450 | | | | | 455 | | | | | 460 | | | | | 465 | |
| GCA | TTA | TAT | GCA | CTC | AGC | GCT | GTG | GGG | CAT | TTT | ACT | TTA | GGT | TGC | GTA | 1208 |
| Ala | Leu | Tyr | Ala | Leu | Ser | Ala | Val | Gly | His | Phe | Thr | Leu | Gly | Cys | Val | |
| | | | | 470 | | | | | 475 | | | | | 480 | | |
| TTG | GAA | GAT | CAA | GAG | CAT | CAA | GTC | GCT | AAA | GAA | GAA | AGG | GAA | ACA | CCT | 1256 |
| Leu | Glu | Asp | Gln | Glu | His | Gln | Val | Ala | Lys | Glu | Glu | Arg | Glu | Thr | Pro | |
| | | | 485 | | | | | 490 | | | | | 495 | | | |
| ACT | ACT | GAT | AGT | ATG | CCG | CCA | TTA | TTA | CGA | CAA | GCT | ATC | GAA | TTA | TTT | 1304 |
| Thr | Thr | Asp | Ser | Met | Pro | Pro | Leu | Leu | Arg | Gln | Ala | Ile | Glu | Leu | Phe | |
| | | 500 | | | | | 505 | | | | | 510 | | | | |
| GAT | CAC | CAA | GGT | GCA | GAG | CCA | GCC | TTC | TTA | TTC | GGC | CTT | GAA | TTG | ATC | 1352 |
| Asp | His | Gln | Gly | Ala | Glu | Pro | Ala | Phe | Leu | Phe | Gly | Leu | Glu | Leu | Ile | |
| | 515 | | | | | 520 | | | | | 525 | | | | | |
| ATA | TGC | GGA | TTA | GAA | AAA | CAA | CTT | AAA | TGT | GAA | AGT | GGG | TCC | GCG | TAC | 1400 |
| Ile | Cys | Gly | Leu | Glu | Lys | Gln | Leu | Lys | Cys | Glu | Ser | Gly | Ser | Ala | Tyr | |
| 530 | | | | | 535 | | | | | 540 | | | | | 545 | |
| AGC | CGC | GCG | CGT | ACG | AAA | AAC | AAT | TAC | GGG | TCT | ACC | ATC | GAG | GGC | CTG | 1448 |
| Ser | Arg | Ala | Arg | Thr | Lys | Asn | Asn | Tyr | Gly | Ser | Thr | Ile | Glu | Gly | Leu | |
| | | | | 550 | | | | | 555 | | | | | 560 | | |
| CTC | GAT | CTC | CCG | GAC | GAC | GAC | GCC | CCC | GAA | GAG | GCG | GGG | CTG | GCG | GCT | 1496 |
| Leu | Asp | Leu | Pro | Asp | Asp | Asp | Ala | Pro | Glu | Glu | Ala | Gly | Leu | Ala | Ala | |
| | | | 565 | | | | | 570 | | | | | 575 | | | |
| CCG | CGC | CTG | TCC | TTT | CTC | CCC | GCG | GGA | CAC | ACG | CGC | AGA | CTG | TCG | ACG | 1544 |
| Pro | Arg | Leu | Ser | Phe | Leu | Pro | Ala | Gly | His | Thr | Arg | Arg | Leu | Ser | Thr | |
| | | 580 | | | | | 585 | | | | | 590 | | | | |
| GCC | CCC | CCG | ACC | GAT | GTC | AGC | CTG | GGG | GAC | GAG | CTC | CAC | TTA | GAC | GGC | 1592 |
| Ala | Pro | Pro | Thr | Asp | Val | Ser | Leu | Gly | Asp | Glu | Leu | His | Leu | Asp | Gly | |
| | 595 | | | | | 600 | | | | | 605 | | | | | |
| GAG | GAC | GTG | GCG | ATG | GCG | CAT | GCC | GAC | GCG | CTA | GAC | GAT | TTC | GAT | CTG | 1640 |
| Glu | Asp | Val | Ala | Met | Ala | His | Ala | Asp | Ala | Leu | Asp | Asp | Phe | Asp | Leu | |
| 610 | | | | | 615 | | | | | 620 | | | | | 625 | |
| GAC | ATG | TTG | GGG | GAC | GGG | GAT | TCC | CCG | GGT | CCG | GGA | TTT | ACC | CCC | CAC | 1688 |
| Asp | Met | Leu | Gly | Asp | Gly | Asp | Ser | Pro | Gly | Pro | Gly | Phe | Thr | Pro | His | |
| | | | | 630 | | | | | 635 | | | | | 640 | | |
| GAC | TCC | GCC | CCC | TAC | GGC | GCT | CTG | GAT | ATG | GCC | GAC | TTC | GAG | TTT | GAG | 1736 |
| Asp | Ser | Ala | Pro | Tyr | Gly | Ala | Leu | Asp | Met | Ala | Asp | Phe | Glu | Phe | Glu | |
| | | | 645 | | | | | 650 | | | | | 655 | | | |

| | | | | | | | | | | |
|---|---|---|---|---|---|---|---|---|---|---|
| CAG | ATG | TTT | ACC | GAT | GCC | CTT | GGA | ATT | GAC | GAG | TAC | GGT | GGG | 1778 |
| Gln | Met | Phe | Thr | Asp | Ala | Leu | Gly | Ile | Asp | Glu | Tyr | Gly | Gly | |
| | | 660 | | | | 665 | | | | | 670 | | | |

```
TAGGGGGCGC GAGGATCCAG ACATGATAAG ATACATTGAT GAGTTTGGAC AAACCACAAC     1838
TAGAATGCAG TGAAAAAAAT GCTTTATTTG TGAAATTTGT GATGCTATTG CTTTATTTGT     1898
AACCATTATA AGCTGCAATA AACAAGTTAA CAACAACAAT TGCATTCATT TTATGTTTCA     1958
GGTTCAGGGG GAGGTGTGGG AGGTTTTTTA AAGCAAGTAA AACCTCTACA AATGTGGTAT     2018
GGCTGATTAT GATCCTGCAA GCCTCGTCGT CTGGCCGGAC CACGCTATCT GTGCAAGGTC     2078
CCCGGACGCG CGCTCCATGA GCAGAGCGCC CGCCGCCGAG GCAAGACTCG GCGGCGCCC     2138
TGCCCGTCCC ACCAGGTCAA CAGGCGGTAA CCGGCCTCTT CATCGGGAAT GCGCGCGACC    2198
TTCAGCATCG CCGGCATGTC CCCTGGCGGA CGGAAGTAT  CAGCTCGACC AAGCTTGGCG    2258
AGATTTTCAG GAGCTAAGGA AGCTAAAATG GAGAAAAAAA TCACTGGATA TACCACCGTT    2318
GATATATCCC AATGGCATCG TAAAGAACAT TTTGAGGCAT TCAGTCAGT  TGCTCAATGT    2378
ACCTATAACC AGACCGTTCA GCTGCATTAA TGAATCGGCC AACGCGCGGG GAGAGGCGGT    2438
TTGCGTATTG GGCGCTCTTC CGCTTCCTCG CTCACTGACT CGCTGCGCTC GGTCGTTCGG    2498
CTGCGGCGAG CGGTATCAGC TCACTCAAAG GCGGTAATAC GGTTATCCAC AGAATCAGGG    2558
GATAACGCAG GAAAGAACAT GTGAGCAAAA GGCCAGCAAA AGGCCAGGAA CCGTAAAAAG    2618
GCCGCGTTGC TGGCGTTTTT CCATAGGCTC CGCCCCCCTG ACGAGCATCA CAAAAATCGA    2678
CGCTCAAGTC AGAGGTGGCG AAACCCGACA GGACTATAAA GATACCAGGC GTTTCCCCCT    2738
GGAAGCTCCC TCGTGCGCTC TCCTGTTCCG ACCCTGCCGC TTACCGGATA CCTGTCCGCC    2798
TTTCTCCCTT CGGGAAGCGT GGCGCTTTCT CAATGCTCAC GCTGTAGGTA TCTCAGTTCG    2858
GTGTAGGTCG TTCGCTCCAA GCTGGGCTGT GTGCACGAAC CCCCCGTTCA GCCCGACCGC    2918
TGCGCCTTAT CCGGTAACTA TCGTCTTGAG TCCAACCCGG TAAGACACGA CTTATCGCCA    2978
CTGGCAGCAG CCACTGGTAA CAGGATTAGC AGAGCGAGGT ATGTAGGCGG TGCTACAGAG    3038
TTCTTGAAGT GGTGGCCTAA CTACGGCTAC ACTAGAAGGA CAGTATTTGG TATCTGCGCT    3098
CTGCTGAAGC CAGTTACCTT CGGAAAAAGA GTTGGTAGCT CTTGATCCGG CAAACAAACC    3158
ACCGCTGGTA GCGGTGGTTT TTTTGTTTGC AAGCAGCAGA TTACGCGCAG AAAAAAAGGA    3218
TCTCAAGAAG ATCCTTTGAT CTTTTCTACG GGGTCTGACG CTCAGTGGAA CGAAAACTCA    3278
CGTTAAGGGA TTTTGGTCAT GAGATTATCA AAAAGGATCT TCACCTAGAT CCTTTTAAAT    3338
TAAAAATGAA GTTTTAAATC AATCTAAAGT ATATATGAGT AAACTTGGTC TGACAGTTAC    3398
CAATGCTTAA TCAGTGAGGC ACCTATCTCA GCGATCTGTC TATTTCGTTC ATCCATAGTT    3458
GCCTGACTCC CCGTCGTGTA GATAACTACG ATACGGGAGG GCTTACCATC TGGCCCCAGT    3518
GCTGCAATGA TACCGCGAGA CCCACGCTCA CCGGCTCCAG ATTTATCAGC AATAAACCAG    3578
CCAGCCGGAA GGGCCGAGCG CAGAAGTGGT CCTGCAACTT TATCCGCCTC CATCCAGTCT    3638
ATTAATTGTT GCCGGGAAGC TAGAGTAAGT AGTTCGCCAG TTAATAGTTT GCGCAACGTT    3698
GTTGCCATTG CTACAGGCAT CGTGGTGTCA CGCTCGTCGT TTGGTATGGC TTCATTCAGC    3758
TCCGGTTCCC AACGATCAAG GCGAGTTACA TGATCCCCCA TGTTGTGCAA AAAAGCGGTT    3818
AGCTCCTTCG GTCCTCCGAT CGTTGTCAGA AGTAAGTTGG CCGCAGTGTT ATCACTCATG    3878
GTTATGGCAG CACTGCATAA TTCTCTTACT GTCATGCCAT CCGTAAGATG CTTTTCTGTG    3938
ACTGGTGAGT ACTCAACCAA GTCATTCTGA GAATAGTGTA TGCGGCGACC GAGTTGCTCT    3998
TGCCCGGCGT CAATACGGGA TAATACCGCG CCACATAGCA GAACTTTAAA AGTGCTCATC    4058
```

```
ATTGGAAAAC  GTTCTTCGGG  GCGAAAACTC  TCAAGGATCT  TACCGCTGTT  GAGATCCAGT        4118

TCGATGTAAC  CCACTCGTGC  ACCCAACTGA  TCTTCAGCAT  CTTTTACTTT  CACCAGCGTT        4178

TCTGGGTGAG  CAAAACAGG   AAGGCAAAAT  GCCGCAAAAA  AGGGAATAAG  GGCGACACGG        4238

AAATGTTGAA  TACTCATACT  CTTCCTTTTT  CAATATTATT  GAAGCATTTA  TCAGGGTTAT        4298

TGTCTCATGA  GCGGATACAT  ATTTGAATGT  ATTTAGAAAA  ATAAACAAAT  AGGGGTTCCG        4358

CGCACATTTC  CCCGAAAAGT  GCCACCTGAC  GTCTAAGAAA  CCATTATTAT  CATGACATTA        4418

ACCTATAAAA  ATAGGCGTAT  CACGAGGCCC  TTTCGTC                                    4455
```

( 2 ) INFORMATION FOR SEQ ID NO:6:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
                35                  40                  45

Arg Ala Leu Leu Asp Ala Leu Ala Ile Glu Met Leu Asp Arg His His
            50                  55                  60

Thr His Phe Cys Pro Leu Glu Gly Glu Ser Trp Gln Asp Phe Leu Arg
 65                 70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
                100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
            195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Ala Pro Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
            275                 280                 285
```

-continued

| | | | | | | | | | | | | | | |
|---|---|---|---|---|---|---|---|---|---|---|---|---|---|---|
| Leu | Asp | Met | Leu | Gly | Asp | Gly | Asp | Ser | Pro | Gly | Pro | Gly | Phe | Thr | Pro |
| | | 290 | | | | 295 | | | | | 300 | | | | |

| His | Asp | Ser | Ala | Pro | Tyr | Gly | Ala | Leu | Asp | Met | Ala | Asp | Phe | Glu | Phe |
|---|---|---|---|---|---|---|---|---|---|---|---|---|---|---|---|
| 305 | | | | | 310 | | | | | 315 | | | | | 320 |

| Glu | Gln | Met | Phe | Thr | Asp | Ala | Leu | Gly | Ile | Asp | Glu | Tyr | Gly | Gly |
|---|---|---|---|---|---|---|---|---|---|---|---|---|---|---|
| | | | | 325 | | | | | 330 | | | | | 335 |

(2) INFORMATION FOR SEQ ID NO:7:

(i) SEQUENCE CHARACTERISTICS:
        (A) LENGTH: 5157 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 502..2184

(xi) SEQUENCE DESCRIPTION: SEQ ID NO:7:

```
GAATTCCTCG AGTTTACCAC TCCCTATCAG TGATAGAGAA AAGTGAAAGT CGAGTTTACC        60

ACTCCCTATC AGTGATAGAG AAAAGTGAAA GTCGAGTTTA CCACTCCCTA TCAGTGATAG       120

AGAAAAGTGA AAGTCGAGTT TACCACTCCC TATCAGTGAT AGAGAAAAGT GAAAGTCGAG       180

TTTACCACTC CCTATCAGTG ATAGAGAAAA GTGAAAGTCG AGTTTACCAC TCCCTATCAG       240

TGATAGAGAA AAGTGAAAGT CGAGTTTACC ACTCCCTATC AGTGATAGAG AAAAGTGAAA       300

GTCGAGCTCG GTACCCGGGT CGAGTAGGCG TGTACGGTGG GAGGCCTATA TAAGCAGAGC       360

TCGTTTAGTG AACCGTCAGA TCGCCTGGAG ACGCCATCCA CGCTGTTTTG ACCTCCATAG       420

AAGACACCGG GACCGATCCA GCCTCCGCGG CCCCGAATTC GAGCTCGGTA CCCGGGGATC       480

CTCTAGAGTC GACCTGCAGG C                                                 501
```

| CTCTAGAGTC | GACCTGCAGG | C | ATG | CAA | GCT | TGG | CAT | TCC | GGT | ACT | GTT | GGT | 531 |
|---|---|---|---|---|---|---|---|---|---|---|---|---|---|
| | | | Met | Gln | Ala | Trp | His | Ser | Gly | Thr | Val | Gly | |
| | | | | | | | 340 | | | | | 345 | |

| AAA | ATG | GAA | GAC | GCC | AAA | AAC | ATA | AAG | AAA | GGC | CCG | GCG | CCA | TTC | TAT | 579 |
|---|---|---|---|---|---|---|---|---|---|---|---|---|---|---|---|---|
| Lys | Met | Glu | Asp | Ala | Lys | Asn | Ile | Lys | Lys | Gly | Pro | Ala | Pro | Phe | Tyr | |
| | | | | 350 | | | | | 355 | | | | | 360 | | |

| CCT | CTA | GAG | GAT | GGA | ACC | GCT | GGA | GAG | CAA | CTG | GAT | AAG | CCT | ATG | AAG | 627 |
|---|---|---|---|---|---|---|---|---|---|---|---|---|---|---|---|---|
| Pro | Leu | Glu | Asp | Gly | Thr | Ala | Gly | Glu | Gln | Leu | Asp | Lys | Pro | Met | Lys | |
| | | | 365 | | | | | 370 | | | | | 375 | | | |

| AGA | TAC | GCC | CTG | GTT | CCT | GGA | ACA | ATT | GCT | TTT | ACA | GAT | GCA | CAT | ATC | 675 |
|---|---|---|---|---|---|---|---|---|---|---|---|---|---|---|---|---|
| Arg | Tyr | Ala | Leu | Val | Pro | Gly | Thr | Ile | Ala | Phe | Thr | Asp | Ala | His | Ile | |
| | | | 380 | | | | | 385 | | | | | 390 | | | |

| GAG | GTG | AAC | ATC | ACG | TAC | GCG | GAA | TAC | TTC | GAA | ATG | TCC | GTT | CGG | TTG | 723 |
|---|---|---|---|---|---|---|---|---|---|---|---|---|---|---|---|---|
| Glu | Val | Asn | Ile | Thr | Tyr | Ala | Glu | Tyr | Phe | Glu | Met | Ser | Val | Arg | Leu | |
| | | 395 | | | | | 400 | | | | | 405 | | | | |

| GCA | GAA | GCT | GTG | AAA | CGA | TAT | GGG | CTG | AAT | ACA | AAT | CAC | AGA | ATC | GTC | 771 |
|---|---|---|---|---|---|---|---|---|---|---|---|---|---|---|---|---|
| Ala | Glu | Ala | Val | Lys | Arg | Tyr | Gly | Leu | Asn | Thr | Asn | His | Arg | Ile | Val | |
| 410 | | | | | 415 | | | | | 420 | | | | | 425 | |

| GTA | TTC | AGT | GAA | AAC | TCT | CTT | CAA | TTC | TTT | ATG | CCG | GTG | TTG | GGC | GCG | 819 |
|---|---|---|---|---|---|---|---|---|---|---|---|---|---|---|---|---|
| Val | Phe | Ser | Glu | Asn | Ser | Leu | Gln | Phe | Phe | Met | Pro | Val | Leu | Gly | Ala | |
| | | | | 430 | | | | | 435 | | | | | 440 | | |

| TTA | TTT | ATC | GGA | GTT | GCA | GTT | GCG | CCC | GCG | AAC | GAC | ATT | TAT | AAT | GAA | 867 |
|---|---|---|---|---|---|---|---|---|---|---|---|---|---|---|---|---|
| Leu | Phe | Ile | Gly | Val | Ala | Val | Ala | Pro | Ala | Asn | Asp | Ile | Tyr | Asn | Glu | |
| | | | 445 | | | | | 450 | | | | | 455 | | | |

| CGT | GAA | TTG | CTC | AAC | AGT | ATG | AAC | ATT | TCG | CAG | CCT | AAC | GTA | GTG | TTG | 915 |
|---|---|---|---|---|---|---|---|---|---|---|---|---|---|---|---|---|
| Arg | Glu | Leu | Leu | Asn | Ser | Met | Asn | Ile | Ser | Gln | Pro | Asn | Val | Val | Leu | |
| | | | 460 | | | | | 465 | | | | | 470 | | | |

| GTT | TCC | AAA | AAG | GGG | TTG | CAA | AAA | ATT | TTG | AAC | GTG | CAA | AAA | AAA | TTA | 963 |
|---|---|---|---|---|---|---|---|---|---|---|---|---|---|---|---|---|

|  |  |  |  |  |  |  |  |  |  |  |  |  |  |  |  |
|---|---|---|---|---|---|---|---|---|---|---|---|---|---|---|---|
| Val | Ser | Lys | Lys | Gly | Leu | Gln | Lys | Ile | Leu | Asn | Val | Gln | Lys | Lys | Leu |
| 475 |  |  |  |  | 480 |  |  |  |  | 485 |  |  |  |  |  |

| CCA | ATA | ATC | CAG | AAA | ATT | ATT | ATC | ATG | GAT | CTC | AAA | ACG | GAT | TAC | CAG | 1011 |
|---|---|---|---|---|---|---|---|---|---|---|---|---|---|---|---|---|
| Pro | Ile | Ile | Gln | Lys | Ile | Ile | Ile | Met | Asp | Leu | Lys | Thr | Asp | Tyr | Gln |  |
| 490 |  |  |  | 495 |  |  |  |  | 500 |  |  |  |  | 505 |  |  |

| GGA | TTT | CAG | TCG | ATG | TAC | ACG | TTC | GTC | ACA | TCT | CAT | CTA | CCT | CCC | GGT | 1059 |
|---|---|---|---|---|---|---|---|---|---|---|---|---|---|---|---|---|
| Gly | Phe | Gln | Ser | Met | Tyr | Thr | Phe | Val | Thr | Ser | His | Leu | Pro | Pro | Gly |  |
|  |  |  |  | 510 |  |  |  |  | 515 |  |  |  |  | 520 |  |  |

| TTT | AAT | GAA | TAC | GAT | TTT | GTA | CCA | GAG | TCC | TTT | GAT | CGT | GAC | AAA | ACA | 1107 |
|---|---|---|---|---|---|---|---|---|---|---|---|---|---|---|---|---|
| Phe | Asn | Glu | Tyr | Asp | Phe | Val | Pro | Glu | Ser | Phe | Asp | Arg | Asp | Lys | Thr |  |
|  |  |  |  | 525 |  |  |  |  | 530 |  |  |  |  | 535 |  |  |

| ATT | GCA | CTG | ATA | ATG | AAT | TCC | TCT | GGA | TCT | ACT | GGG | TTA | CCT | AAG | GGT | 1155 |
|---|---|---|---|---|---|---|---|---|---|---|---|---|---|---|---|---|
| Ile | Ala | Leu | Ile | Met | Asn | Ser | Ser | Gly | Ser | Thr | Gly | Leu | Pro | Lys | Gly |  |
|  |  |  | 540 |  |  |  | 545 |  |  |  |  | 550 |  |  |  |  |

| GTG | GCC | CTT | CCG | CAT | AGA | ACT | GCC | TGC | GTC | AGA | TTC | TCG | CAT | GCC | AGA | 1203 |
|---|---|---|---|---|---|---|---|---|---|---|---|---|---|---|---|---|
| Val | Ala | Leu | Pro | His | Arg | Thr | Ala | Cys | Val | Arg | Phe | Ser | His | Ala | Arg |  |
|  |  | 555 |  |  |  |  | 560 |  |  |  |  | 565 |  |  |  |  |

| GAT | CCT | ATT | TTT | GGC | AAT | CAA | ATC | ATT | CCG | GAT | ACT | GCG | ATT | TTA | AGT | 1251 |
|---|---|---|---|---|---|---|---|---|---|---|---|---|---|---|---|---|
| Asp | Pro | Ile | Phe | Gly | Asn | Gln | Ile | Ile | Pro | Asp | Thr | Ala | Ile | Leu | Ser |  |
| 570 |  |  |  |  | 575 |  |  |  |  | 580 |  |  |  |  | 585 |  |

| GTT | GTT | CCA | TTC | CAT | CAC | GGT | TTT | GGA | ATG | TTT | ACT | ACA | CTC | GGA | TAT | 1299 |
|---|---|---|---|---|---|---|---|---|---|---|---|---|---|---|---|---|
| Val | Val | Pro | Phe | His | His | Gly | Phe | Gly | Met | Phe | Thr | Thr | Leu | Gly | Tyr |  |
|  |  |  |  | 590 |  |  |  |  | 595 |  |  |  |  | 600 |  |  |

| TTG | ATA | TGT | GGA | TTT | CGA | GTC | GTC | TTA | ATG | TAT | AGA | TTT | GAA | GAA | GAG | 1347 |
|---|---|---|---|---|---|---|---|---|---|---|---|---|---|---|---|---|
| Leu | Ile | Cys | Gly | Phe | Arg | Val | Val | Leu | Met | Tyr | Arg | Phe | Glu | Glu | Glu |  |
|  |  |  | 605 |  |  |  |  | 610 |  |  |  |  | 615 |  |  |  |

| CTG | TTT | TTA | CGA | TCC | CTT | CAG | GAT | TAC | AAA | ATT | CAA | AGT | GCG | TTG | CTA | 1395 |
|---|---|---|---|---|---|---|---|---|---|---|---|---|---|---|---|---|
| Leu | Phe | Leu | Arg | Ser | Leu | Gln | Asp | Tyr | Lys | Ile | Gln | Ser | Ala | Leu | Leu |  |
|  |  |  | 620 |  |  |  |  | 625 |  |  |  |  | 630 |  |  |  |

| GTA | CCA | ACC | CTA | TTT | TCA | TTC | TTC | GCC | AAA | AGC | ACT | CTG | ATT | GAC | AAA | 1443 |
|---|---|---|---|---|---|---|---|---|---|---|---|---|---|---|---|---|
| Val | Pro | Thr | Leu | Phe | Ser | Phe | Phe | Ala | Lys | Ser | Thr | Leu | Ile | Asp | Lys |  |
|  | 635 |  |  |  |  | 640 |  |  |  |  | 645 |  |  |  |  |  |

| TAC | GAT | TTA | TCT | AAT | TTA | CAC | GAA | ATT | GCT | TCT | GGG | GGC | GCA | CCT | CTT | 1491 |
|---|---|---|---|---|---|---|---|---|---|---|---|---|---|---|---|---|
| Tyr | Asp | Leu | Ser | Asn | Leu | His | Glu | Ile | Ala | Ser | Gly | Gly | Ala | Pro | Leu |  |
| 650 |  |  |  |  | 655 |  |  |  |  | 660 |  |  |  |  | 665 |  |

| TCG | AAA | GAA | GTC | GGG | GAA | GCG | GTT | GCA | AAA | CGC | TTC | CAT | CTT | CCA | GGG | 1539 |
|---|---|---|---|---|---|---|---|---|---|---|---|---|---|---|---|---|
| Ser | Lys | Glu | Val | Gly | Glu | Ala | Val | Ala | Lys | Arg | Phe | His | Leu | Pro | Gly |  |
|  |  |  |  | 670 |  |  |  |  | 675 |  |  |  |  | 680 |  |  |

| ATA | CGA | CAA | GGA | TAT | GGG | CTC | ACT | GAG | ACT | ACA | TCA | GCT | ATT | CTG | ATT | 1587 |
|---|---|---|---|---|---|---|---|---|---|---|---|---|---|---|---|---|
| Ile | Arg | Gln | Gly | Tyr | Gly | Leu | Thr | Glu | Thr | Thr | Ser | Ala | Ile | Leu | Ile |  |
|  |  |  | 685 |  |  |  |  | 690 |  |  |  |  | 695 |  |  |  |

| ACA | CCC | GAG | GGG | GAT | GAT | AAA | CCG | GGC | GCC | GTC | GGT | AAA | GTT | GTT | CCA | 1635 |
|---|---|---|---|---|---|---|---|---|---|---|---|---|---|---|---|---|
| Thr | Pro | Glu | Gly | Asp | Asp | Lys | Pro | Gly | Ala | Val | Gly | Lys | Val | Val | Pro |  |
|  |  | 700 |  |  |  |  | 705 |  |  |  |  | 710 |  |  |  |  |

| TTT | TTT | GAA | GCG | AAG | GTT | GTG | GAT | CTG | GAT | ACC | GGG | AAA | ACG | CTG | GGC | 1683 |
|---|---|---|---|---|---|---|---|---|---|---|---|---|---|---|---|---|
| Phe | Phe | Glu | Ala | Lys | Val | Val | Asp | Leu | Asp | Thr | Gly | Lys | Thr | Leu | Gly |  |
| 715 |  |  |  |  | 720 |  |  |  |  | 725 |  |  |  |  |  |  |

| GTT | AAT | CAG | AGA | GGC | GAA | TTA | TGT | GTC | AGA | GGA | CCT | ATG | ATG | ATG | TCC | 1731 |
|---|---|---|---|---|---|---|---|---|---|---|---|---|---|---|---|---|
| Val | Asn | Gln | Arg | Gly | Glu | Leu | Cys | Val | Arg | Gly | Pro | Met | Met | Met | Ser |  |
| 730 |  |  |  |  | 735 |  |  |  |  | 740 |  |  |  |  | 745 |  |

| GGT | TAT | GTA | AAC | AAT | CCG | CAA | GCG | ACC | AAC | GCC | TTG | ATT | GAC | AAG | GAT | 1779 |
|---|---|---|---|---|---|---|---|---|---|---|---|---|---|---|---|---|
| Gly | Tyr | Val | Asn | Asn | Pro | Gln | Ala | Thr | Asn | Ala | Leu | Ile | Asp | Lys | Asp |  |
|  |  |  |  | 750 |  |  |  |  | 755 |  |  |  |  | 760 |  |  |

| GGA | TGG | CTA | CAT | TCT | GGA | GAC | ATA | GCT | TAC | TGG | GAC | GAA | GAC | GAA | CAC | 1827 |
|---|---|---|---|---|---|---|---|---|---|---|---|---|---|---|---|---|
| Gly | Trp | Leu | His | Ser | Gly | Asp | Ile | Ala | Tyr | Trp | Asp | Glu | Asp | Glu | His |  |
|  |  |  | 765 |  |  |  |  | 770 |  |  |  |  | 775 |  |  |  |

| TTC | TTC | ATA | GTT | GAC | CGC | TTG | AAG | TCT | TTA | ATT | AAA | TAC | AAA | GGA | TAT | 1875 |
|---|---|---|---|---|---|---|---|---|---|---|---|---|---|---|---|---|
| Phe | Phe | Ile | Val | Asp | Arg | Leu | Lys | Ser | Leu | Ile | Lys | Tyr | Lys | Gly | Tyr |  |
|  |  | 780 |  |  |  |  | 785 |  |  |  |  | 790 |  |  |  |  |

| CAG | GTG | GCC | CCC | GCT | GAA | TTG | GAA | TCG | ATA | TTG | TTA | CAA | CAC | CCC | AAC | 1923 |

```
           Gln  Val  Ala  Pro  Ala  Glu  Leu  Glu  Ser  Ile  Leu  Leu  Gln  His  Pro  Asn
                795                     800                    805

ATC  TTC  GAC  GCG  GGC  GTG  GCA  GGT  CTT  CCC  GAC  GAT  GAC  GCC  GGT  GAA            1971
Ile  Phe  Asp  Ala  Gly  Val  Ala  Gly  Leu  Pro  Asp  Asp  Asp  Ala  Gly  Glu
810                     815                    820                         825

CTT  CCC  GCC  GCC  GTT  GTT  GTT  TTG  GAG  CAC  GGA  AAG  ACG  ATG  ACG  GAA            2019
Leu  Pro  Ala  Ala  Val  Val  Val  Leu  Glu  His  Gly  Lys  Thr  Met  Thr  Glu
                         830                    835                         840

AAA  GAG  ATC  GTG  GAT  TAC  GTC  GCC  AGT  CAA  GTA  ACA  ACC  GCC  AAA  AAG            2067
Lys  Glu  Ile  Val  Asp  Tyr  Val  Ala  Ser  Gln  Val  Thr  Thr  Ala  Lys  Lys
                    845                    850                    855

TTG  CGC  GGA  GGA  GTT  GTG  TTT  GTG  GAC  GAA  GTA  CCG  AAA  GGT  CTT  ACC            2115
Leu  Arg  Gly  Gly  Val  Val  Phe  Val  Asp  Glu  Val  Pro  Lys  Gly  Leu  Thr
               860                    865                    870

GGA  AAA  CTC  GAC  GCA  AGA  AAA  ACT  AGA  GAG  ATC  CTC  ATA  AAG  GCC  AAG            2163
Gly  Lys  Leu  Asp  Ala  Arg  Lys  Thr  Arg  Glu  Ile  Leu  Ile  Lys  Ala  Lys
     875                    880                    885

AAG  GGC  GGA  AAG  TCC  AAA  TTG  TAAAATGTAA  CTGTATTCAG  CGATGACGAA                     2214
Lys  Gly  Gly  Lys  Ser  Lys  Leu
890                     895

ATTCTTAGCT  ATTGTAATGA  CTCTAGAGGA  TCTTTGTGAA  GGAACCTTAC  TTCTGTGGTG                    2274

TGACATAATT  GGACAAACTA  CCTACAGAGA  TTTAAAGCTC  TAAGGTAAAT  ATAAAATTTT                    2334

TAAGTGTATA  ATGTGTTAAA  CTACTGATTC  TAATTGTTTG  TGTATTTTAG  ATTCCAACCT                    2394

ATGGAACTGA  TGAATGGGAG  CAGTGGTGGA  ATGCCTTTAA  TGAGGAAAAC  CTGTTTTGCT                    2454

CAGAAGAAAT  GCCATCTAGT  GATGATGAGG  CTACTGCTGA  CTCTCAACAT  TCTACTCCTC                    2514

CAAAAAAGAA  GAGAAAGGTA  GAAGACCCCA  AGGACTTTCC  TTCAGAATTG  CTAAGTTTTT                    2574

TGAGTCATGC  TGTGTTTAGT  AATAGAACTC  TTGCTTGCTT  TGCTATTTAC  ACCACAAAGG                    2634

AAAAAGCTGC  ACTGCTATAC  AAGAAAATTA  TGGAAAAATA  TTCTGTAACC  TTTATAAGTA                    2694

GGCATAACAG  TTATAATCAT  AACATACTGT  TTTTCTTAC   TCCACACAGG  CATAGAGTGT                    2754

CTGCTATTAA  TAACTATGCT  CAAAAATTGT  GTACCTTTAG  CTTTTTAATT  TGTAAGGGG                     2814

TTAATAAGGA  ATATTTGATG  TATAGTGCCT  TGATCATAAT  CAGCCATACC  ACATTTGTAG                    2874

AGGTTTTACT  TGCTTTAAAA  AACCTCCCAC  ACCTCCCCCT  GAACCTGAAA  CATAAAATGA                    2934

ATGCAATTGT  TGTTGTTAAC  TTGTTTATTG  CAGCTTATAA  TGGTTACAAA  TAAAGCAATA                    2994

GCATCACAAA  TTTCACAAAT  AAAGCATTTT  TTTCACTGCA  TTCTAGTTGT  GGTTTGTCCA                    3054

AACTCATCAA  TGTATCTTAT  CATGTCTGCC  TCTAGAGCTG  CATTAATGAA  TCGGCCAACG                    3114

CGCGGGGAGA  GGCGGTTTGC  GTATTGGGCG  CTCTTCCGCT  TCCTCGCTCA  CTGACTCGCT                    3174

GCGCTCGGTC  GTTCGGCTGC  GGCGAGCGGT  ATCAGCTCAC  TCAAAGGCGG  TAATACGGTT                    3234

ATCCACAGAA  TCAGGGGATA  ACGCAGGAAA  GAACATGTGA  GCAAAAGGCC  AGCAAAAGGC                    3294

CAGGAACCGT  AAAAAGGCCG  CGTTGCTGGC  GTTTTCCAT   AGGCTCCGCC  CCCCTGACGA                    3354

GCATCACAAA  AATCGACGCT  CAAGTCAGAG  GTGGCGAAAC  CCGACAGGAC  TATAAAGATA                    3414

CCAGGCGTTT  CCCCCTGGAA  GCTCCCTCGT  GCGCTCTCCT  GTTCCGACCC  TGCCGCTTAC                    3474

CGGATACCTG  TCCGCCTTTC  TCCCTTCGGG  AAGCGTGGCG  CTTTCTCAAT  GCTCACGCTG                    3534

TAGGTATCTC  AGTTCGGTGT  AGGTCGTTCG  CTCCAAGCTG  GGCTGTGTGC  ACGAACCCCC                    3594

CGTTCAGCCC  GACCGCTGCG  CCTTATCCGG  TAACTATCGT  CTTGAGTCCA  ACCCGGTAAG                    3654

ACACGACTTA  TCGCCACTGG  CAGCAGCCAC  TGGTAACAGG  ATTAGCAGAG  CGAGGTATGT                    3714

AGGCGGTGCT  ACAGAGTTCT  TGAAGTGGTG  GCCTAACTAC  GGCTACACTA  GAAGGACAGT                    3774

ATTTGGTATC  TGCGCTCTGC  TGAAGCCAGT  TACCTTCGGA  AAAAGAGTTG  GTAGCTCTTG                    3834
```

|  |  |  |  |  |  |
|---|---|---|---|---|---|
| ATCCGGCAAA | CAAACCACCG | CTGGTAGCGG | TGGTTTTTTT | GTTTGCAAGC | AGCAGATTAC | 3894 |
| GCGCAGAAAA | AAAGGATCTC | AAGAAGATCC | TTTGATCTTT | TCTACGGGGT | CTGACGCTCA | 3954 |
| GTGGAACGAA | AACTCACGTT | AAGGGATTTT | GGTCATGAGA | TTATCAAAAA | GGATCTTCAC | 4014 |
| CTAGATCCTT | TTAAATTAAA | AATGAAGTTT | TAAATCAATC | TAAAGTATAT | ATGAGTAAAC | 4074 |
| TTGGTCTGAC | AGTTACCAAT | GCTTAATCAG | TGAGGCACCT | ATCTCAGCGA | TCTGTCTATT | 4134 |
| TCGTTCATCC | ATAGTTGCCT | GACTCCCCGT | CGTGTAGATA | ACTACGATAC | GGGAGGGCTT | 4194 |
| ACCATCGGC | CCCAGTGCTG | CAATGATACC | GCGAGACCCA | CGCTCACCGG | CTCCAGATTT | 4254 |
| ATCAGCAATA | AACCAGCCAG | CCGGAAGGGC | CGAGCGCAGA | AGTGGTCCTG | CAACTTTATC | 4314 |
| CGCCTCCATC | CAGTCTATTA | ATTGTTGCCG | GGAAGCTAGA | GTAAGTAGTT | CGCCAGTTAA | 4374 |
| TAGTTTGCGC | AACGTTGTTG | CCATTGCTAC | AGGCATCGTG | GTGTCACGCT | CGTCGTTTGG | 4434 |
| TATGGCTTCA | TTCAGCTCCG | GTTCCCAACG | ATCAAGGCGA | GTTACATGAT | CCCCCATGTT | 4494 |
| GTGCAAAAAA | GCGGTTAGCT | CCTTCGGTCC | TCCGATCGTT | GTCAGAAGTA | AGTTGGCCGC | 4554 |
| AGTGTTATCA | CTCATGGTTA | TGGCAGCACT | GCATAATTCT | CTTACTGTCA | TGCCATCCGT | 4614 |
| AAGATGCTTT | TCTGTGACTG | GTGAGTACTC | AACCAAGTCA | TTCTGAGAAT | AGTGTATGCG | 4674 |
| GCGACCGAGT | TGCTCTTGCC | CGGCGTCAAT | ACGGGATAAT | ACCGCGCCAC | ATAGCAGAAC | 4734 |
| TTTAAAAGTG | CTCATCATTG | GAAAACGTTC | TTCGGGGCGA | AAACTCTCAA | GGATCTTACC | 4794 |
| GCTGTTGAGA | TCCAGTTCGA | TGTAACCCAC | TCGTGCACCC | AACTGATCTT | CAGCATCTTT | 4854 |
| TACTTTCACC | AGCGTTTCTG | GGTGAGCAAA | AACAGGAAGG | CAAAATGCCG | CAAAAAAGGG | 4914 |
| AATAAGGGCG | ACACGGAAAT | GTTGAATACT | CATACTCTTC | CTTTTTCAAT | ATTATTGAAG | 4974 |
| CATTTATCAG | GGTTATTGTC | TCATGAGCGG | ATACATATTT | GAATGTATTT | AGAAAAATAA | 5034 |
| ACAAATAGGG | GTTCCGCGCA | CATTTCCCCG | AAAAGTGCCA | CCTGACGTGA | CGTCTAAGAA | 5094 |
| ACCATTATTA | TCATGACATT | AACCTATAAA | AATAGGCGTA | TCACGAGGCC | CTTTCGTCTT | 5154 |
| CAA |  |  |  |  |  | 5157 |

( 2 ) INFORMATION FOR SEQ ID NO:8:

( i ) SEQUENCE CHARACTERISTICS:
        ( A ) LENGTH: 561 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Gln Ala Trp His Ser Gly Thr Val Gly Lys Met Glu Asp Ala Lys
 1               5                  10                  15

Asn Ile Lys Lys Gly Pro Ala Pro Phe Tyr Pro Leu Glu Asp Gly Thr
            20                  25                  30

Ala Gly Glu Gln Leu Asp Lys Pro Met Lys Arg Tyr Ala Leu Val Pro
        35                  40                  45

Gly Thr Ile Ala Phe Thr Asp Ala His Ile Glu Val Asn Ile Thr Tyr
    50                  55                  60

Ala Glu Tyr Phe Glu Met Ser Val Arg Leu Ala Glu Ala Val Lys Arg
65                  70                  75                  80

Tyr Gly Leu Asn Thr Asn His Arg Ile Val Val Phe Ser Glu Asn Ser
                85                  90                  95

Leu Gln Phe Phe Met Pro Val Leu Gly Ala Leu Phe Ile Gly Val Ala
            100                 105                 110
```

```
Val Ala Pro Ala Asn Asp Ile Tyr Asn Glu Arg Glu Leu Leu Asn Ser
        115                 120                 125
Met Asn Ile Ser Gln Pro Asn Val Val Leu Val Ser Lys Lys Gly Leu
    130                 135                 140
Gln Lys Ile Leu Asn Val Gln Lys Lys Leu Pro Ile Ile Gln Lys Ile
145                 150                 155                 160
Ile Ile Met Asp Leu Lys Thr Asp Tyr Gln Gly Phe Gln Ser Met Tyr
                165                 170                 175
Thr Phe Val Thr Ser His Leu Pro Pro Gly Phe Asn Glu Tyr Asp Phe
            180                 185                 190
Val Pro Glu Ser Phe Asp Arg Asp Lys Thr Ile Ala Leu Ile Met Asn
        195                 200                 205
Ser Ser Gly Ser Thr Gly Leu Pro Lys Gly Val Ala Leu Pro His Arg
    210                 215                 220
Thr Ala Cys Val Arg Phe Ser His Ala Arg Asp Pro Ile Phe Gly Asn
225                 230                 235                 240
Gln Ile Ile Pro Asp Thr Ala Ile Leu Ser Val Val Pro Phe His His
                245                 250                 255
Gly Phe Gly Met Phe Thr Thr Leu Gly Tyr Leu Ile Cys Gly Phe Arg
            260                 265                 270
Val Val Leu Met Tyr Arg Phe Glu Glu Glu Leu Phe Leu Arg Ser Leu
        275                 280                 285
Gln Asp Tyr Lys Ile Gln Ser Ala Leu Leu Val Pro Thr Leu Phe Ser
    290                 295                 300
Phe Phe Ala Lys Ser Thr Leu Ile Asp Lys Tyr Asp Leu Ser Asn Leu
305                 310                 315                 320
His Glu Ile Ala Ser Gly Gly Ala Pro Leu Ser Lys Glu Val Gly Glu
                325                 330                 335
Ala Val Ala Lys Arg Phe His Leu Pro Gly Ile Arg Gln Gly Tyr Gly
            340                 345                 350
Leu Thr Glu Thr Thr Ser Ala Ile Leu Ile Thr Pro Glu Gly Asp Asp
        355                 360                 365
Lys Pro Gly Ala Val Gly Lys Val Val Pro Phe Phe Glu Ala Lys Val
    370                 375                 380
Val Asp Leu Asp Thr Gly Lys Thr Leu Gly Val Asn Gln Arg Gly Glu
385                 390                 395                 400
Leu Cys Val Arg Gly Pro Met Met Met Ser Gly Tyr Val Asn Asn Pro
                405                 410                 415
Gln Ala Thr Asn Ala Leu Ile Asp Lys Asp Gly Trp Leu His Ser Gly
            420                 425                 430
Asp Ile Ala Tyr Trp Asp Glu Asp Glu His Phe Phe Ile Val Asp Arg
        435                 440                 445
Leu Lys Ser Leu Ile Lys Tyr Lys Gly Tyr Gln Val Ala Pro Ala Glu
    450                 455                 460
Leu Glu Ser Ile Leu Leu Gln His Pro Asn Ile Phe Asp Ala Gly Val
465                 470                 475                 480
Ala Gly Leu Pro Asp Asp Asp Ala Gly Glu Leu Pro Ala Ala Val Val
                485                 490                 495
Val Leu Glu His Gly Lys Thr Met Thr Glu Lys Glu Ile Val Asp Tyr
            500                 505                 510
Val Ala Ser Gln Val Thr Thr Ala Lys Lys Leu Arg Gly Gly Val Val
        515                 520                 525
Phe Val Asp Glu Val Pro Lys Gly Leu Thr Gly Lys Leu Asp Ala Arg
    530                 535                 540
```

-continued

| Lys | Thr | Arg | Glu | Ile | Leu | Ile | Lys | Ala | Lys | Lys | Gly | Gly | Lys | Ser | Lys |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |
| Leu |     |     |     |     |     |     |     |     |     |     |     |     |     |     |     |